(12) United States Patent
Jure-Kunkel et al.

(10) Patent No.: US 8,716,452 B2
(45) Date of Patent: *May 6, 2014

(54) FULLY HUMAN ANTIBODIES AGAINST HUMAN 4-1BB

(75) Inventors: Maria Jure-Kunkel, Plainsboro, NJ (US); Laura J. Hefta, Pennington, NJ (US); Marc Santoro, Yardley, PA (US); Subinay Ganguly, Newtown, PA (US); Edward L. Halk, Sunnyvale, CA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 42 days.

This patent is subject to a terminal disclaimer.

(21) Appl. No.: 13/368,710

(22) Filed: Feb. 8, 2012

(65) Prior Publication Data

US 2012/0141494 A1 Jun. 7, 2012

Related U.S. Application Data

(60) Continuation of application No. 12/653,137, filed on Dec. 9, 2009, now Pat. No. 8,137,667, which is a division of application No. 11/903,106, filed on Sep. 20, 2007, now Pat. No. 7,659,384.

(51) Int. Cl.
*A61K 39/395* (2006.01)
*C07K 16/00* (2006.01)

(52) U.S. Cl.
USPC ................................ 530/388.1; 424/141.1

(58) Field of Classification Search
None
See application file for complete search history.

(56) References Cited

U.S. PATENT DOCUMENTS

| | | | |
|---|---|---|---|
| 6,458,934 B1 | 10/2002 | Hong et al. | |
| 6,569,997 B1 | 5/2003 | Kwon | |
| 7,288,638 B2 | 10/2007 | Jure-Kunkel et al. | |
| 8,137,667 B2 * | 3/2012 | Jure-Kunkel et al. | 424/130.1 |

FOREIGN PATENT DOCUMENTS

| | | |
|---|---|---|
| CA | 2108401 | 3/1995 |
| WO | WO94/26290 | 11/1994 |
| WO | WO95/07984 | 3/1995 |
| WO | WO96/32495 | 1/1996 |
| WO | WO96/29348 | 9/1996 |
| WO | WO 97/33898 | 9/1997 |
| WO | WO 98/16249 | 4/1998 |
| WO | WO 99/36093 | 7/1999 |
| WO | WO 99/44629 | 9/1999 |
| WO | WO 00/29445 | 5/2000 |
| WO | WO 02/36141 | 5/2002 |
| WO | WO 03/006632 | 1/2003 |
| WO | WO 03/031474 | 4/2003 |
| WO | WO 03/049755 | 6/2003 |
| WO | WO 03/083069 | 10/2003 |
| WO | WO 03/084999 | 10/2003 |
| WO | WO 2004/006853 | 1/2004 |
| WO | WO 2004/010947 | 2/2004 |
| WO | WO 2004/019866 | 3/2004 |
| WO | WO 2004/055513 | 7/2004 |
| WO | WO 2004/093831 | 11/2004 |

OTHER PUBLICATIONS

Abbas, A., et al., "T Lymphocyte Antigen Recognition and Activation", Cellular and Molecular Immunology, Chapter 7 Third Edition, pp. 139-170 (1997).
Alderson, M.R., et al., "Molecular and biological characterization of human 4-1BB and its ligand", Eur. J. Immunol., vol. 24, pp. 2219-2227 (1994).
Angal, S., et al., "A single Amino Acid Substitution Abolishes the Heterogeneity of Chimeric Mouse/Human (IgG4) Antibody", Molecular Immunology, vol. 30(1), pp. 105-108 (1993).
Antonia, S. et al, "Current developments of immunotherapy in the clinic", Current Opinion in immunology, vol. 16, pp. 130-136 (2004).
Ashkenazi, A., Nature, "Targeting Death and Decoy Receptors of the Tumour-Necrosis Factor Superfamily", Nature, vol. 2, pp. 420-430 (2002).
Bansal-Pakala, P. et al., "Defective T Cell Priming Associated with Aging Can Be Rescued by Signaling Through 4-1BB (CD137)", The Journal of Immunology, vol. 169, pp. 5005-5009 (2002).
Bassi, P.F., "BCG (*Bacillus* of Calmette Guerin) therapy of high-risk superficial bladder cancer", Surgical Oncology, vol., 11, pp. 77-83, (2002).
Bertley, F., et al., "Control of Simian/Human Immunodeficiency Virus Viremia and Disease Progression after IL-2-Augmented DNA-Modified *Vaccinia* Virus Ankara Nasal Vaccination in Nonhuman Primates", The Journal of Immunology, vol. 172, pp. 3745-3757, (2004).
Bu, Z., et al., "Enhanced cellular immune response against SIV Gag induced by immunization with DNA vaccines expressing assembly and release-defective SIV Gag proteins", Virology, vol. 309, pp. 272-281, (2003).
Chambers, C. et al., Current Opinion in Immunology, "Co-Stimulation in T-Cell Responses", vol. 19, pp. 396-404 (1997).
Chothia, C. et. Al., J. Mol. Biol., "Canonical Structures for the Hypervariable Regions of Immunoglobulins", vol. 196, pp. 901-917 (1987).
Cooper, D., "4-1BB (CD137) controls the clonal expansion and survival of CD8 T cells in vivo but does not contribute to the development of cytotoxicity", Eur. J. Immunology, vol. 32, pp. 521-529 (2002).
DeBenedette, M. et al., Journal of Immunology, "Costimulation of CD28 T Lymphocytes by 4-1BB Ligand", vol. 158, pp. 551-559 (1997).
DeBenedette, M., et al., "Analysis of 4-1BB Ligand (4-1BBL)-Deficient Mice and of Mice Lacking Both 4-1BBL and CD28 Reveals a Role for 4-1BBL in Skin Allograft Rejection and in the Cytotoxic T Cell Response to Influenza Virus", pp. 4833-4841 (1999).

(Continued)

*Primary Examiner* — Ilia Ouspenski
(74) *Attorney, Agent, or Firm* — Paul D. Golian

(57) ABSTRACT

Fully human antibodies and antigen-binding portions thereof that bind to human 4-1BB and that allow binding of human 4-1BB to a human 4-1BB ligand. In one aspect, the antibody is an IgG4 antibody. Also provided is a method for treating a disease in a subject comprising administering a therapeutically effective amount of the antibody to said subject.

3 Claims, 34 Drawing Sheets

(56) References Cited

OTHER PUBLICATIONS

Dranoff, G., et al., "Vaccination with irradiated tumor cells engineered to secrete murine granulocyte-macrophage colony-stimulating factor stimulates potent, specific, and long-lasting anti-tumor immunity", Proc. Nat'l. Acad. Sci. USA, vol. 90, pp. 3539-3543, (1993).
Elder, D., Acta Oncologica, "Tumor Progression, Early Diagnosis and Prognosis of Melanoma", vol. 38, pp. 535-547 (1999).
Fishman, M. et al., Expert Opin. Investig. Drugs, "Novel Therapies for High-Risk Superficial Bladder Cancer", vol. 11, pp. 77-83 (2002).
Foell, J., et al., "CD137-Mediated T Cell Co-Stimulation Terminates Existing Autoimmune Disease in SLE-Prone NZB/NZW F1 Mice", N.Y. Acad. Sci., vol. 987, pp. 230-235 (2003).
Foote, J. at al., J.Mol. Biol., "Antibody Framework Residues Affecting the Conformation of the Hypervariable Loops", vol. 224, pp. 487-499 (1992).
Futagawa, T., et al., "Expression and function of 4-1BB and 4-1BB ligand on murine dendritic cells", International Immunology, vol., 14, pp. 275-286, (2001).
Goodwin, R.G., et al., "Molecular cloning of a ligand for the inducible T cell gene 4-1BB: a member of an emerging family of cytokines with homology to tumor necrosis factor", Eur. J. Immunol., vol. 23, pp. 2631-2641 (1993).
Gramaglia, I. et al., "Co-stimulation of antigen-specific CD4 T cells by 4-1BB ligand", Eur. J. Immunol., vol. 30, pp. 293-402, (2000).
Guinn, B., et al., "4-1BBL Cooperates with B7-1 and B7-2 in Converting a B Cell Lymphoma Cell Line into a Long-Lasting Antitumor Vaccine", The American Association of Immunologists, vol. 162 pp. 5003-5010, (1999).
Hakim, F.T., et al., "Aging, Immunity and Cancer", Current Opinion in Immunology, vol. 16. pp. 151-156, (2004).
Halapi, E, "Oligoclonal T cells in human cancer", Medical Oncology, vol. 15, pp. 203-211, (1998).
Hong, H.J., "A Humanized Anti-4-1BB Monoclonal Antibody Suppresses Antigen-Induced Humoral Immune Response in Nonhuman Primates", Journal of Immunotherapy, vol. 23, pp. 613-621, (2000).
Hurtado, J. et al., "Potential Role of 4-1BB in T Cell Activation", Journal of Immunology, vol. 155, pp. 3360-3367 (1995).
Hurtado, J.C., et al., "Signals Through 4-1BB Are Costimulatory to Previously Activated Splenic T Cells and Inhibit Activation-Induced Cell Death", The American Association of Immunologists, pp. 2600-2609 (1997).
Jaffee, E.M. et al., "Novel Allogeneic Granulocyte-Macrophage Colony-Stimulating Factor-Secreting Tumor Vaccine for Pancreatic Cancer: A Phase I Trial of Safety and Immune Activation", Journal of Clinical Oncology, vol. 19, No. 1, pp. 145-156 (2001).
Jones, P. et al., "Replacing the Complementary-Determining Regions in a Human Antibody With Those From a Mouse", Nature, vol. 321, pp. 522-525 (1986).
Ju., S. et al., "A Functional Anti-Human 4-1BB Ligand Monoclonal Antibody that Enhances Proliferation of Monocytes by Reverse Signaling of 4-1BBL", Hybridoma and Hybridomincs, vol. 22, No. 5, pp. 333-338, (2003).
Kearney, J. et al., Journal of Immunology, "A New Mouse Myeloma Cell Line That Has Lost Immunoglobulin Expression But Permits the Construction of Antibody-Secreting Hybrid Cell Lines", vol. 123, No. 4, pp. 1548-1550 (1979).
Kim, J.J. et al., "Engineering Enhancement of Immune Responses to DNA-based Vaccines in a Prostate Cancer Model in Rhesus Macaques through the Use of Cytokine Gene Adjuvants", Clinical Cancer Research, vol. 7, pp. 882s-889s, (2001).
Kim, J.J. "Induction of Immune responses and safety profiles in *Rhesus macaques* immunized with a DNA vaccine expressing human prostate specific antigen", Oncogene, vol. 20, pp. 4497-4506, (2001).
Kim, J.A. et al., "Divergent Effects of 4-1BB Antibodies on Antitumor Immunity and on Tumor-reactive T-Cell Generation", Cancer Research, vol. 61; pp. 2031-2037, (2001).

Kim, N.W. et al., "Specific Association of Human Telomerase Activity with Immortal Cells and Cancer", Science, vol. 266, pp. 2011-2015 (1994).
Kim, Y. et al., Eur. J. Immunol., "Human 4-IBB Regulates CD28 Co-Stimulation to PromoteTh1 Cell Responses", vol. 28, pp. 881-890 (1998).
Kwon, B.S., et al., "cDNA sequences of two inducible T-cell genes", Proc. Natl. Acad. Sci. USA, pp. 1963-1967 (1989).
Kwon., B.S., et al., "Immune Responses in 4-1BB (CD137)-Deficient Mice", The Journal of Immunology, pp. 5483-5490 (2002).
Kwon, B. et al., Mol. Cells, "4-1BB: Still in the Midst of Darkness", vol. 10, No. 2, pp. 119-126 (2000).
Kwon, B., et al., "Involvement of tumor necrosis factor receptor superfamily (TNFRSF) members in the pathogenesis of inflammatory diseases", Experimental and Molecular Medicine, vol. 35, No. 1, pp. 8-16 (2003).
Kwon, E.D., et al., "Elimination of residual metastatic prostate cancer after surgery and adjunctive cytotoxic T lymphocyte-associated antigen 4 (CTLA-4) blockade immunotherapy", PNAS, vol. 96, pp. 15074-15079 (1999).
Laderach, D., et al., "4-1BB co-stimulation enhances human $CD8^+T$ cell priming by augmenting the proliferation and survival of effector $CD8^+T$ cells", International Immunology, vol. 14, No. 10, pp. 1155-1167 (2002).
Lane, R., "A Short-Duration Polyethylene Glycol Fusion Technique for Increasing Production of Monoclonal Antibody-Secreting Hybridomas", Journal of Immunological Methods, vol. 81, pp. 223-228 (1985).
Langstein, J., et al., "CD137 (ILA/4-1BB), a Member of the TNF Receptor Family, Induces Monocyte Activation via Bidirectional Signaling", The Journal of Immunology, vol. 160, pp. 2488-2494, (1998).
Langstein, J. et al., "Identification of CD137 as a potent monocyle survival factor", J. Leukoc. Biol., vol. 65, pp. 829-833 (1999).
Lee, H. et al., "4-1BB Promotes the Survival of $CD8^+T$ Lymphocytes by Increasing Expression of $Bcl-X_L$ and Bfl-1", The Journal of Immunology, vol. 169, pp. 4882-4888 (2002).
Lenschow, D. et al., Annu. Rev. Immunol., "CD28/B7 System of T Cell Costimulation", vol. 14, pp. 233-258 (1996).
Lesk, A: et al., Chapter 1: "Antibody Structure and Structural Predictions Useful in Guiding Antibody Engineering", Antibody Engineering, A Practical Guide, pp. 1-38 (1992).
Letvin, N.L. et al., "Heterologous Envelope Immunogens Contribute to AIDS Vaccine Protection in Rhesus Monkeys", Journal of Virology, vol. 78, No. 14, pp. 7490-7497 (2004).
Lindstedt, M, et al., Scandinavian Journal of Immunology, "Expression of CD137 (4-1BB) on Human Follicular Dendritic Cells", vol. 57, pp. 305-310 (2003).
Loh, E. et al., Science, "Polymerase Chain Reaction With Single-Sided,Specificity: Analysis of T Cell Receptor δ Chain", vol. 243, pp. 217-220 (1989).
Makitalo, B., et al., "Enhanced cellular immunity and systemic control of SHIV infection by combined parenteral and mucosal administration of a DNA prime MVA boost vaccine regimen", Journal of General Virology, vol. 85, pp. 2407-2419 (2004).
Martinet, O., et al., "T cell activation with systemic agonistic antibody versus local 4-1BB ligand gene delivery combined with interleukin-12 eradicate liver metastases of breast cancer", Gene Therapy, vol. 9, No. 12, pp. 786-792 (2002).
Maus, M., et al., "Ex vivo expansion of polyclonal and antigen-specific cytotoxic T lymphocytes by artificial APCs expressing ligands for the T-cell receptor, CD28 and 4-1BB", Nature Biotechnology, vol. 20, pp. 143-148 (2002).
Melero, I., et al., "Monoclonal antibodies against the 4-1BB T-cell activation molecule eradicate established tumors", Nature Medicine, vol. 3, No. 6, pp. 682-685 (1997).
Melero, I. et al., "NK1.1 Cells Express 4-1BB (CDw137) Costimulatory Molecule and Are Required for Tumor Immunity Elicited by Anti-4-1BB Monoclonal Antibodies", Cellular Immunology, vol. 190, pp. 167-172 (1998).
Miller, R.A., "Effect of aging on T lymphocyte activation", Vaccine, Vol, 18, pp. 1654-1660 (2000).

(56) References Cited

OTHER PUBLICATIONS

Miller, R.A., "The Aging Immune System: Primer and Prospectus", Science, vol. 273, pp. 70-74 (1996).
Miller, R.E., et al., "4-1BB-Specific Monoclonal Antibody Promotes the Generation of Tumor-Specific Immune Responses by Direct Activation of CD8 T Cells in a CD40-Dependent Manner", The Journal of immunology, vol. 169, pp. 1792-1800 (2002).
Mittler, R.S., et al., "Anti-4-1BB Monoclonal Antibodies Abrogate T Cell-dependent Humoral Immune Responses in Vivo through the Induction of Helper T Cell Anergy", J. Exp. Med., vol. 190, No. 10, pp. 1535-1540 (1999).
Mogi, S. et al., "Tumor rejection by gene transfer of 4-1BB ligand into a CD80+murine squamous cell carcinoma and the requirements of co-stimulatory molecules on tumor and host cells", Immunology, vol. 101, pp. 541-547 (2000).
Mossman, S.F., et al., "Protective Immunity to SIV Challenge Elicited by Vaccination of Macaques with Multigenic DNA Vaccines Producing Virus-Like Particles", Aids Research and Human Retroviruses, vol. 20, No. 4, pp. 425-434 (2004).
Muthumani, K., et al., "A Gag-Pol/Env-Rev SIV239 DNA vaccine improves CD4 counts, and reduce viral loads after pathogenic intrarectal $SIV_{mac}$ 251 challenge in Rhesus Macaques", Vaccine, vol. 21, pp. 629-637, pp. 629-637.
Naito, Y., et al., "$CD8^+$T Cells Infiltrated within Cancer Cell Nests as a Prognostic Favor in Human Colorectal Cancer", Cancer Research, vol. 58, pp. 3491-3494 (1998).
O'Neill, E., et al., "IL-12/GM-CSF Coadministration in an SIV DNA Prime/Protein Boost Protocol Enhances Gag-Specific T Cells But Not Virus-Specific Neutralizing Antibodies in Rhesus Macaques", Aids Research and Human Retroviruses, vol. 19, No. 10, pp. 883-890 (2003).
Pan, P. et al., "Regulation of Dendritic Cell-Funetion by NK Cells: Mechanisms Underlying the Synergism in the Combination Therapy IL-12 and 4-1BB Activation", The Journal of Immunology, vol. 172, pp. 4779-4789.
Patterson, L.J., et al., "Protection against Mucosal Simian Immunodeficiency Virus $SIV_{mac251}$ Challenge by Using Replicating Adenovirus-SIV Multigene Vaccine Priming and Subunit Boosting", Journal of Virology, vol. 78, No. 5, pp. 2212-2221(2004).
Pauly, S., et al., "CD137 is expressed by follicular dendritic cells and costimulates B lymphocyte activation in germinal centers", Journal of Leukocyte Biology, vol. 72, pp. 35-42 (2002).
Pavlenko, M., et al., "A phase I trial of DNA vaccination with a plasmid expressing prostate-specific antigen in patients with hormone-refractory prostate cancer", British Journal of Cancer, vol. 91, pp. 688-694 (2004).
Pollok, K. et al., "Inducible T Cell Antigen 4-1BB", The Journal of Immunology, vol. 150, No. 3, pp. 771-781 (1993).
Pollok, K. et al., "4-1BB T-Cell Antigen Binds to Mature B Cells and Macrophages and Costimulates Anti-µ-Primed Splenic B Cells", Eur. J. Immunol, vol. 24, pp. 367-374 (1994).
Resser, J., et al., "Immunotherapy of Head and Neck Cancer", Current Opinion in Oncology, vol. 10, pp. 226-232 (1998).
Resser, J. et al., "Immunotherapy of Head and Neck Cancer", Current Opinion in Oncology, vol. 10, pp. 226-232 (1998).
Rosenberg, S., "Interleukin-2 and the Development of Immunotherapy for the Treatment of Patients With Cancer", The Cancer Journal From Scientific American, vol. 6, pp. S2-S7 (2000).
Rosenberg, S.A., "The Identification of Cancer Antigens: Impact on the Development of Cancer Vaccines", The Cancer Journal, vol. 6, pp. S142-S144 (2000).
Rosenberg, S.A., et al., et al., "A New Era Cancer Immunotherapy Based on the Genes that Encode Cancer Antigens", Immunity, vol. 10, pp. 281-287 (1999).
Rosenberg, S.A., "Progress in human tumour immunology and immunotherapy", Nature, vol. 411, pp. 380-384 (2001).
Saiki, R. et al., "Primer-Directed Enzymatic Amplifications of DNS with a Thermostable DNA Polymerase", Science, vol. 239, pp. 487-491 (1987).
Salgia, R., et al., "Vaccination With Irradiated Antologous Tumor Cells Engineered to Secrete Granulocyte Macrophage Colony-Stimulating Factor Augments Antitumor Immunity in Some Patients With Metastatic Non-Small-Cell Lung Carcinoma", Journal of Clinical Oncology, vol. 21.
Salih, H.R., et al., "Genstitutive Expression of Functional 4-1BB (CD137) Ligand on Carcinoma Cells", The Journal of Immunology, vol. 165, pp. 2903-2910 (2000).
Salih, H.R., et al., "Soluble CD137 (4-1BB) Ligand is Released Following Leukocyte Activation and is Found in Sera of Patients with Hematological Malignancies", The Journal of Immunology, vol. 167, pp. 4059-4066 (2001).
Schwarz, H., et al., "A receptor induced by lymphocyte activation (ILA): a new member of the human nerve-growth-factor/tumor-necrosis-factor receptor family", Gene, vol. 134, No. 2, pp. 295-298 (1993).
Seo, S.K. et al., "4-1BB-mediated immunotherapy of rheumatoid arthritis", Nature Medicine, vol. 10, No. 10, pp. 1088-1094 (2004).
Shuford, W.W., et al., "4-1BB Costimulatory Signals Preferentially Induce $CD8^+$T Cell Proliferation and Lead to the Amplification in Vivo of Cytotoxic T Cell Responses", J. Ex. Med., vol. 186, No. 1, pp. 47-55 (1997).
Sun, Y. et al., "Costimulatory molecule-targeted antibody therapy of a spontaneous autoimmune disease", Nature Medicine, vol. 8, No. 12, pp. 1405-1413 (2002).
Suto, R., et al., "A Mechanism for the Specific Immunogenicity of Heat Shock Protein-Chaperoned Peptides", Science, vol. 269, pp. 1585-1583 (1995).
Takahashi, C., et al., "Cutting Edge: 4-1BB is a Bona Fide CD8 T Cell Survival Signal", The American Association of Immunologists, pp. 5037-5040 (1999).
Tamura, Y., et al., "Immunotherapy of Tumors with Autologous Tumor-Derived Heat Shock Protein Preparations", Science, vol. 278, pp. 117-120 (1997).
Tan, J.T., et al., "4-1BB Costimulation is Required for Protective Anti-Viral Immunity After Peptide Vaccination", The American Association of Immunologists, pp. 2320-2325 (2000).
van der Bruggen, P., et al., "Tumor-specific shared antigenic peptidesrecognized by human T cells", Immunological Reviews, vol. 188, pp. 51-64 (2002).
Vinay, D.S., et al., "Immunity in the absence of CD28 and CD137 (4-1BB) molecules", Immunology and Cell Biology, vol. 81, pp. 176-184 (2003).
Vinay, D.S., et al., "Role of 4-1BB in immune responses", Immunology, vol. 10, pp. 481-489, (1998).
Wan, Y., et al., "Expression of co-stimulator 4-1BB molecule in hepatocellular carcinoma and adjacent non-tumor liver tissue, and its possible role in tumor immunity", World J. Gastroenteol, vol. 10, No. 2, pp. 195-199 (2004).
Wen, T., et al., "4-1BB Ligand-Mediated Costimulation of Human T. Cells Induces CD4 and CD8 T Cell Expansion, Cytokine Production, and the Development of Cytolytic Effector Function", Journal of Immunology, vol. 168, pp. 4897-4906 (2002).
Wilcox, R.A., et al., "Impaired Infiltration of Tumor-specific Cytolytic T Cells in the Absence of Interferon-v despite Their Normal Maturation in Lymphoid Organs during CD137 Monoclonal Antibody Therapy", Cancer Research, vol. 62, pp. 4413-4418 (2002).
Wilcox, R., et al., "Cutting Edge: Expression of Functional CD137 Receptor by Dendritic Cells", Journal of Immunology, vol. 168, pp. 4262-4267 (2002).
Wilcox, R.A., et al., "Signaling Through NK Cell-Associated CD137 Promotes Both Helper Function for $CD8^+$Cytolytic T Cells and Responsiveness to IL-2 But Not Cytolytic Activity[1]", The Journal of Immunology, vol. 169, pp. 4230-4236 (2002).
Wolchok, J.D., et al., "DNA Vaccines: An Active Immunization Strategy for Prostate Cancer", Seminars in Oncology, vol. 30, No. 5, pp. 659-666 (2003).
Zhang, H., et al., "Tumor Expression of 4-1BB Ligand Sustains Tumor Lytic T Cells", Cancer Biology & Therapy, vol. 2, No. 5, pp. 579-586 (2003).
Zhang, L., et al., "Intratumoral T Cells, Recurrence, and Survival in Epithelial Ovarian Cancer", The New England Journal of Medicine, vol. 348, pp. 203-213 (2003).

(56) References Cited

OTHER PUBLICATIONS

Zhou, Z., et al., "Characterization of human homologue of 4-1BB and its ligand", Immunology Letters, vol. 45, pp. 67-73 (1995).
Loo, D.T. et al., "Analysis of 4-1BBL and Laminin Binding to Murine 4-1BB, a Member of the Tumor Necrosis Factor Receptor Superfamily, and Comparison with Human 4-1BB", The Journal of Biological Chemistry, vol. 272, No. 10, pp. 6448-6456, Mar. 7, 1997.
Ye Zhengmao et al., "Gene Therapy for Cancer Using Single-Chain Fv Fragments Specific for 4-1BB", Nature Medicine, vol. 8, No. 4, pp. 343-348, Apr. 4, 2002.
Lee et al., Advances in Experimental Medicine and Biology, 2009, 647: 120-129.
Palma et al., Int. J. Cancer, 2004, 108: 390-398.
Kim et al., Immunology, 2002, 107: 472-479.
Boon et al., Annu. Rev. Immunol., 2006, 24: 175-208.
Nielsen et al., 2000, Cancer Chemother. Pharmacol., 46 (Suppl.): S62-S66.
Lee et al., 1999, J. Immunol., 163: 6292-6300.
Blazer et al., J. Immunol., 1996, 157: 3250-3259.
Phase II, 2nd Line Melanoma—RAND Monotherapy—ClinicalTrials.gov, 2011, 4 pages.

* cited by examiner

```
  1   CGATGTACGG GCCAGATATA CGCCGTGACA TTGATTATTG ACTAGTTATT
      GCTACATGCC CGGTCTATAT GCGGCACTGT AACTAATAAC TGATCAATAA
 51   AATAGTAATC AATTACGGGG TCATTAGTTC ATAGCCCATA TATGGAGTTC
      TTATCATTAG TTAATGCCCC AGTAATCAAG TATCGGGTAT ATACCTCAAG
101   CGCGTTACAT AACTTACGGT AAATGGCCCG CCTGGCTGAC CGCCCAACGA
      GCGCAATGTA TTGAATGCCA TTTACCGGGC GGACCGACTG GCGGGTTGCT
151   CCCCCGCCCA TTGACCTCAA TAATGACGTA TGTTCCCATA GTAACGCCAA
      GGGGGCGGGT AACTGGAGTT ATTACTGCAT ACAAGGGTAT CATTGCCGTT
201   TAGGGACTTT CCATTGACGT CAATGGGTGG AGTATTTACG GTAAACTGCC
      ATCCCTGAAA GGTAACTGCA GTTACCCACC TGATAAATGC CATTTGACGG
251   CACTTGGCAG TACATCAAGT GTATCATATG CCAAGTACGC CCCCTATTGA
      GTGAACCGTC ATGTAGTTCA CATAGTATAC GGTTCATGCG GGGGATAACT
301   CGTCAATGAC GGTAAATGGC CCGCCTGGCA TTATGCCCAG TACATGACCT
      GCAGTTACTG CCATTTACCG GGCGGACCGT AATACGGGTC ATGTACTGGA
351   TATGGACTTT CCTACTTGG  CAGTACATCT ACGTATTAGT CATCGCTATT
      ATACCTGAA  AGGATGAACC GTCATGTAGA TGCATAATCA GTAGCGATAA
401   ACCATGGTGA TGCGGTTTTG GCAGTACATC AATGGGCGTG GATAGCGGTT
      TGGTACCACT ACGCCAAAAC CGTCATGTAG TTACCCGCAC CTATCGCCAA
451   TGACTCACGG GGATTTCCAA GTCTCCACCC CATTGACGTC AATGGGAGTT
      ACTGAGTGCC CCTAAAGGTT CAGAGGTGGG GTAACTGCAG TTACCCTCAA
501   TGTTTTGGCA CCAAAATCAA CGGGACTTTC CAAAATGTCG TAACAACTCC
      ACAAAACCGT GGTTTTAGTT GCCCTGAAAG GTTTACAGC  ATTGTTGAGG
551   GCCCCATTGA CGCAAATGGG CGGTAGGCGT GTACGGTGGG AGGTCTATAT
      CGGGGTAACT GCGTTTACCC GCCATCCGCA CATGCCACCC TCCAGATATA
601   AAGCAGAGCT CTCTGGCTAA CTAGAGAACC CACTGCTTAC TGGCTTATCG
      TTCGTCTCGA GAGACCGATT GATCTCTTGG GTGACGAATG ACCGAATAGC
                                                           M  K  ·
651   AAATTAATAC GACTCACTAT AGGGAGACCC AAGCTTGGTA CCGCCATGAA
      TTTAATTATG CTGAGTGATA TCCCTCTGGG TTCGAACCAT GGCGGTACTT
                                          natural Ig leader peptide
      ~~~~~~~~~~~~~~~~~~~~~~~~~~~~~~~~~~~~~~~~~~~~~~~~~~~
       ·  H   L   W   F   F   L   L   V   A   P   R   W   V   L   S  ·
701   ACACCTGTGG TTCTTCCTCC TCCTGGTGGC AGCTCCAGA TGGGTCCTGT
      TGTGGACACC AAGAAGGAGG AGGACCACCG TCGAGGTCT ACCCAGGACA
      natural Ig leader sequence
      ~~
                     2CH4-9 HC variable region
      ~~~~~~~~~~~~~~~~~~~~~~~~~~~~~~~~~~~~~~~~~~~~~~~~~~~
       ·  Q   V   Q   L   Q   Q   W   G   A   G   L   L   K   P   S   E
751   CCCAGGTGCA ACTACAGCAG TGGGGCGCAG GACTGTTGAA GCCTTCGGAG
      GGGTCCACGT TGATGTCGTC ACCCCGCGTC CTGACAACTT CGGAAGCCTC
                                                          CDR 1
                                                       ~~~~~~~~~~
                     2CH4-9 HC variable region
      ~~~~~~~~~~~~~~~~~~~~~~~~~~~~~~~~~~~~~~~~~~~~~~~~~~~
           T   L   S   L   T   C   A   V   Y   G   G   S   F   S   G   Y   Y  ·
801   ACCCTGTCCC TCACCTGCGC TGTCTATGGT GGGTCCTTCA GTGGTTACTA
      TGGGACAGGG AGTGGACGCG ACAGATACCA CCCAGGAAGT CACCAATGAT
           CDR 1                                                    CDR 2
      ~~~~~~~~                                                 ~~~~~~~~~~
                     2CH4-9 HC variable region
      ~~~~~~~~~~~~~~~~~~~~~~~~~~~~~~~~~~~~~~~~~~~~~~~~~~~
       ·  W   S   W   I   R   Q   S   P   E   K   G   L   E   W   I   G  ·
851   CTGGAGCTGG ATACGCCAGT CCCCAGAGAA GGGGCTGGAG TGGATTGGGG
      GACCTCGACC TATGCGGTCA GGGGTCTCTT CCCCGACCTC ACCTAACCCC
```

FIG. 3A

```
                                      CDR 2
                        ~~~~~~~~~~~~~~~~~~~~~~~~~~~~~~~~~~~~~~~~~~~~
                                2084-9 HC variable region
                        ~~~~~~~~~~~~~~~~~~~~~~~~~~~~~~~~~~~~~~~~~~~~
              ·  I   N   R    G   G   Y    V   T   Y   N    P   S   L    E   S   R
       901    AAATCAATCA  TGGTGGATAC  GTCACCTACA  ATCCGTCCCT  CGAGAGTCGA
              TTTAGTTAGT  ACCACCTATG  CAGTGGATGT  TAGGCAGGGA  GCTCTCAGCT
                                2084-9 HC variable region
                        ~~~~~~~~~~~~~~~~~~~~~~~~~~~~~~~~~~~~~~~~~~~~
                 V   T   I   S    V   D   T    S   K   N    Q   F   S   L    K   L   S ·
       951    GTCACCATAT  CAGTAGACAC  GTCCAAGAAC  CAGTTCTCCC  TGAAGCTGAG
              CAGTGGTATA  GTCATCTGTG  CAGGTTCTTG  GTCAAGAGGG  ACTTCGACTC
                                                                          CDR 3
                                                                     ~~~~~~~~~~~~~
                                2084-9 HC variable region
                        ~~~~~~~~~~~~~~~~~~~~~~~~~~~~~~~~~~~~~~~~~~~~
              ·  S   V   T    A   A   D    T   A   V   Y    Y   C   A    R   D   Y   G ·
      1001    CTCTGTGACC  GCCGCGGACA  CGGCTGTATA  TTACTGTGCG  AGGGACTATG
              GAGACACTGG  CGGCGCCTGT  GCCGACATAT  AATGACACGC  TCCCTGATAC
                   CDR 3
              ~~~~~~~~~~~~~~~~~~~~~~~~~~~~~~~~~~
                                2084-9 HC variable region
                        ~~~~~~~~~~~~~~~~~~~~~~~~~~~~~~~~~~~~~~~~~~~~
              ·  P   G   N    Y   D   W    Y   F   D   L    W   G   R    G   T   L
      1051    GTCCCGGGAA  TTATGACTGG  TACTTCGATC  TCTGGGGCCG  TGGCACCCTG
              CAGGGCCCTT  AATACTGACC  ATGAAGCTAG  AGACCCCGGC  ACCGTGGGAC
                                                                  IgG4 CH1 domain
                                                           ~~~~~~~~~~~~~~~~~~~~~~~~~~~
              2084-9 HC variable region
              ~~~~~~~~~~~~~~~~~~~~~~
                 V   T   V   S    S   A   S    T   K   G    P   S   V    F   P   L   A ·
      1101    GTCACTGTCT  CCTCAGCTAG  CACCAAGGGC  CCATCCGTCT  TCCCCCTGGC
              CAGTGACAGA  GGAGTCGATC  GTGGTTCCCG  GGTAGGCAGA  AGGGGGACCG
                                   IgG4 CH1 domain
                        ~~~~~~~~~~~~~~~~~~~~~~~~~~~~~~~~~~~~~~~~~~~~
              ·  P   C   S    R   S   T    S   E   S   T    A   A   L    G   C   L   V ·
      1151    GCCCTGCTCC  AGGAGCACCT  CCGAGAGCAC  AGCCGCCCTG  GGCTGCCTGG
              CGGGACGAGG  TCCTCGTGGA  GGCTCTCGTG  TCGGCGGGAC  CCGACGGACC
                                   IgG4 CH1 domain
                        ~~~~~~~~~~~~~~~~~~~~~~~~~~~~~~~~~~~~~~~~~~~~
              ·  K   D   Y    F   P   E    P   V   T   V    S   W   N    S   G   A
      1201    TCAAGGACTA  CTTCCCCGAA  CCGGTGACGG  TGTCGTGGAA  CTCAGGCGCC
              AGTTCCTGAT  GAAGGGGCTT  GGCCACTGCC  ACAGCACCTT  GAGTCCGCGG
                                   IgG4 CH1 domain
                        ~~~~~~~~~~~~~~~~~~~~~~~~~~~~~~~~~~~~~~~~~~~~
                 L   T   S   G    V   H   T    F   P   A    V   L   Q    S   S   G   L ·
      1251    CTGACCAGCG  GCGTGCACAC  CTTCCCGGCT  GTCCTACAGT  CCTCAGGACT
              GACTGGTCGC  CGCACGTGTG  GAAGGGCCGA  CAGGATGTCA  GGAGTCCTGA
                                   IgG4 CH1 domain
                        ~~~~~~~~~~~~~~~~~~~~~~~~~~~~~~~~~~~~~~~~~~~~
              ·  Y   S   L    S   S   V    V   T   V   P    S   S   S    L   G   T   K ·
      1301    CTACTCCCTC  AGCAGCGTGG  TGACCGTGCC  CTCCAGCAGC  TTGGGCACGA
              GATGAGGGAG  TCGTCGCACC  ACTGGCACGG  GAGGTCGTCG  AACCCGTGCT
```

FIG. 3B

```
                              IgG4 CH1 domain
           -------------------------------------------------
               · T  Y  T  C  N  V  D  H  K  P  S  N  T  K  V  D ·
      1351   AGACCTACAC CTGCAACGTA GATCACAAGC CCAGCAACAC CAAGGTGGAC
             TCTGGATGTG GACGTTGCAT CTAGTGTTCG GGTCGTTGTG GTTCCACCTG
                              IgG4 hinge region
           -------------------------------------------------

IgG4 CH1 domain
           ------------
               K  R  V  E  S  K  Y  G  P  P  C  P  P  C  P  A  P ·
      1401   AAGAGAGTTG AGTCCAAATA TGGTCCACCT TGCCCACCTT GCCCAGCACC
             TTCTCTCAAC TCAGGTTTAT ACCAGGTGGA ACGGGTGGAA CGGGTCGTGG
                              IgG4 CH2 domain
           -------------------------------------------------
               · E  F  L  G  G  P  S  V  F  L  F  P  P  K  P  K  D ·
      1451   TGAGTTCCTG GGGGGACCAT CAGTCTTCCT GTTCCCCCCA AAACCCAAGG
             ACTCAAGGAC CCCCCTGGTA GTCAGAAGGA CAAGGGGGGT TTTGGGTTCC
                              IgG4 CH2 domain
           -------------------------------------------------
               · T  L  M  I  S  R  T  P  E  V  T  C  V  V  V  D ·
      1501   ACACTCTCAT GATCTCCCGG ACCCCTGAGG TCACGTGCGT GGTGGTGGAC
             TGTGAGAGTA CTAGAGGGCC TGGGGACTCC AGTGCACGCA CCACCACCTG
                              IgG4 CH2 domain
           -------------------------------------------------
                  V  S  Q  E  D  P  E  V  Q  F  N  W  Y  V  D  G  V ·
      1551   GTGAGCCAGG AAGACCCCGA GGTCCAGTTC AACTGGTACG TGGATGGCGT
             CACTCGGTCC TTCTGGGGCT CCAGGTCAAG TTGACCATGC ACCTACCGCA
                              IgG4 CH2 domain
           -------------------------------------------------
               · E  V  H  N  A  K  T  K  P  R  E  E  Q  F  N  S  T ·
      1601   GGAGGTGCAT AATGCCAAGA CAAAGCCGCG GGAGGAGCAG TTCAACAGCA
             CCTCCACGTA TTACGGTTCT GTTTCGGCGC CCTCCTCGTC AAGTTGTCGT
                              IgG4 CH2 domain
           -------------------------------------------------
               · Y  R  V  V  S  V  L  T  V  L  H  Q  D  W  L  N ·
      1651   CGTACCGTGT GGTCAGCGTC CTCACCGTCC TGCACCAGGA CTGGCTGAAC
             GCATGGCACA CCAGTCGCAG GAGTGGCAGG ACGTGGTCCT GACCGACTTG
                              IgG4 CH2 domain
           -------------------------------------------------
                  G  K  E  Y  K  C  K  V  S  N  K  G  L  P  S  S  I ·
      1701   GGCAAGGAGT ACAAGTGCAA GGTCTCCAAC AAAGGCCTCC CGTCCTCCAT
             CCGTTCCTCA TGTTCACGTT CCAGAGGTTG TTTCCGGAGG GCAGGAGGTA
                                           IgG4 CH3 domain
                                        -------------------------

IgG4 CH2 domain
           -------------------------------------------------
               · E  K  T  I  S  K  A  K  G  Q  P  R  E  P  Q  V  Y ·
      1751   CGAGAAAACC ATCTCCAAAG CCAAAGGGCA GCCCCGAGAG CCACAGGTGT
             GCTCTTTTGG TAGAGGTTTC GGTTTCCCGT CGGGGCTCTC GGTGTCCACA
                              IgG4 CH3 domain
           -------------------------------------------------
               · T  L  P  P  S  Q  E  E  M  T  K  N  Q  V  S  L ·
      1801   ACACCCTGCC CCCATCCCAG GAGGAGATGA CCAAGAACCA GGTCAGCCTG
             TGTGGGACGG GGGTAGGGTC CTCCTCTACT GGTTCTTGGT CCAGTCGGAC
```

FIG. 3C

```
                          IgG4 CH3 domain
       ~~~~~~~~~~~~~~~~~~~~~~~~~~~~~~~~~~~~~~~~~~~~~~~~~~~~~~~~~~~~~
           T  C  L  V  K  G  F  Y  P  S  D  I  A  V  E  W  E ·
 1851  ACCTGCCTGG TCAAGGGCTT CTACCCCAGC GACATCGCCG TGGAGTGGGA
       TGGACGGACC AGTTCCCGAA GATGGGGTCG CTGTAGCGGC ACCTCACCCT
                          IgG4 CH3 domain
       ~~~~~~~~~~~~~~~~~~~~~~~~~~~~~~~~~~~~~~~~~~~~~~~~~~~~~~~~~~~~~
       ·  S  N  G  Q  P  E  N  N  Y  K  T  T  P  P  V  L  D ·
 1901  GAGCAATGGG CAGCCGGAGA ACAACTACAA GACCACGCCT CCCGTGCTGG
       CTCGTTACCC GTCGGCCTCT TGTTGATGTT CTGGTGCGGA GGGCACGACC
                          IgG4 CH3 domain
       ~~~~~~~~~~~~~~~~~~~~~~~~~~~~~~~~~~~~~~~~~~~~~~~~~~~~~~~~~~~~~
       ·  S  D  G  S  F  F  L  Y  S  R  L  T  V  D  K  S
 1951  ACTCCGACGG CTCCTTCTTC CTCTACAGCA GGCTAACCGT GGACAAGAGC
       TGAGGCTGCC GAGGAAGAAG GAGATGTCGT CCGATTGGCA CCTGTTCTCG
                          IgG4 CH3 domain
       ~~~~~~~~~~~~~~~~~~~~~~~~~~~~~~~~~~~~~~~~~~~~~~~~~~~~~~~~~~~~~
           R  W  Q  E  G  N  V  F  S  C  S  V  M  H  E  A  L ·
 2001  AGGTGGCAGG AGGGGAATGT CTTCTCATGC TCCGTGATGC ATGAGGCTCT
       TCCACCGTCC TCCCCTTACA GAAGAGTACG AGGCACTACG TACTCCGAGA
                          IgG4 CH3 domain
       ~~~~~~~~~~~~~~~~~~~~~~~~~~~~~~~~~~~~~~~~~~~~~~~~~~~~~~~~~~~~~
       ·  H  N  H  Y  T  Q  K  S  L  S  L  S  L  G  K
 2051  GCACAACCAC TACACACAGA AGAGCCTCTC CCTGTCTCTG GGTAAATGAT
       CGTGTTGGTG ATGTGTGTCT TCTCGGAGAG GGACAGAGAC CCATTTACTA
 2101  CTAGAGGGCC CTATTCTATA GTGTCACCTA AATGCTAGAG CTCGCTGATC
       GATCTCCCGG GATAAGATAT CACAGTGGAT TTACGATCTC GAGCGACTAG
 2151  AGCCTCGACT GTGCCTTCTA GTTGCCAGCC ATCTGTTGTT TGCCCCTCCC
       TCGGAGCTGA CACGGAAGAT CAACGGTCGG TAGACAACAA ACGGGGAGGG
 2201  CCGTGCCTTC CTTGACCCTG GAAGGTGCCA CTCCCACTGT CCTTTCCTAA
       GGCACGGAAG GAACTGGGAC CTTCCACGGT GAGGGTGACA GGAAAGGATT
 2251  TAAAATGAGG AAATTGCATC GCATTGTCTG AGTAGGTGTC ATTCTATTCT
       ATTTTACTCC TTTAACGTAG CGTAACAGAC TCATCCACAG TAAGATAAGA
 2301  GGGGGGTGGG GTGGGCAGG ACAGCAAGGG GGAGGATTG GAAGACAATA
       CCCCCCACCC CACCCCGTCC TGTCGTTCCC CCTCCTAACC CTTCTGTTAT
 2351  GCAGGCATGC TGGGGATGCG GTGGGCTCTA TGGCTTCTGA GGCGGAAAGA
       CGTCCGTACG ACCCCTACGC CACCCGAGAT ACCGAAGACT CCGCCTTTCT
 2401  ACCAGCTGGG GCTCTAGGGG GTATCCCCAC GCGCCCTGTA GCGGCGCATT
       TGGTCGACCC CGAGATCCCC CATAGGGGTG CGCGGGACAT CGCCGCGTAA
 2451  AAGCGCGGCG GGTGTGGTGG TTACGCGCAG CGTGACCGCT ACACTTGCCA
       TTCGCGCCGC CCACACCACC AATGCGCGTC GCACTGGCGA TGTGAACGGT
 2501  GCGCCCTAGC GCCCGCTCCT TTCGCTTTCT TCCCTTCCTT TCTCGCCACG
       CGCGGGATCG CGGGCGAGGA AAGCGAAAGA AGGGAAGGAA AGAGCGGTGC
 2551  TTCGCCGGGC TCTCAAAAA AGGGAAAAAA AGCATGCATC TCAATTAGTC
       AAGCGGCCCG GAGAGTTTTT TCCCTTTTTT TCGTACGTAG AGTTAATCAG
 2601  AGCAACCATA GTCCCGCCCC TAACTCCGCC CATCCCGCCC CTAACTCCGC
       TCGTTGGTAT CAGGGCGGGG ATTGAGGCGG GTAGGGCGGG GATTGAGGCG
 2651  CCAGTTCCGC CCATTCTCCG CCCCATGGCT GACTAATTTT TTTATTTAT
       GGTCAAGGCG GGTAAGAGGC GGGGTACCGA CTGATTAAAA AAAATAAATA
 2701  GCAGAGGCCG AGGCCGCCTC GGCCTCTGAG CTATTCCAGA AGTAGTGAGG
       CGTCTCCGGC TCCGGCGGAG CCGGAGACTC GATAAGGTCT TCATCACTCC
 2751  AGGCTTTTTT GGAGGCCTAG GCTTTTGCAA AAAGCTTGGA CAGCTCAGGG
       TCCGAAAAAA CCTCCGGATC CGAAAACGTT TTTCGAACCT GTCGAGTCCC
 2801  CTGCGATTTC GCGCCAAACT TGACGGCAAT CCTAGCGTGA AGGCTGGTAG
       GACGCTAAAG CGCGGTTTGA ACTGCCGTTA GGATCGCACT TCCGACCATC
```

```
5601  TTCTACGGGG  TCTGACGCTC  AGTGGAACGA  AAACTCACGT  TAAGGGATTT
      AAGATGCCCC  AGACTGCGAG  TCACCTTGCT  TTTGAGTGCA  ATTCCCTAAA
5651  TGGTCATGAG  ATTATCAAAA  AGGATCTTCA  CCTAGATCCT  TTAAATTAA
      ACCAGTACTC  TAATAGTTTT  TCCTAGAAGT  GGATCTAGGA  AAATTTAATT
5701  AAATGAAGTT  TTAAATCAAT  CTAAAGTATA  TATGAGTAAA  CTTGGTCTGA
      TTTACTTCAA  AATTTAGTTA  GATTTCATAT  ATACTCATTT  GAACCAGACT
5751  CAGTTACCAA  TGCTTAATCA  GTGAGGCACC  TATCTCAGCG  ATCTGTCTAT
      GTCAATGGTT  ACGAATTAGT  CACTCCGTGG  ATAGAGTCGC  TAGACAGATA
5801  TTCGTCATC   CATAGTTGCC  TGACTCCCCG  TCGTGTAGAT  AACTACGATA
      AAGCAAGTAG  GTATCAACGG  ACTGAGGGGC  AGCACATCTA  TTGATGCTAT
5851  CGGGAGGGCT  TACCATCTGG  CCCCAGTGCT  GCAATGATAC  CGCGAGACCC
      GCCCTCCCGA  ATGGTAGACC  GGGGTCACGA  CGTTACTATG  GCGCTCTGGG
5901  ACGCTCACCG  GCTCCAGATT  TATCAGCAAT  AAACCAGCCA  GCCGGAAGGG
      TGCGAGTGGC  CGAGGTCTAA  ATAGTCGTTA  TTTGGTCGGT  CGGCCTTCCC
5951  CCGAGCGCAG  AAGTGGTCCT  GCAACTTTAT  CCGCCTCCAT  CCAGTCTATT
      GGCTCGCGTC  TTCACCAGGA  CGTTGAAATA  GGCGGAGGTA  GGTCAGATAA
6001  AATTGTTGCC  GGGAAGCTAG  AGTAAGTAGT  TCGCCAGTTA  ATAGTTTGCG
      TTAACAACGG  CCCTTCGATC  TCATTCATCA  AGCGGTCAAT  TATCAAACGC
6051  CAACGTTGTT  GCCATTGCTA  CAGGCATCGT  GGTGTCACGC  TCGTCGTTTG
      GTTGCAACAA  CGGTAACGAT  GTCCGTAGCA  CCACAGTGCG  AGCAGCAAAC
6101  GTATGGCTTC  ATTCAGCTCC  GGTTCCCAAC  GATCAAGGCG  AGTTACATGA
      CATACCGAAG  TAAGTCGAGG  CCAAGGGTTG  CTAGTTCCGC  TCAATGTACT
6151  TCCCCCATGT  TGTGCAAAAA  AGCGGTTAGC  TCCTTCGGTC  CTCCGATCGT
      AGGGGGTACA  ACACGTTTTT  TCGCCAATCG  AGGAAGCCAG  GAGGCTAGCA
6201  TGTCAGAAGT  AAGTTGGCCG  CAGTGTTATC  ACTCATGGTT  ATGGCAGCAC
      ACAGTCTTCA  TTCAACCGGC  GTCACAATAG  TGAGTACCAA  TACCGTCGTG
6251  TGCATAATTC  TCTTACTGTC  ATGCCATCCG  TAAGATGCTT  TTCTGTGACT
      ACGTATTAAG  AGAATGACAG  TACGGTAGGC  ATTCTACGAA  AAGACACTGA
6301  GGTGAGTACT  CAACCAAGTC  ATTCTGAGAA  TAGTGTATGC  GGCGACCGAG
      CCACTCATGA  GTTGGTTCAG  TAAGACTCTT  ATCACATACG  CCGCTGGCTC
6351  TTCCTCTTGC  CCGGCGTCAA  TACGGGATAA  TACCGCGCCA  CATAGCAGAA
      AAGGAGAACG  GGCCGCAGTT  ATGCCCTATT  ATGGCGCGGT  GTATCGTCTT
6401  CTTTAAAAGT  GCTCATCATT  GGAAAACGTT  CTTCGGGGCG  AAAACTCTCA
      GAAATTTTCA  CGAGTAGTAA  CCTTTTGCAA  GAAGCCCCGC  TTTTGAGAGT
6451  AGGATCTTAC  CGCTGTTGAG  ATCCAGTTCG  ATGTAACCCA  CTCGTGCACC
      TCCTAGAATG  GCGACAACTC  TAGGTCAAGC  TACATTGGGT  GAGCACGTGG
6501  CAACTGATCT  TCAGCATCTT  TTACTTTCAC  CAGCGTTTCT  GGGTGAGCAA
      GTTGACTAGA  AGTCGTAGAA  AATGAAAGTG  GTCGCAAAGA  CCCACTCGTT
6551  AAACAGGAAG  GCAAAATGCC  GCAAAAAAGG  GAATAAGGGC  GACACGGAAA
      TTTGTCCTTC  CGTTTTACGG  CGTTTTTTCC  CTTATTCCCG  CTGTGCCTTT
6601  TGTTGAATAC  TCATACTCTT  CCTTTTTCAA  TATTATTGAA  GCATTTATCA
      ACAACTTATG  AGTATGAGAA  GGAAAAAGTT  ATAATAACTT  CGTAAATAGT
6651  GGTTATTGT   CTCATGAGCG  GATACATATT  TGAATGTATT  TAGAAAAATA
      CCAATAACA   GAGTACTCGC  CTATGTATAA  ACTTACATAA  ATCTTTTTAT
6701  AACAAATAGG  GGTTCCGCGC  ACATTTCCCC  GAAAAGTGCC  ACCTGACGTC
      TTGTTTATCC  CCAAGGCGCG  TGTAAAGGGG  CTTTTCACGG  TGGACTGCAG
6751  GACGGATCG   GAGATCTGCT  AGGTGACCTG  AGGCGCGCCG  GCTTCGAATA
      CTGCCTAGCC  CTCTAGACGA  TCCACTGGAC  TCCGCGCGGC  CGAAGCTTAT
6801  GCCAGAGTAA  CCTTTTTTTT  TAATTTATT   TTATTTTATT  TTGAGATGG
      CGGTCTCATT  GGAAAAAAAA  ATTAAATAA   AATAAAATAA  AACTCTACC
6851  AGTTTGGCGC  CGATCCCCG   ATCCCTATG   GTCGACTCTC  AGTACAATCT
      TCAAACCGCG  GCTAGGGGC   TAGGGATAC   CAGCTGAGAG  TCATGTTAGA
6901  GCTCTGATGC  CGCATAGTTA  AGCCAGTATC  TGCTCCCTGC  TTGTGTGTTG
      CGAGACTACG  GCGTATCAAT  TCGGTCATAG  ACGAGGGACG  AACACACAAC
6951  GAGGTCGCTG  AGTAGTGCGC  GAGCAAAATT  TAAGCTACAA  CAAGGCAAGG
```

FIG. 3G

```
      CTCCAGCGAC TCATCACGCG CTCGTTTTAA ATTCGATGTT GTTCCGTTCC
7001  CTTGACCGAC AATTGCATGA AGAATCTGCT TAGGGTTAGG CGTTTTGCGC
      GAACTGGCTG TTAACGTACT TCTTAGACGA ATCCCAATCC GCAAAACGCG
7051  TGCTTCG
      ACGAAGC
```

FIG. 3H

```
  1  GACGGATCGG GAGATCTGCT AGCCCGGGTG ACCTGAGGCG CGCCGGCTTC
     CTGCCTAGCC CTCTAGACGA TCGGGCCCAC TGGACTCCGC GCGGCCGAAG
 51  GAATAGCCAG AGTAACCTTT TTTTTTAATT TTATTTTATT TTATTTTTGA
     CTTATCGGTC TCATTGGAAA AAAAAATTAA AATAAAATAA AATAAAAACT
101  GATGGAGTTT GGGGCCCATC TCCCGATCCC CTATGGTCGA CTCTCAGTAC
     CTACCTCAAA CCCCGGGTAG AGGGCTAGGG GATACCAGCT GAGAGTCATG
151  AATCTGCTCT GATGCCGCAT AGTTAAGCCA GTATCTGCTC CCTGCTTGTG
     TTAGACGAGA CTACGGCGTA TCAATTCGGT CATAGACGAG GGACGAACAC
201  TGTTGGAGGT CGCTGAGTAG TGCGCGAGCA AAATTTAAGC TACAACAAGG
     ACAACCTCCA GCGACTCATC ACGCGCTCGT TTTAAATTCG ATGTTGTTCC
251  CAAGGCTTGA CCGACAATTG CATGAAGAAT CTGCTTAGGG TTAGGCGTTT
     GTTCCGAACT GGCTGTTAAC GTACTTCTTA GACGAATCCC AATCCGCAAA
301  TGCGCTGCTT CGCGATGTAC GGGCCAGATA TACGCGTTGA CATTGATTAT
     ACGCGACGAA GCGCTACATG CCCGGTCTAT ATGCGCAACT GTAACTAATA
351  TGACTAGTTA TTAATAGTAA TCAATTACGG GGTCATTAGT TCATAGCCCA
     ACTGATCAAT AATTATCATT AGTTAATGCC CCAGTAATCA AGTATCGGGT
401  TATATGGAGT TCCGCGTTAC ATAACTTACG GTAAATGGCC CGCCTGGCTG
     ATATACCTCA AGGCGCAATG TATTGAATGC CATTTACCGG GCGGACCGAC
451  ACCGCCCAAC GACCCCCGCC CATTGACGTC AATAATGACG TATGTTCCCA
     TGGCGGGTTG CTGGGGGCGG GTAACTGCAG TTATTACTGC ATACAAGGGT
501  TAGTAACGCC AATAGGGACT TTCCATTGAC GTCAATGGGT GGAGTATTTA
     ATCATTGCGG TTATCCCTGA AAGGTAACTG CAGTTACCCA CCTCATAAAT
551  CGGTAAACTG CCCACTTGGC AGTACATCAA GTGTATCATA TGCCAAGTAC
     GCCATTTGAC GGGTGAACCG TCATGTAGTT CACATAGTAT ACGGTTCATG
601  GCCCCCTATT GACGTCAATG ACGGTAAATG GCCCGCCTGG CATTATGCCC
     CGGGGGATAA CTGCAGTTAC TGCCATTTAC CGGGCGGACC GTAATACGGG
651  AGTACATGAC CTTATGGGAC TTTCCTACTT GGCAGTACAT CTACGTATTA
     TCATGTACTG GAATACCCTG AAAGGATGAA CCGTCATGTA GATGCATAAT
701  GTCATCGCTA TTACCATGGT GATGCGGTTT TGGCAGTACA TCAATGGGCG
     CAGTAGCGAT AATGGTACCA CTACGCCAAA ACCGTCATGT AGTTACCCGC
751  TGGATAGCGG TTTGACTCAC GGGGATTTCC AAGTCTCCAC CCCATTGACG
     ACCTATCGCC AAACTGAGTG CCCCTAAAGG TTCAGAGGTG GGGTAACTGC
801  TCAATGGGAG TTTGTTTTGG CACCAAAATC AACGGGACTT TCCAAAATGT
     AGTTACCCTC AAACAAAACC GTGGTTTTAG TTGCCCTGAA AGGTTTTACA
851  CGTAACAACT CCGCCCCATT GACGCAAATG GGCGGTAGGC GTGTACGGTG
     GCATTGTTGA GGCGGGGTAA CTGCGTTTAC CCGCCATCCG CACATGCCAC
901  GGAGGTCTAT ATAAGCAGAG CTCTCTGGCT AACTAGAGAA CCCACTGCTT
     CCTCCAGATA TATTCGTCTC GAGAGACCGA TTGATCTCTT GGGTGACGAA
951  ACTGGCTTAT CGAAATTAAT ACGACTCACT ATAGGGAGAC CCAAGCTTAT
     TGACCGAATA GCTTTAATTA TGCTGAGTGA TATCCCTCTG GGTTCGAATA
                                                Natural Ig leader
                                              ---------------------
                                                 M  E  A  P  A  Q ·
1001 CAACAAGTTT GTACAAAAAA GCAGGCTGGT ACCATGGAAG CCCCAGCTCA
     GTTGTTCAAA CATGTTTTTT CGTCCGACCA TGGTACCTTC GGGGTCGAGT Natural Ig leader peptide
     ----------------------------------------
     ·  L  L  F  L  L  L  W  L  P  D  T  G  E  I  V ·
1051 GCTTCTCTTC CTCCTGCTAC TCTGGCTCCC AGATACCACC GGAGAAATTG
     CGAAGAGAAG GAGGACGATG AGACCGAGGG TCTATGGTGG CCTCTTTAAC
```

FIG. 4A 2084-9 LC variable region

```
              . L  T  Q   S  P  A   T  L  S   L  S  P   G  E  R   A
      1101    TGTTGACACA GTCTCCAGCC ACCCTGTCTT TGTCTCCAGG GGAAAGAGCC
              ACAACTGTGT CAGAGGTCGG TGGGACAGAA ACAGAGGTCC CCTTTCTCGG
```

2084-9 LC variable region

CDR 1

```
              T  L  S   C  R  A  S   Q  S  V   S  S  Y   L  A  W   Y.
      1151    ACCCTCTCCT GCAGGGCCAG TCAGAGTGTT AGCAGCTACT TAGCCTGGTA
              TGGGAGAGGA CGTCCCGGTC AGTCTCACAA TCGTCGATGA ATCGGACCAT
```

2084-9 LC variable region

CDR 2

```
              . Q  Q  K   P  G  Q   A  P  R   L  L  I   Y  D  A   S N.
      1201    CCAACAGAAA CCTGGCCAGG CTCCCAGGCT CCTCATCTAT GATGCATCCA
              GGTTGTCTTT GGACCGGTCC GAGGGTCCGA GGAGTAGATA CTACGTAGGT
```

2084-9 LC variable region

CDR 2

```
              . R  A  T   G  I  P   A  R  F  S   G  S  G   S  G  T
      1251    ACAGGGCCAC TGGCATCCCA GCCAGGTTCA GTGGCAGTGG GTCTGGGACA
              TGTCCCGGTG ACCGTAGGGT CGGTCCAAGT CACCGTCACC CAGACCCTGT
```

2084-9 LC variable region

```
              D  F  T   L  T  I  S   S  L  E   P  E  D   F  A  V   Y.
      1301    GACTTCACTC TCACCATCAG CAGCCTAGAG CCTGAAGATT TTGCAGTTTA
              CTGAAGTGAG AGTGGTAGTC GTCGGATCTC GGACTTCTAA AACGTCAAAT
```

CDR 3

2084-9 LC variable region

```
              . Y  C  Q   Q  R  S  N   W  P  P   A  L  T   F  G  G  .
      1351    TTACTGTCAG CAGCGTAGCA ACTGGCCTCC GGCGCTCACT TTCGGCGGAG
              AATGACAGTC GTCGCATCGT TGACCGGAGG CCGCGAGTGA AAGCCGCCTC
```

C-kappa 2084-9 LC variable region

```
              . T  K  V   E  I  K   R  T  V   A  A  P   S  V  F  I
      1401    GGACCAAGGT GGAGATCAAA CGTACGGTGG CTGCACCATC TGTCTTCATC
              CCTGGTTCCA CCTCTAGTTT GCATGCCACC GACGTGGTAG ACAGAAGTAG
```

C-kappa

```
              F  P  P  S   D  E  Q   L  K  S   G  T  A  S   V  V  C.
      1451    TTCCCGCCAT CTGATGAGCA GTTGAAATCT GGAACTGCCT CTGTTGTGTG
              AAGGGCGGTA GACTACTCGT CAACTTTAGA CCTTGACGGA GACAACACAC
```

C-kappa

```
              . L  L  N   N  F  Y  P   R  E  A   K  V  Q   W  K  V  D.
      1501    CCTGCTGAAT AACTTCTATC CCAGAGAGGC CAAAGTACAG TGGAAGGTGG
              GGACGACTTA TTGAAGATAG GGTCTCTCCG GTTTCATGTC ACCTTCCACC
```

```
2601  GCAAGAACGG AGACCTACCC TGCCCTCCGC TCAGGAACGA GTTCAAGTAC
      CGTTCTTGCC TCTGGATGGG ACGGAGGCG AGTCCTTGCT CAAGTTCATG
2651  TTCCAAAGAA TGACCACAAC CTCTTCAGTG GAAGGTAAAC AGAATCTGGT
      AAGGTTTCTT ACTGGTGTTG GAGAAGTCAC CTTCCATTG TCTTAGACCA
2701  GATTATGGGT AGGAAAACCT GGTTCTCCAT TCCTGAGAAG AATCGACCTT
      CTAATACCCA TCCTTTTGGA CCAAGAGGTA AGGACTCTTC TTAGCTGGAA
2751  TAAAGGACAG AATTAATATA GTTCTCAGTA GAGAACTCAA AGAACCACCA
      ATTCCTGTC TTAATTATAT CAAGAGTCAT CTCTTGAGTT TCTTGGTGGT
2801  CGAGGAGCTC ATTTCTTGC CAAAAGTTTG GATGATGCCT TAAGACTTAT
      GCTCCTCGAG TAAAAGAACG GTTTTCAAAC CTACTACGGA ATTCTGAATA
2851  TGAACAACCG GAATGGCAA GTAAAGTAGA CATGGTTTGG ATAGTCGGAG
      ACTGTTGGC CTTAACCGTT CATTTCATCT GTACCAAACC TATCAGCCTC
2901  GCAGTTCTGT TTACCAGGAA GCCATGAATC AACCAGGCCA CCTCAGACTC
      CGTCAAGACA AATGGTCCTT CGGTACTTAG TTGGTCCGGT GGAGTCTGAG
2951  TTTGTGACAA GGATCATGCA GGAATTTGAA AGTGACACGT TTTTCCCAGA
      AAACACTGTT CCTAGTACGT CCTTAAACTT TCACTGTGCA AAAAGGGTCT
3001  AATGATTTG GGGAAATATA AACTTCTCCC AGAATACCCA GGCGTCCTCT
      TTAACTAAAC CCCTTTATAT TTGAAGAGGG TCTTATGGGT CCGCAGGAGA
3051  CTGAGGTCCA GGAGGAAAAA GGCATCAAGT ATAAGTTGA AGTCTACGAG
      GACTCCAGGT CCTCCTTTTT CCGTAGTTCA TATTCAAACT TCAGATGCTC
3101  AAGAAAGACT AACAGGAAGA TGCTTCAAG TTCTCTGCTC CCCTCCTAAA
      TTCTTTCTGA TTGTCCTTCT ACGAAGTTC AAGAGACGAG GGGAGGATTT
3151  GCTATGCATT TTATAAGAC CATGGACTT TTGCTGGCTT TAGATCTGAT
      CGATACGTAA AAATATTCTG GTACCCTGAA AACGACCGAA ATCTAGACTA
3201  CTTTGTGAAG GAACCTTACT TCTGTGGTGT GACATAATTG GACAAACTAC
      GAAACACTTC CTTGGAATGA AGACACCACA CTGTATTAAC CTGTTTGATG
3251  CTACAGAGAT TTAAAGCTCT AAGGTAAATA TAAAATTTTT AAGTGTATAA
      GATGTCTCTA AATTTCGAGA TTCCATTTAT ATTTTAAAAA TTCACATATT
3301  TGTGTTAAAC TACGATTCT AATGTTTGT GTATTTTAGA TTCCAACCTA
      ACACAATTTG ATGACTAAGA TTAACAAACA CATAAAATCT AAGGTTGGAT
3351  TGGAACTGAT GAATGGGAGC AGTGGTGGAA TGCCTTTAAT GAGGAAAACC
      ACCTTGACTA CTTACCCTCG TCACCACCTT ACGGAAATTA CTCCTTTTGG
3401  TGTTTGCTC AGAAGAAATG CCATCTAGTG ATGATGAGGC TACTGCTGAC
      ACAAAACGAG TCTTCTTTAC GGTAGATCAC TACTACTCCG ATGACGACTG
3451  TCTCAACATT CTACTCCTCC AAAAAAGAAG AGAAGGTAG AAGACCCCAA
      AGAGTTGTAA GATGAGGAGG TTTTTTCTTC TCTTCCATC TTCTGGGGTT
3501  GGACTTTCCT TCAGAATTGC TAAGTTTTT GAGTCATGCT GTGTTTAGTA
      CCTGAAAGGA AGTCTTAACG ATTCAAAAAA CTCAGTACGA CACAAATCAT
3551  ATAGAACTCT TGCTTGCTTT GCTATTTACA CCACAAAGGA AAAAGCTGCA
      TATCTTGAGA ACGAACGAAA CGATAAATGT GGTGTTTCCT TTTTCGACGT
3601  CTGCTATACA AGAAATTAT GGAAAAATAT TCTGTAACCT TTATAAGTAG
      GACGATATGT TCTTTTAATA CCTTTTTATA AGACATTGGA AATATTCATC
3651  GCATAACAGT TATAATCATA ACATACTGTT TTTTCTTACT CCACACAGGC
      CGTATTGTCA ATATTAGTAT TGTATGACAA AAAGAATGA GGTGTGTCCG
3701  ATAGAGTGTC TGCTATTAAT AACTATGCTC AAAAATTGTG TACCTTTAGC
      TATCTCACAG ACGATAATTA TTGATACGAG TTTTTAACAC ATGGAAATCG
3751  TTTTTAATTT GTAAAGGGGT TAATAAGGAA TATTTGATGT ATAGTGCCTT
      AAAAATTAAA CATTCCCCA ATAATTCCTT ATAAACTACA TATCACGGAA
3801  GACTAGAGNT CGATCATAAT CAGCCATACC ACATTGTAG AGGTTTACT
      CTGATCTCTA GCTAGTATTA GTCGGTATGG TGTAAACATC TCCAAATGA
3851  TGCTTAAAAA AACCTCCCAC ACCTCCCCCT GAACCTGAAA CATAAAATGA
      ACGAAATTTT TTGGAGGGTG TGGAGGGGGA CTTGGACTTT GTATTTTACT
3901  ATGCAATTGT TGTTGTTAAC TTGTTATTG CAGCTTATAA TGGTTACAAA
      TACGTTAACA ACAACAATTG AACAAATAAC GTCGAATATT ACCAATGTTT
```

```
5301  CGCTCAGTGG AACGAAAACT CACGTTAAGG GATTTGGTC  ATGAGATTAT
      GCGAGTCACC TTGCTTTTGA GTGCAATTCC CTAAAACCAG TACTCTAATA
5351  CAAAAAGGAT CTTCACCTAG ATCCTTTTAA ATTAAAAATG AAGTTTTAAA
      GTTTTTCCTA GAAGTGGATC TAGGAAAATT TAATTTTTAC TTCAAAATTT
5401  TCAATCTAAA GTATATATGA GTAAACTTGG TCTGACAGTT ACCAATGCTT
      AGTTAGATTT CATATATACT CATTTGAACC AGACTGTCAA TGGTTACGAA
5451  AATCAGTGAG GCACCTATCT CAGCGATCTG TCTATTTCGT TCATCCATAG
      TTAGTCACTC CGTGGATAGA GTCGCTAGAC AGATAAAGCA AGTAGGTATC
5501  TTGCCTGACT CCCCGTCGTG TAGATAACTA CGATACGGGA GGGCTTACCA
      AACGGACTGA GGGGCAGCAC ATCTATTGAT GCTATGCCCT CCCGAATGGT
5551  TCTGGCCCCA GTGCTGCAAT GATACCGCGA GACCCACGCT CACCGGCTCC
      AGACCGGGGT CACGACGTTA CTATGGCGCT CTGGGTGCGA GTGGCCGAGG
5601  AGATTTATCA GCAATAAACC AGCCAGCCGG AAGGGCCGAG CGCAGAAGTG
      TCTAAATAGT CGTTATTTGG TCGGTCGGCC TTCCCGGCTC GCGTCTTCAC
5651  GTCCTGCAAC TTTATCCGCC TCCATCCAGT CTATTAATTG TTGCCGGGAA
      CAGGACGTTG AAATAGGCGG AGGTAGGTCA GATAATTAAC AACGGCCCTT
5701  GCTAGAGTAA GTAGTTCGCC AGTTAATAGT TTGCGCAACG TTGTTGCCAT
      CGATCTCATT CATCAAGCGG TCAATTATCA AACGCGTTGC AACAACGGTA
5751  TGCTACAGGC ATCGTGGTGT CACGCTCCTC GTTTGGTATG GCTTCATTCA
      ACGATGTCCG TAGCACCACA GTGCGAGGAG CAAACCATAC CGAAGTAAGT
5801  GCTCCGGTTC CCAACGATCA AGGCGAGTTA CATGATCCCC CATGTTGTGC
      CGAGGCCAAG GGTTGCTAGT TCCGCTCAAT GTACTAGGGG GTACAACACG
5851  AAAAAGCGG TTAGCTCCTT CGGTCCTCCG ATCGTTGTCA GAAGTAAGTT
      TTTTTCGCC AATCGAGGAA GCCAGGAGGC TAGCAACAGT CTTCATTCAA
5901  GGCCGCAGTG TTATCACTCA TGGTTATGGC AGCACTGCAT AATTCTCTTA
      CCGGCGTCAC AATAGTGAGT ACCAATACCG TCGTGACGTA TTAAGAGAAT
5951  CTGTCATGCC ATCCGTAAGA TGCTTTTCTG TGACTGGTGA GTACTCAACC
      GACAGTACGG TAGGCATTCT ACGAAAAGAC ACTGACCACT CATGAGTTGG
6001  AAGTCATTCT GAGAATAGTG TATGCGGCGA CCGAGTTGCT CTTGCCCGGC
      TTCAGTAAGA CTCTTATCAC ATACGCCGCT GGCTCAACGA GAACGGGCCG
6051  GTCAATACGG GATAATACCG CGCCACATAG CAGAACTTTA AAAGTGCTCA
      CAGTTATGCC CTATTATGGC GCGGTGTATC GTCTTGAAAT TTTCACGAGT
6101  TCATTGGAAA ACGTTCTTCG GGGCGAAAAC TCTCAAGGAT CTTACCGCTG
      AGTAACCTTT TGCAAGAAGC CCCGCTTTTG AGAGTTCCTA GAATGGCGAC
6151  TTGAGATCCA GTTCGATGTA ACCCACTCGT GCACCCAACT GATCTTCAGC
      AACTCTAGGT CAAGCTACAT TGGGTGAGCA CGTGGGTTGA CTAGAAGTCG
6201  ATCTTTTACT TTCACCAGCG TTTCTGGGTG AGCAAAAACA GGAAGGCAAA
      TAGAAAATGA AAGTGGTCGC AAAGACCCAC TCGTTTTTGT CCTTCCGTTT
6251  ATGCCGCAAA AAAGGGAATA AGGGCGACAC GGAAATGTTG AATACTCATA
      TACGGCGTTT TTTCCCTTAT TCCCGCTGTG CCTTTACAAC TTATGAGTAT
6301  CTCTTCCTTT TTCAATATTA TTGAAGCATT TATCAGGGTT ATTGTCTCAT
      GAGAAGGAAA AAGTTATAAT AACTTCGTAA ATAGTCCCAA TAACAGAGTA
6351  GAGCGGATAC ATATTTGAAT GTATTTAGAA AAATAAACAA ATAGGGGTTC
      CTCGCCTATG TATAAACTTA CATAAATCTT TTTATTTGTT TATCCCCAAG
6401  CGCGCACATT TCCCCGAAAA GTGCCACCTG ACGTC
      GCGCGTGTAA AGGGGCTTTT CACGGTGGAC TGCAG
```

FIG. 4F

20H4.9-IgG1 Heavy Chain

20H4.9 Light chain natural Ig leader peptide

```
      M  K  H  L  W  F  F  L  L  V  A  A  P  R  W  V  ·
   1  ATGAAACACC TTGGTTCTT CCTCCTCCTG GTGGCAGCTC CCAGATGGGT
      TACTTTGTGG AACCAAGAA GGAGGAGGAC CACCGTCGAG GGTCTACCCA
```

20H4.9 HC variable region

```
      ·  L  S  Q  V  Q  L  Q  Q  W  G  A  G  L  L  K  P  ·
   51 CTGTCCCAG GTGCAACTAC AGCAGTGGGG CGCAGGACTG TTGAAGCCTT
      GGACAGGGTC CACGTTGATG TCGTCACCCC GCGTCCTGAC AACTTCGGAA
                                                       CDR 1
```

20H4.9 HC variable region

```
      ·  S  E  T  L  S  L  T  C  A  V  Y  G  G  S  F  S  G
   101 CGGAGACCCT GTCCCTCACC TGCGCTGTCT ATGGTGGGTC CTTCAGTGGT
       GCCTCTGGGA CAGGGAGTGG ACGCGACAGA TACCACCCAG GAAGTCACCA
         CDR 1
```

20H4.9 HC variable region

```
      ·  Y  Y  W  S  W  I  R  Q  S  P  E  K  G  L  E  W  I ·
   151 TACTACTGGA GCTGGATACG CCAGTCCCCA GAGAAGGGGC TGGAGTGGAT
       ATGATGACCT CGACCTATGC GGTCAGGGGT CTCTTCCCCG ACCTCACCTA
                                     CDR 2
```

20H4.9 HC variable region

```
      ·  G  E  I  N  H  G  G  Y  V  T  Y  N  P  S  L  E  S ·
   201 TGGGGAAATC AATCATGGTG GATACGTCAC CTACAATCCG TCCCTCGAGA
       ACCCCTTTAG TTAGTACCAC CTATGCAGTG GATGTTAGGC AGGGAGCTCT
       CDR 2
```

20H4.9 HC variable region

```
      ·  R  V  T  I  S  V  D  T  S  K  N  Q  F  S  L  K
   251 GTCGAGTCAC CATATCAGTA GACACGTCCA AGAACCAGTT CTCCCTGAAG
       CAGCTCAGTG GTATAGTCAT CTGTGCAGGT TCTTGGTCAA GAGGGACTTC
                                                       CDR 3
```

20H4.9 HC variable region

```
      ·  L  S  S  V  T  A  A  D  T  A  V  Y  Y  C  A  R  D ·
   301 CTGAGCTCTG TGACCGCCGC GGACACGGCT GTATATTACT GTGCGAGGGA
       GACTCGAGAC ACTGGCGGCG CCTGTGCCGA CATATAATGA CACGCTCCCT
                       CDR 3
```

20H4.9 HC variable region

```
      ·  Y  G  P  G  N  Y  D  W  Y  F  D  L  W  G  R  G  T ·
   351 CTATGGTCCG GGGAATTATG ACTGGTACTT CGATCTCTGG GGCCGTGGCA
       GATACCAGGC CCCTTAATAC TGACCATGAA GCTAGAGACC CCGGCACCGT
```

```
                    IgG1 CH2 domain
        ~~~~~~~~~~~~~~~~~~~~~~~~~~~~~~~~~~~~~~~~~~~~~~~~~~~~~~~
         · V V  D V S  R E D P  E V K  F N W
   851   GCGTGGTGGT GGACGTGAGC CACGAAGACC CTGAGGTCAA GTTCAACTGG
         CGCACCACCA CCTGCACTCG GTGCTTCTGG GACTCCAGTT CAAGTTGACC
                    IgG1 CH2 domain
        ~~~~~~~~~~~~~~~~~~~~~~~~~~~~~~~~~~~~~~~~~~~~~~~~~~~~~~~
          Y V D G  Y E V  H N A  K T K  P R E  E ·
   901   TACGTGGACG GCGTGGAGGT GCATAATGCC AAGACAAAGC CGCGGGAGGA
         ATGCACCTGC CGCACCTCCA CGTATTACGG TTCTGTTTCG GCGCCCTCCT
                    IgG1 CH2 domain
        ~~~~~~~~~~~~~~~~~~~~~~~~~~~~~~~~~~~~~~~~~~~~~~~~~~~~~~~
         · Q Y N  S T Y  R V V  S V L  T V L  H Q ·
   951   GCAGTACAAC AGCACGTACC GTGTGGTCAG CGTCCTCACC GTCCTGCACC
         CGTCATGTTG TCGTGCATGG CACACCAGTC GCAGGAGTGG CAGGACGTGG
                    IgG1 CH2 domain
        ~~~~~~~~~~~~~~~~~~~~~~~~~~~~~~~~~~~~~~~~~~~~~~~~~~~~~~~
         · D W L  N G K  E Y K  C K V  S N K  A
  1001   AGGACTGGCT GAATGGCAAG GAGTACAAGT GCAAGGTCTC CAACAAAGCC
         TCCTGACCGA CTTACCGTTC CTCATGTTCA CGTTCCAGAG GTTGTTTCGG
                                                        IgG1 CH3 domain
                                                       ~~~~~~~~~~~~~~~~
                    IgG1 CH2 domain
        ~~~~~~~~~~~~~~~~~~~~~~~~~~~~~~~~~~~~~~~~~~~~~~~~~~~~~~~
          L P A P  I E K  T I S  K A K  G Q P R ·
  1051   CTCCCAGCCC CCATCGAGAA AACCATCTCC AAAGCCAAAG GGCAGCCCCG
         GAGGGTCGGG GGTAGCTCTT TTGGTAGAGG TTTCGGTTTC CCGTCGGGGC
                    IgG1 CH3 domain
        ~~~~~~~~~~~~~~~~~~~~~~~~~~~~~~~~~~~~~~~~~~~~~~~~~~~~~~~
         · E P Q  V Y T L  P P S  R D E  L T K N ·
  1101   AGAACCACAG GTGTACACCC TGCCCCCATC CCGGGATGAG CTGACCAAGA
         TCTTGGTGTC CACATGTGGG ACGGGGGTAG GGCCCTACTC GACTGGTTCT
                    IgG1 CH3 domain
        ~~~~~~~~~~~~~~~~~~~~~~~~~~~~~~~~~~~~~~~~~~~~~~~~~~~~~~~
         · Q V S  L T C  L V K G  F Y P  S D I
  1151   ACCAGGTCAG CCTGACCTGC CTGGTCAAAG GCTTCTATCC CAGCGACATC
         TGGTCCAGTC GGACTGGACG GACCAGTTTC CGAAGATAGG GTCGCTGTAG
                    IgG1 CH3 domain
        ~~~~~~~~~~~~~~~~~~~~~~~~~~~~~~~~~~~~~~~~~~~~~~~~~~~~~~~
          A V E W  E S N  G Q P  E N N Y  K T T ·
  1201   GCCGTGGAGT GGGAGAGCAA TGGGCAGCCG GAGAACAACT ACAAGACCAC
         CGGCACCTCA CCCTCTCGTT ACCCGTCGGC CTCTTGTTGA TGTTCTGGTG
                    IgG1 CH3 domain
        ~~~~~~~~~~~~~~~~~~~~~~~~~~~~~~~~~~~~~~~~~~~~~~~~~~~~~~~
         · P P V  L D S D  G S F  F L Y  S K L T ·
  1251   GCCTCCCGTG CTGGACTCCG ACGGCTCCTT CTTCCTCTAC AGCAAGCTCA
         CGGAGGGCAC GACCTGAGGC TGCCGAGGAA GAAGGAGATG TCGTTCGAGT
                    IgG1 CH3 domain
        ~~~~~~~~~~~~~~~~~~~~~~~~~~~~~~~~~~~~~~~~~~~~~~~~~~~~~~~
         · V D K  S R W  Q Q G  N V F S  C S V
  1301   CCGTGGACAA GAGCAGGTGG CAGCAGGGGA ACGTCTTCTC ATGCTCCGTG
         GGCACCTGTT CTCGTCCACC GTCGTCCCCT TGCAGAAGAG TACGAGGCAC
```

FIG. 7C

```
                   IgG1 CH3 domain
         ~~~~~~~~~~~~~~~~~~~~~~~~~~~~~~~~~~~~~~~~~~~~~~~
           M  H  E  A  L  H  N  H  Y  T  Q  K  S  L  S  L  S  .
  1351   ATGCATGAGG CTCTGCACAA CCACTACACC CAGAAGAGCC TCTCCCTGTC
         TACGTACTCC GAGACGTGTT GGTGATGTGG GTCTTCTCGG AGAGGGACAG
         IgG1 CH3 domain
         ~~~~~~~~~~~~
           .  P  G  K
  1401   CCCGGGTAAA TGA
         GGGCCCATTT ACT
```

FIG. 7D

FULLY HUMAN ANTIBODIES AGAINST HUMAN 4-1BB

This application is a continuation of U.S. application Ser. No. 12/653,137 filed on Dec. 9, 2009, which is a continuation of U.S. Divisional application Ser. No. 11/903,106 filed on Sep. 20, 2007, now allowed, which claims priority to Non-Provisional application Ser. No. 10/961,567 filed Oct. 8, 2004, issued as U.S. Pat. No. 7,288,638, which claims priority to U.S. Provisional Application No. 60/510,193, filed Oct. 10, 2003, whose contents are hereby incorporated by reference.

FIELD OF THE INVENTION

The invention is directed to fully human antibodies and, more specifically, to fully human antibodies to human 4-1BB (CD137).

BACKGROUND OF THE INVENTION

An extensive body of evidence has unequivocally demonstrated that some degree of immune response against cancer exists in humans and animals. In cancer patients, cellular components of the immune system are able to recognize antigens expressed by tumor cells, such as differentiation of oncofetal antigens or mutated gene products (S. Rosenberg, Nature, 411:380-4 (2001); P. van der Bruggen et al., Immunological Rev., 188:51-64 (2002)). A number of clinical studies have shown that tumor-infiltrating lymphocytes have favorable prognostic significance (E. Halapi, Med. Oncol., 15(4):203-11 (1998); Y. Naito et al., Cancer Res., 58(16): 3491-4 (1998); L. Zhang et al., N.E. J. Med., 348(3):203-13 (2003)). Furthermore, treatment with immunomodulators, such as cytokines or bacterial products, cancer vaccines, or adoptive immunotherapy has led to tumor regression in a number of patients (S. Rosenberg, Cancer J. Sci. Am. 6(S):2 (2000); P. Bassi, Surg. Oncol., 11(1-2):77-83 (2002); S. Antonia et al., Current Opinion in Immunol., 16:130-6 (2004)). Despite these responses, immunity against cancer frequently fails to effectively eliminate tumor cells. The causes for this failure can be grouped into three major categories: (i) impaired tumor recognition by immune cells, either by variable expression of tumor antigens or reduced expression of class I major histocompatibility complex (MHC); (ii) immunosuppressive tumor microenvironment, as a result of secretion of inhibitory cytokines by tumor cells (e.g., TGF-β); and (iii) poor tumor immunogenicity due to the lack of expression of co-stimulatory molecules on tumor cells, which results in the inability of the tumor cells to effectively stimulate T-cells. Advances in our understanding of the requirements for tumor antigen recognition and immune effector function indicate that a potential strategy to enhance an anti-tumor immune response is to provide co-stimulation through an auxiliary molecule. Tumor antigen-specific T-cells require costimulation to initiate and maintain effector functions. Thus, therapies that target costimulatory molecules can be applied to modulate and enhance the immune response to tumors.

The current model for T-cell activation postulates that naive T-cells require two signals for full activation: (i) a signal provided through the binding of processed antigens presented to the T-cell receptor by major histocompatibility complex (MHC) class I molecules; and (ii) an additional signal provided by the interaction of co-stimulatory molecules on the surface of T-cells and their ligands on antigen presenting cells. Recognition of an antigen by a naive T-cell is insufficient in itself to trigger T-cell activation. Without a co-stimulatory signal, T-cells may be eliminated either by death or by induction of anergy. Signaling through the CD28 costimulatory molecule appears to be key for the initiation of T-cell responses. However, CD137 (4-1BB) signaling has been shown to be primordial for the maintenance and expansion of the immune response to antigens, as well as, for the generation of memory T-cells.

CD137 (4-1BB) is a member of the tumor necrosis receptor (TNF-R) gene family, which includes proteins involved in regulation of cell proliferation, differentiation, and programmed cell death. CD137 is a 30 kDa type I membrane glycoprotein expressed as a 55 kDa homodimer. The receptor was initially described in mice (B. Kwon et al., P.N.A.S. USA, 86:1963-7 (1989)), and later identified in humans (M. Alderson et al., Eur. J. Immunol., 24: 2219-27 (1994); Z. Zhou et al., Immunol. Lett., 45:67 (1995)) (See, also, Published PCT Applications WO95/07984 and WO96/29348, and U.S. Pat. No. 6,569,997, hereby incorporated by reference (See, SEQ ID NO:2.)). The human and murine forms of CD137 are 60% identical at the amino acid level. Conserved sequences occur in the cytoplasmic domain, as well as 5 other regions of the molecule, indicating that these residues might be important for function of the CD137 molecule (Z. Zhou et al., Immunol. Lett., 45:67 (1995)). Expression of CD137 has been shown to be predominantly on cells of lymphoid lineage such as activated T-cells, activated Natural Killer (NK) cells, NKT-cells, CD4CD25 regulatory T-cells, and also on activated thymocytes, and intraepithelial lymphocytes. In addition, CD137 has also been shown to be expressed on cells of myeloid origin like dendritic cells, monocytes, neutrophils, and eosinophils. Even though CD137 expression is mainly restricted to immune/inflammatory cells, there have been reports describing its expression on endothelial cells associated with a small number of tissues from inflammatory sites and tumors.

Functional activities of CD137 on T-cells have been amply characterized. Signaling through CD137 in the presence of suboptimal doses of anti-CD3 has been demonstrated to induce T-cell proliferation and cytokine synthesis (mainly IFN-γ), and to inhibit activated cell death. These effects have been observed with both murine and human T-cells (W. Shuford et al., J. Exp. Med., 186(1):47-55 (1997); D. Vinay et al., Semin. Immunol., 10(6):481-9 (1998); D. Laderach et al., Int. Immunol., 14(10):1155-67 (2002)). In both humans and mice, co-stimulation enhances effector functions, such as IFN-γ production and cytotoxicity, by augmenting the numbers of antigen-specific and effector CD8+ T-cells. In the absence of anti-CD3 signaling, stimulation through CD137 does not alter T-cell function, indicating that CD137 is a co-stimulatory molecule.

The physiological events observed following CD137 stimulation on T-cells are mediated by NF-κB and PI3K/ERK1/2 signals with separate physiological functions. NF-κB signals trigger expression of Bcl-$_{XL}$, an anti-apoptotic molecule, thus resulting in increased survival, whereas PI3K and ERK1/2 signals are specifically responsible for CD137-mediated cell cycle progression (H. Lee et al., J. Immunol., 169(9):4882-8 (2002)). The effect of CD137 activation on the inhibition of activation-induced cell death was shown in vitro by Hurtado et al. (J. Hurtado et al., J. Immunol., 158(6): 2600-9 (1997)), and in an in vivo system in which anti-CD137 monoclonal antibodies (mabs) were shown to produce long-term survival of superantigen-activated CD8+ T-cells by preventing clonal deletion (C. Takahashi et al., J. Immunol., 162:5037 (1999)). Later, two reports demonstrated, under different experimental conditions, that the CD137 signal regulated both clonal expansion and survival of CD8+ T-cells (D. Cooper et al., Eur. J. Immunol., 32(2):521-9 (2002); M.

Maus et al., Nat. Biotechnol., 20:143 (2002)). Reduced apoptosis observed after co-stimulation correlated with increased levels of Bcl-$_{xL}$ in CD8+ T-cells, while Bcl-2 expression remained unchanged. Up-regulation of the anti-apoptotic genes Bcl-$_{xL}$ and bfl-1 via 4-1BB was shown to be mediated by NF-κB activation, since PDTC, an NF-κB-specific blocker, inhibited 4-1BB-mediated up-regulation of Bcl-$_{xL}$ (H. Lee et al., J. Immunol., 169(9):4882-8 (2002)). On the other hand, clonal expansion of activated T-cells appears to be mediated by increased expression of cyclins D2, D3, and E, and down-regulation of the p27$^{kip1}$ protein. This effect occurs in both an IL-2 dependent and independent fashion (H. Lee et al., J. Immunol., 169(9):4882-8 (2002)). Altogether, CD137 stimulation results in enhanced expansion, survival, and effector functions of newly primed CD8+ T-cells, acting, in part, directly on these cells. Both CD4+ and CD8+ T-cells have been shown to respond to CD137 stimulation, however, it appears that enhancement of T-cell function is greater in CD8+ cells (W. Shuford et al., J. Exp. Med., 186(1):47-55 (1997); I. Gramaglia et al., Eur. J. Immunol., 30(2):392-402 (2000); C. Takahashi et al., J. Immunol., 162:5037 (1999)). Based on the critical role of CD137 stimulation in CD8+ T-cell function and survival, manipulation of the CD137/CD137L system provides a plausible approach for the treatment of tumors and viral pathogens.

Recently, the constitutive expression of CD137 on freshly isolated dendritic cells (DCs) was demonstrated in mice (R. Wilcox et al., J. Immunol., 169(8):4230-6 (2002); T. Futagawa et al., Int. Immunol, 14(3):275-86 (2002)) and humans (S. Pauly et al., J. Leukoc. Biol. 72(1):35-42 (2002)). These reports showed that stimulation of CD137 on DCs resulted in secretion of IL-6 and IL-12, and, more importantly, it enhanced DC ability to stimulate T-cell responses to alloantigens. Furthermore, Pan et al. demonstrated that CD137 signaling in DCs resulted in upregulation of MHC Class I and costimulatory molecules, and produced an increased ability of DCs to infiltrate tumors (P. Pan et al., J. Immunol., 172(8):4779-89 (2004)). Therefore, CD137 costimulation on DCs appears to be a novel pathway for proliferation, maturation, and migration of DCs.

Activated Natural Killer (NK) cells express CD137 following stimulation with cytokines (I. Melero et al., Cell Immunol., 190(2):167-72 (1998); R. Wilcox et al., J. Immunol., 169(8):4230-6 (2002)). Several reports demonstrated that NK cells appear to be critical for the modulation of the antitumor immune response induced by agonistic CD137 antibodies ((I. Melero et al., Cell Immunol., 190(2):167-72 (1998); R. Miller et al., J. Immunol., 169(4):1792-800 (2002); R. Wilcox et al., J. Immunol., 169(8):4230-6 (2002)). Depletion of NK cells significantly reduces the antitumor activity of anti-CD137 mabs. Ligation of CD137 on NK cells induces proliferation and IFN-γ secretion, but does not affect their cytolytic activity. Notably, in vitro, CD137-stimulated NK cells presented an immunoregulatory or "helper" activity for CD8+ cytolytic T-cells resulting in expansion of activated T-cells. Therefore, CD137 signaling on NK cells may modulate innate immunity to tumors.

A paradoxical effect has been described for CD137 stimulation in that agonistic CD137 antibodies can induce suppression of the humoral responses to T-cell antigens in primates and mouse models (H. Hong et al., J. Immunother., 23(6):613-21 (2000); R. Mittler et al., J. Exp. Med., 190(10):1535-40 (1999)). Notably, CD137 agonistic antibodies were shown to produce significant amelioration of the symptoms associated with antibody dependent autoimmune diseases such as systemic lupus erythematosus and experimental autoimmune encephalomyelitis (J. Foell et al., N.Y. Acad. Sci., 987:230-5 (2003); Y. Sun et al., Nat. Med., 8(12):1405-13 (2002)). Recently, Seo et al. demonstrated that, in a mouse model of rheumatoid arthritis, treatment with an agonistic anti-CD137 antibody prevented the development of the disease, and remarkably, blocked disease progression (S. K. Seo et al., Nat. Med. 10; 1099-94 (2004)). The mechanism responsible for this effect has not been well defined, but in the model of rheumatoid arthritis it was shown that treatment with a CD137 agonistic antibody resulted in the expansion of IFN-γ-producing CD11C-CD8+ T cells. IFN-γ in turn stimulated dendritic cells to produce indolamine-2,3-dioxygenase (IDO), which exerts immuno-suppressive activities. It has also been postulated that CD137 signaling on antigen-activated CD4+ T-cells results in induction of IFN-γ secretion which activates macrophages. Activated macrophages can in turn produce death signals for B cells. Continuous signaling through CD137 on CD4+ T-cells may subsequently induce activation-induced cell death (AICD) of these CD4+ activated T-cells. Therefore, by eliminating antigen-activated T-cells and B cells, a reduced antibody response is observed and, consequently, a dramatic reduction of Th2-mediated inflammatory diseases is observed (B. Kwon et al., J. Immunol., 168(11):5483-90 (2002)). These studies suggest a role for the use of agonistic CD137 antibodies for the treatment of inflammatory or autoimmune diseases, without inducing a general suppression of the immune system.

The natural ligand for CD137, CD137 ligand (CD137L), a 34 kDa glycoprotein member of the TNF superfamily, is detected mainly on activated antigen-presenting cells (APC), such as B cells, macrophages, dendritic cells, and also on murine B-cell lymphomas, activated T-cells, and human carcinoma lines of epithelial origin (R. Goodwin et al., Eur. J. Immunol., 23(10):2631-41 (1993); Z. Zhou et al., Immunol. Lett., 45:67 (1995); H. Salih et al., J. Immunol., 165(5):2903-10 (2000)). Human CD137L shares 36% homology with its murine counterpart (M. Alderson et al., Eur. J. Immunol., 24: 2219-27 (1994)).

In addition to delivering signals to CD137-expressing cells, binding of CD137 to CD137L initiates a bidirectional signal resulting in functional effects on CD137L-expressing cells. Langstein et al. demonstrated that binding of CD137-Ig fusion protein to CD137L on activated monocytes induced the production of IL-6, IL-8, and TNF-α, upregulated ICAM, and inhibited IL-10, resulting in increased adherence (J. Langstein et al., J. Immunol., 160(5):2488-94 (1998)). In addition, proliferation of monocytes was demonstrated along with a higher rate of apoptosis (J. Langstein et al., J. Leukoc. Biol., 65(6):829-33 (1999)). These observations were confirmed by the studies of Ju et al. (S. Ju et al., Hybrid Hybridomics, 22(5):333-8 (2003)), which showed that a functional anti-CD137L antibody induced a high rate of proliferation of peripheral blood monocytes. Blocking the ligand resulted in inhibition of T-cell activation. In addition, soluble CD137L was found in the serum of patients with rheumatoid arthritis and hematological malignancies (H. Salih et al., J. Immunol., 167(7):4059-66 (2001)). Thus, the interaction of CD137 with CD137L influences and produces functional effects on T-cells and APC.

In another important aspect of T-cell function, it has been demonstrated that agonistic anti-CD137 antibodies rescued T-cell responses to protein antigens in aged mice. It has been well documented that an age-related decline in the immune response to antigens occurs, a process known as immunosenescence (R. Miller, Science, 273:70-4 (1996); R. Miller, Vaccine, 18:1654-60 (2000); F. Hakim et al., Curr. Opinion Immunol., 16:151-156 (2004)). This phenomenon appears to be due to alterations in the equilibrium between the extent of cellular expansion and cellular survival or death. Bansal-Pakala et al. tested the hypothesis that secondary costimulation through CD137 can be used to enhance T-cell responses in situations where T-cells do not receive sufficient stimulation, due to either reduced expression of CD3 or CD28, or reduced quality of signals. Their studies showed that aged mice had a deficient in vitro recall response compared to young mice (P. Bansal-Pakala et al., J. Immunol., 169(9): 5005-9 (2002)). However, when aged mice were treated with anti-CD137 mabs, the proliferative and cytokine responses of T-cells were identical to the responses observed in young mice. While the specific mechanism responsible for this effect was not elucidated, it was speculated that enhancing both the expression of anti-apoptotic molecules like Bcl-$_{XL}$, and the promotion of IL-2 secretion in vivo may play a role in rescuing defective T-cell responses. These studies demonstrated the potential for agonistic anti-CD137 antibodies to rescue weak T-cell responses in elderly immuno-compromised individuals, and has profound implications for the use of anti-CD137 antibodies in cancer patients.

A role for CD137 targeted therapy in the treatment of cancer was suggested by in vivo efficacy studies in mice utilizing agonistic anti-murine CD137 monoclonal antibodies. In a paper by Melero et al., agonistic anti-mouse CD137 antibody produced cures in P815 mastocytoma tumors, and in the low immunogenic tumor model Ag104 (I. Melero et al., Nat. Med., 3(6):682-5 (1997)). The anti-tumor effect required both CD4+ and CD8+ T-cells and NK cells, since selective in vivo depletion of each subpopulation resulted in the reduction or complete loss of the anti-tumor effect. It was also demonstrated that a minimal induction of an immune response was necessary for anti-CD137 therapy to be effective. Several investigators have used anti-CD137 antibodies to demonstrate the viability of this approach for cancer therapy (J. Kim et al., Cancer Res., 61(5):2031-7 (2001); O. Martinet et al., Gene Ther., 9(12):786-92 (2002); R. Miller et al., J. Immunol., 169(4):1792-800 (2002); R. Wilcox et al., Cancer Res., 62(15):4413-8 (2002)).

In support of the anti-tumor efficacy data with agonistic CD137 antibodies, signals provided by CD137L have been shown to elicit CTL activity and anti-tumor responses (M. DeBenedette et al., J. Immunol., 163(9):4833-41 (1999); B. Guinn et al., J. Immunol., 162(8):5003-10 (1999)). Several reports demonstrated that gene transfer of CD137 ligand into murine carcinomas resulted in tumor rejection, demonstrating the requirement of costimulation in generating an efficient immune response (S. Mogi et al., Immunology, 101(4):541-7 (2000); I. Melero et al., Cell Immunol., 190(2):167-72 (1998); B. Guinn et al., J. Immunol., 162(8):5003-10 (1999)). Salih et al. reported the expression of CD137L in human carcinomas and human carcinoma cell lines (H. Salih et al., J. Immunol., 165(5):2903-10 (2000)), and demonstrated that tumors cells expressing the ligand were able to deliver a co-stimulatory signal to T-cells which resulted in the release of IFN-γ and IL-2, and that this effect correlated with the levels of CD137L on tumors. Whether expression of CD137L in human tumors could make these tumors more susceptible to agonistic CD137 antibodies is not known.

CD137L −/− mice have underscored the importance of the CD137/CD137L system in T-cell responses to both viruses and tumors (M. DeBenedette et al., J. Immunol., 163(9): 4833-41 (1999); J. Tan et al., J. Immunol., 164(5):2320-5 (2000); B. Kwon et al., J. Immunol., 168(11):5483-90 (2002)). Studies using CD137- and CD137L-deficient mice have demonstrated the importance of CD137 costimulation in graft-vs-host disease, and anti-viral cytolytic T-cell responses. CD137-deficient mice had an enhanced proliferation of T-cells, but a reduction in cytokine production and cytotoxic T-cell activity (B. Kwon et al., J. Immunol., 168 (11):5483-90 (2002); D. Vinay et al., Immunol. Cell Biol., 81(3):176-84 (2003)). More recently, it was shown that knockout mice (CD137−/−) had a higher frequency of tumor metastases (4-fold) compared to control mice. These data suggest that restoration of CD137 signaling by the use of agonistic anti-CD137 antibodies is a feasible approach for augmenting cellular immune responses to viral pathogens and cancers.

In addition to the data in mouse in vivo models which supports the involvement of CD137 signaling in antitumor immune responses, studies conducted in primary human tumor samples have confirmed the role of CD137 in generating effector T-cells. In patients with Ewing sarcoma, Zhang et al. showed that intratumoral effector T-cells presented the CD3+/CD8+/CD28−/CD137+ phenotype. Unexpectedly, coexistence of progressive tumor growth and anti-tumor immunity (effector T-cells) was observed. Ex vivo stimulation studies with patients' cells demonstrated that tumor-induced T-cell proliferation and activation required costimulation with CD137L. Stimulation of PBL with anti-CD3/CD137L, but not anti-CD3/anti-CD28, induced tumor lytic effectors. These studies provided further evidence that CD137 mediated costimulation could result in expansion of tumor reactive CTLs (H. Zhang et al., Cancer Biol. Ther., 2(5):579-86 (2003)). Furthermore, expression of CD137 was demonstrated in tumor infiltrating lymphocytes in hepatocellular carcinomas (HCC) (Y. Wan et al., World J. Gastroenterol, 10(2):195-9 (2004)). CD137 expression was detected in 19 out of 19 HCC by RT-PCR, and in 13/19 by immunofluorescence staining. Conversely, CD137 was not detected in the peripheral mononuclear cells of the same patients. Analyses conducted in healthy donor liver tissues failed to demonstrate expression of CD137. These studies did not attempt to correlate clinical disease with CD137 expression. Thus, studies conducted in Ewing sarcoma and hepatocellular carcinoma revealed the presence of TIL that express CD137, with concomitant disease progression. In Ewing sarcomas it was demonstrated that CD137+TILs were able to kill tumor cells ex-vivo suggesting that the CD137 pathway was intact in these patients, and that perhaps suppressive factors in the tumor microenvironment inhibited their function. Hence, it can be postulated that systemic administration of agonistic CD137 antibodies may provide the signal necessary for expansion of these effector T-cells.

In addition to its role in the development of immunity to cancer, experimental data supports the use of CD137 agonistic antibodies for the treatment of autoimmune and viral diseases (B. Kwon et al., Exp. Mol. Med., 35(1):8-16 (2003); H. Salih et al., J. Immunol., 167(7):4059-66 (2001); E. Kwon et al., P.N.A.S. USA, 96:15074-79 (1999); J. Foell et al., N.Y. Acad. Sci., 987:230-5 (2003); Y. Sun et al., Nat. Med., 8(12): 1405-13 (2002) S. K. Seo et al, Nat. Med. 10; 1099-94 (2004)).

Consequently, based on the roles of 4-1BB in modulating immune response, it would be desirable to produce anti-human 4-1BB antibodies with agonistic activities that could be used for the treatment or prevention of human diseases such as cancer, infectious diseases, and autoimmune diseases.

BRIEF SUMMARY OF THE INVENTION

The present invention provides fully human antibodies that bind to human 4-1BB (H4-1BB) and that allow binding of H4-1BB to a human 4-1BB ligand (H4-1BBL). Thus, the invention is directed to antibodies that bind to H4-1BB and that do not block the binding of H4-1BB to H4-1BBL, thereby permitting the binding of both an antibody of the invention and H4-1BBL to H4-1BB. The invention also provides antibodies with agonistic activities in that binding of the antibodies to H4-1BB results in an enhancement and stimulation of H4-1BB mediated immune responses. These antibodies can be used as immuno-enhancers of an anti-tumor or anti-viral immune response, or as immunomodulators of T cell mediated autoimmune diseases. The antibodies can also be used as diagnostic tools for the detection of H4-1BB in blood or tissues of patients with cancer, autoimmune, or other diseases.

In one aspect, the invention provides a monoclonal antibody or antigen-binding portion thereof that specifically binds to H4-1BB, comprising a light chain variable region and a heavy chain variable region, wherein the light chain variable region comprises a CDR1 (complementary determining region 1), a CDR2 (complementary determining region 2), and a CDR3 (complementary determining region 3) as depicted in FIG. 4, and the heavy chain variable region comprises a CDR1 (complementary determining region 1), a CDR2 (complementary determining region 2), and a CDR3 (complementary determining region 3) as depicted in FIG. 3 or FIG. 7. The monoclonal antibody (mab) can be, for example, an IgG4 antibody or IgG1 antibody.

In another aspect, the invention provides a monoclonal antibody or antigen-binding portion thereof, wherein the light chain comprises a variable region as depicted in FIG. 4, and the heavy chain comprises a variable region as depicted in FIG. 3 or FIG. 7.

In another aspect, the invention provides a monoclonal antibody comprising a light chain and a heavy chain, wherein the light chain comprises amino acid residues 21-236 of SEQ ID NO:6 and the heavy chain comprises amino acid residues 20-467 of SEQ ID NO:3. In another aspect, the invention provides a monoclonal antibody comprising a light chain and a heavy chain, wherein the light chain comprises amino acid residues 21-236 of SEQ ID NO:6 and the heavy chain comprises amino acid residues 20-470 of SEQ ID NO:9.

The antibodies of the invention have wide therapeutic applications as immunomodulators of diseases such as cancer, autoimmune diseases, inflammatory diseases, and infectious diseases.

The invention further provides methods for treating cancer in a subject comprising administering a therapeutically effective amount of an antibody of the invention to the subject. In one aspect, this method further comprises administering a vaccine. Suitable vaccines include, for example, a tumor cell vaccine, a DNA vaccine, a GM-CSF-modified tumor cell vaccine, or an antigen-loaded dendritic cell vaccine. The cancer can be, for example, prostate cancer, melanoma, or epithelial cancer.

In another aspect, the invention provides a method for enhancing the immune response, comprising administration of an antibody of the invention and a SIV gag vaccine. In another aspect, the invention provides a method for enhancing the immune response, comprising administration of an antibody of the invention and a PSA vaccine. In another aspect, the invention provides a method for enhancing the immune response to a SIV gag vaccine, comprising administration of an antibody of the invention. In another aspect, the invention provides a method for enhancing the immune response to a PSA vaccine, comprising administration of an antibody of the invention.

The invention also provides pharmaceutical compositions comprising an antibody of the invention, or an antigen-binding portion thereof, and a pharmaceutically acceptable carrier. The pharmaceutical composition can be administered alone or in combination with an agent, e.g., an agent for treating cancer such as a chemotherapeutic agent or a vaccine or other immunomodulatory agent.

The invention also provides isolated polynucleotides comprising a nucleotide sequence selected from: (a) nucleotides that encode the amino acid sequence of amino acid residues 20-467 of SEQ ID NO:3; (b) nucleotides that encode the amino acid sequence of SEQ ID NO:3; (c) nucleotides that encode the amino acid sequence of amino acid residues 21-236 of SEQ ID NO:6; (d) nucleotides that encode the amino acid sequence of SEQ ID NO:6; (e) nucleotides that encode the amino acid sequence of amino acid residues 20-470 of SEQ ID NO:9; (f) nucleotides that encode the amino acid sequence of SEQ ID NO:9; and (g) nucleotides that encode a fragment of an amino acid sequence of (a) to (f), such as a variable region, constant region, or one or more CDRs. The isolated polynucleotides of the invention further comprise nucleotide sequences encoding at least one CDR of FIG. 3, at least one CDR of FIG. 4, or at least one CDR of FIG. 7. The invention further provides isolated polynucleotides that comprise the nucleotide sequence of SEQ ID NO:1, SEQ ID NO:4, or SEQ ID NO:7.

The invention also provides isolated polypeptides comprising an amino acid sequence selected from the group consisting of SEQ ID NO:3, SEQ ID NO:6, and SEQ ID NO:9. In another aspect, the invention provides isolated polypeptides comprising the amino acid sequence of amino acid residues 20-467 of SEQ ID NO:3, isolated polypeptides comprising the amino acid sequence of amino acid residues 21-236 of SEQ ID NO:6, and isolated polypeptides comprising the amino acid sequence of amino acid residues 20-470 of SEQ ID NO:9. In another aspect, the invention provides isolated polypeptides comprising the amino acid sequence of at least one CDR of FIG. 3, FIG. 4, or FIG. 7, or at least the variable or constant region of FIG. 3, FIG. 4, or FIG. 7.

The invention further includes an immunoglobulin having binding specificity for H4-1BB, said immunoglobulin comprising an antigen binding region. In one aspect, the immunoglobulin is a Fab or F(ab')$_2$ of an antibody of the invention.

The invention also includes a cell line that produces an antibody or antigen-binding portion thereof of the invention, recombinant expression vectors that include the nucleotides of the invention, and methods to make the antibodies of the invention by culturing an antibody-producing cell line.

BRIEF DESCRIPTION OF THE DRAWINGS

FIG. 1 shows a plasmid map of pD17-20H4.9.h4a.

FIG. 3 (FIGS. 3A-3H) shows the nucleotide sequence of the plasmid pD17-20H4.9.h4a, including the coding strand (SEQ ID NO:1), complementary strand (SEQ ID NO:2), and amino acid sequence (leader peptide is amino acid residues 1-19 of SEQ ID NO:3; heavy chain is amino acid residues 20-467 of SEQ ID NO:3) encoded by the coding strand.

FIG. 4 (FIGS. 4A-4F) shows the nucleotide sequence of the plasmid pD16gate-20H4.9.LC, including the coding strand (SEQ ID NO:4), complementary strand (SEQ ID NO:5), and amino acid sequence (leader peptide is amino acid residues 1-20 of SEQ ID NO:6; light chain is amino acid residues 21-236 of SEQ ID NO:6) encoded by the coding strand.

FIG. 7 (FIGS. 7A-7D shows the nucleotide and amino acid sequences of the 20H4.9-IgG1 heavy chain construct, including the coding strand (SEQ ID NO:7), complementary strand (SEQ ID NO:8), and amino acid sequence (leader peptide is amino acid residues 1-19 of SEQ ID NO:9; heavy chain is amino acid residues 20-470 of SEQ ID NO:9) encoded by the coding strand.

DETAILED DESCRIPTION OF THE INVENTION

The invention is directed to the preparation and characterization of antibodies, and antigen binding fragments thereof (including fusion proteins that comprise an antigen binding fragment of an antibody of the invention), for use in the treatment of a disease, such as a cancer, infectious disease, inflammatory disease, or autoimmune disease. The cancer can be, for example, prostate cancer, melanoma, or epithelial cancer.

The antibodies are capable of binding to H4-1BB, and can present high affinity for H4-1BB and effectively enhance T cell responses. In one aspect, the antibody induces IFN-γ production in co-stimulatory assays, but does not affect the binding of H4-1BB to its corresponding ligand, H4-1BBL, and does not fix complement.

The antibodies of the invention may be produced by methods well known in the art. In one aspect, the antibodies can be produced by expression in transfected cells, such as immortalized eukaryotic cells, such as myeloma or hybridoma cells.

The antibodies of the invention may be used alone, or together with other therapeutic agents such as radiotherapy (including radiation), hormonal therapy, cytotoxic agents, vaccines, and other immunomodulatory agents, such us cytokines and biological response modifiers. These agents are particularly useful in treating cancer and immune-proliferative disorders.

Figure 1:
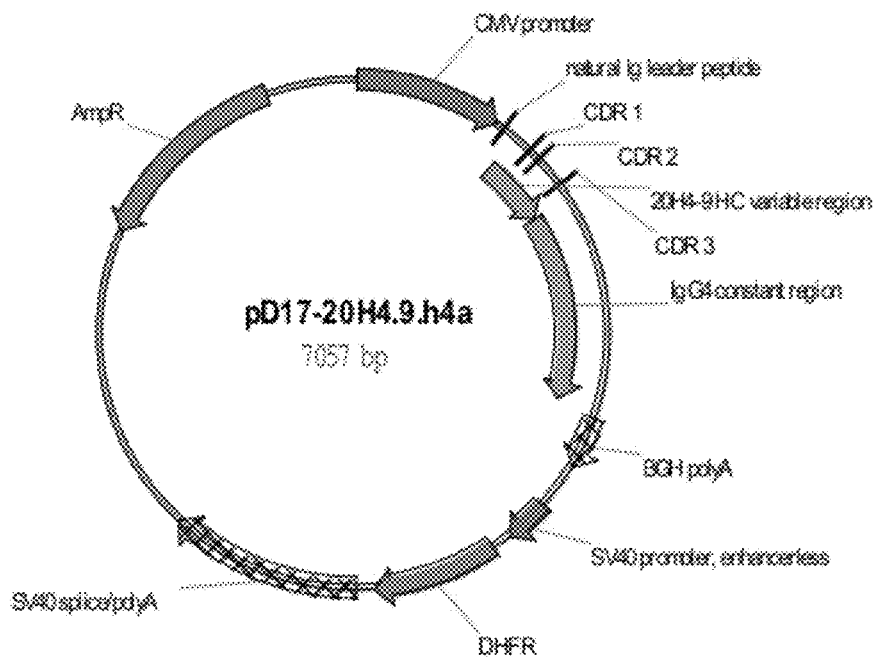
Figure 2:
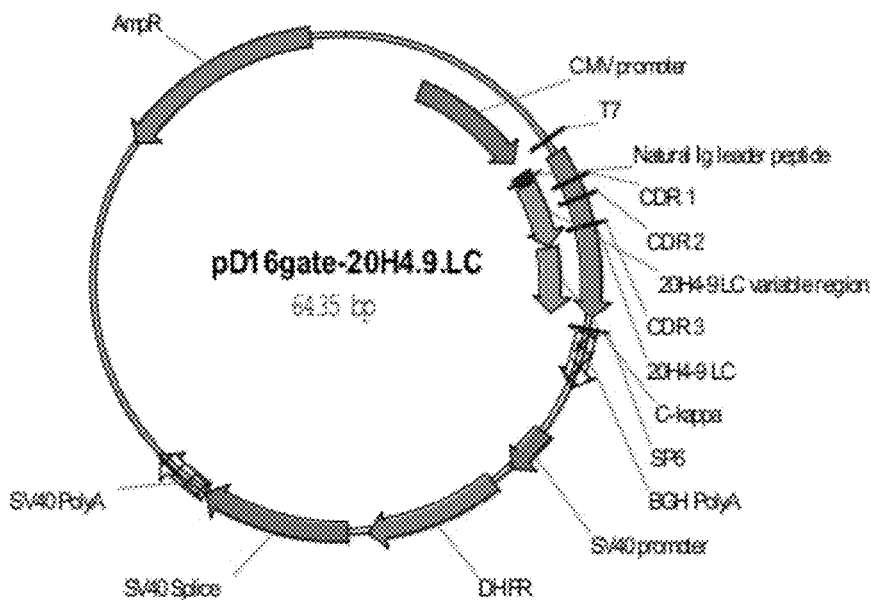
FIG. 2 shows a plasmid map of pD16gate-20H4.9.LC.
Figure 3E:
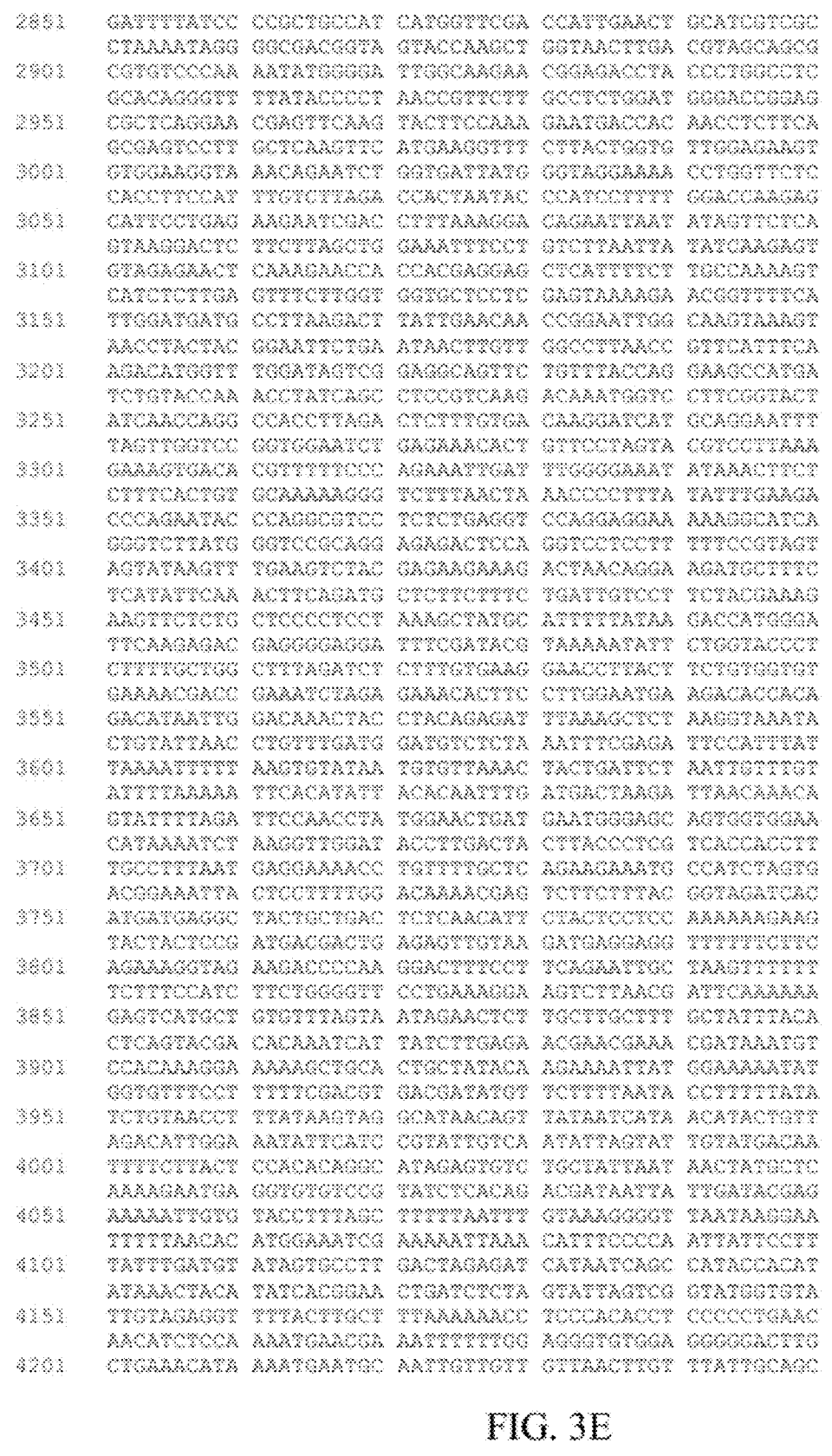
Figure 4C:
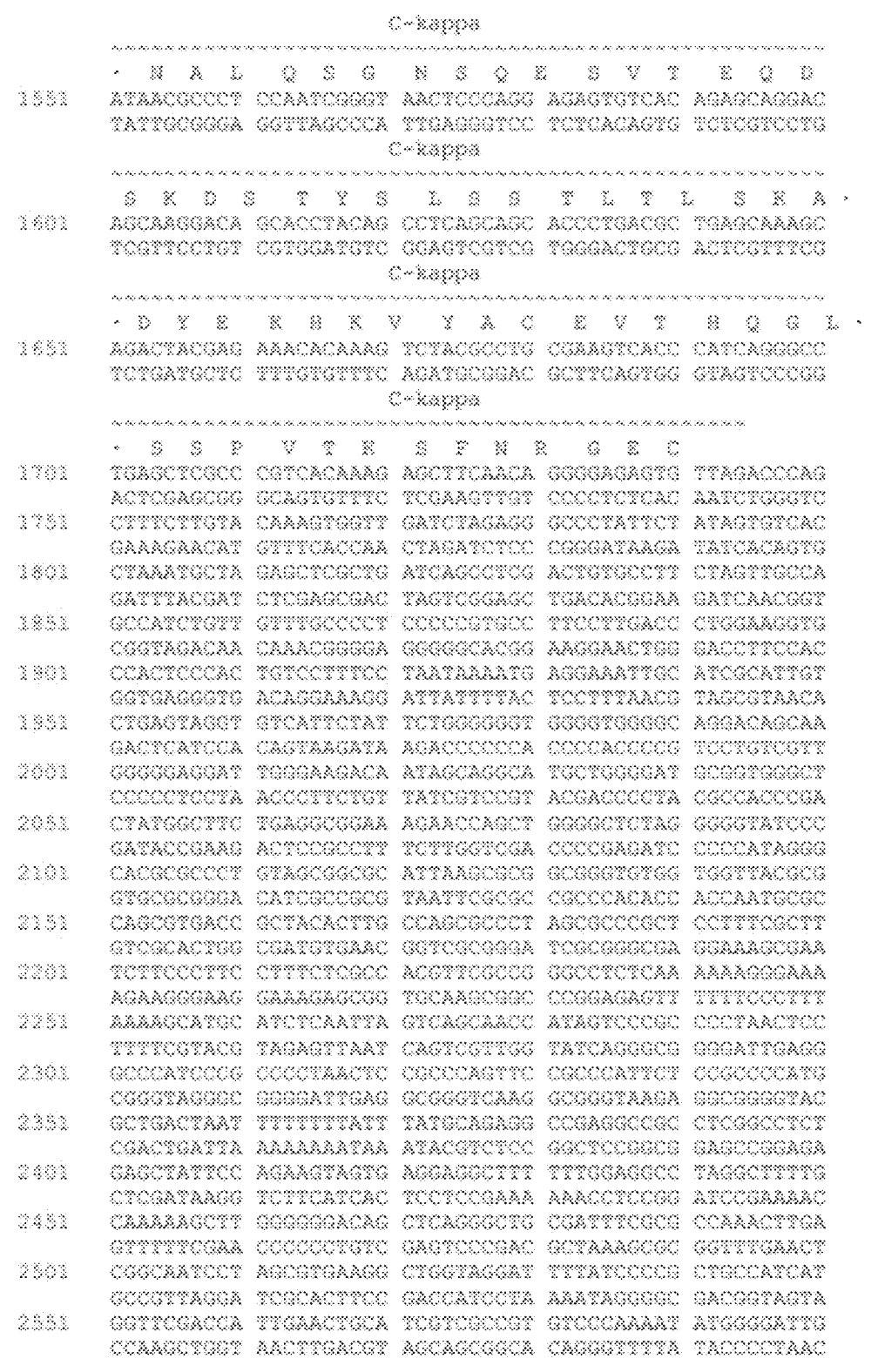

In one aspect, the invention provides the monoclonal antibody (mab) 20H4.9-IgG4. FIGS. 1 and 2 provide plasmid maps of pD17-20H4.9.h4a and pD16gate-20H4.9.LC, respectively, that can be used to produce mab 20H4.9-IgG4. FIG. 3 (FIGS. 3A-3H) provides the nucleotide sequence of the plasmid pD17-20H4.9.h4a, including the coding strand (SEQ ID NO:1), complementary strand (SEQ ID NO:2), and amino acid sequence (leader peptide is amino acid residues 1-19 of SEQ ID NO:3; heavy chain is amino acid residues 20-467 of SEQ ID NO:3) encoded by the coding strand. FIG. 4 (FIGS. 4A-4F) shows the nucleotide sequence of the plasmid pD16gate-20H4.9.LC, including the coding strand (SEQ ID NO:4), complementary strand (SEQ ID NO:5), and amino acid sequence (leader peptide is amino acid residues 1-20 of SEQ ID NO:6; light chain is amino acid residues 21-236 of SEQ ID NO:6) encoded by the coding strand.

Figure 5:
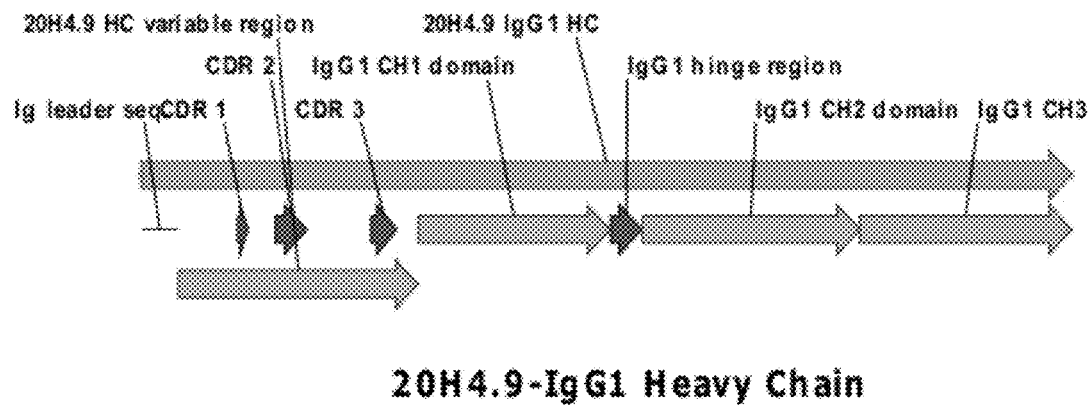
FIG. 5 shows a schematic of the 20H4.9-IgG1 heavy chain sequence construct.
Figure 6:
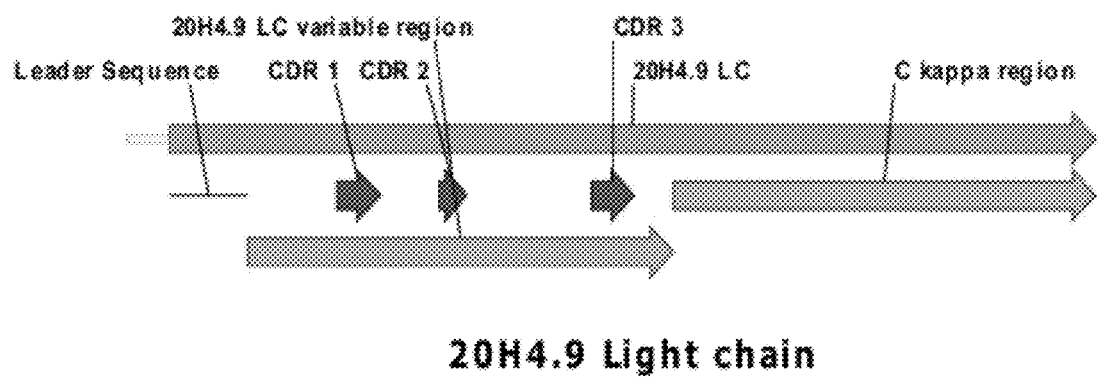
FIG. 6 shows a schematic of the 20H4.9 light chain sequence construct.
Figure 7B:
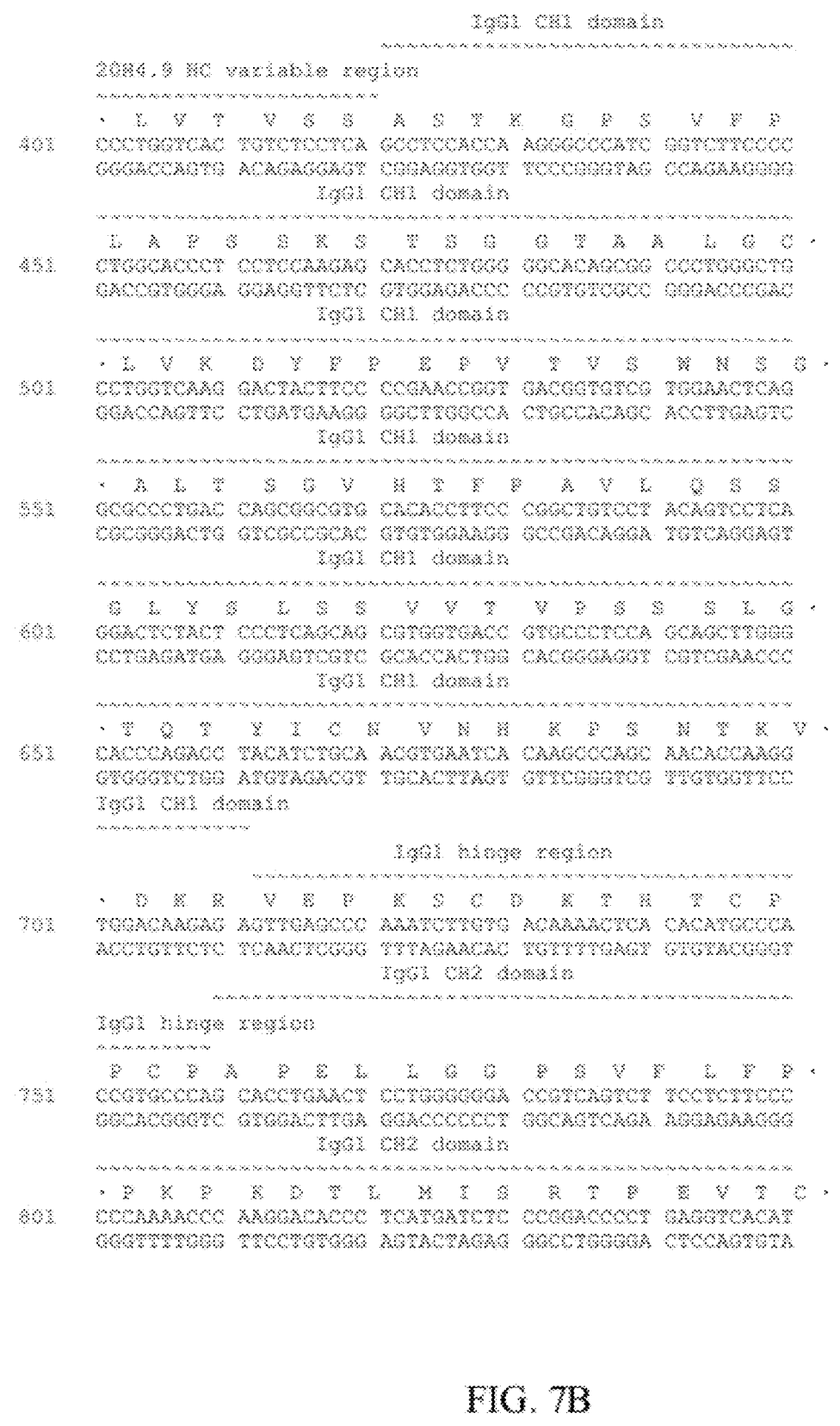

In another aspect, the invention provides the monoclonal antibody (mab) 20H4.9-IgG1. FIG. 5 schematically shows a heavy chain sequence construct of mab 20H4.9-IgG1. FIG. 6 schematically shows a light chain sequence construct of mab 20H4.9, for both mab 20H4.9-IgG4 and 20 H4.9-IgG1. FIG. 7 provides the nucleotide sequence (coding strand (SEQ ID NO:7) and complementary strand (SEQ ID NO:8)) of the heavy chain sequence construct of FIG. 5, and the amino acid sequence (leader peptide is amino acid residues 1-19 of SEQ ID NO:9; heavy chain is amino acid residues 20-470 of SEQ ID NO:9) encoded by the coding strand. The light chain of mab 20H4.9-IgG1 is the same as the light chain of mab 20H4.9-IgG4.

The invention also encompasses antibodies with conservative amino acid substitutions from the heavy and light chain amino acid sequences depicted in SEQ ID NOS:3, 6, and 9 that have substantially no effect on H4-1BB binding. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine.

The polynucleotides encoding the polypeptides of the invention typically further comprise an expression control sequence operably linked to the polypeptide coding sequences, including naturally-associated or heterologous promoter regions. Preferably, the expression control sequences will be eukaryotic promoter systems in vectors capable of transforming or transfecting eukaryotic host cells, but control sequences for prokaryotic hosts may also be used. Once the vector has been incorporated into an appropriate host, the host is maintained under conditions suitable for high level expression of the nucleotide sequences and, as desired, the collection and purification of the light chain, heavy chain, light/heavy chain dimers or intact antibody, binding fragments or other immunoglobulin form may follow. (See, S. Beychok, Cells of Immunoglobulin Synthesis, Academic Press, N.Y. (1979)). Single chain antibodies or minibodies (single chain antibodies fused to one or more CH domains) may also be produced by joining nucleic acid sequences encoding the VL and VH regions disclosed herein with DNA encoding a polypeptide linker.

Prokaryotic hosts, such as E. coli, and other microbes, such as yeast, may be used to express an antibody of the invention. In addition to microorganisms, mammalian tissue cell culture may also be used to express and produce the antibodies of the invention. Eukaryotic cells may be preferred, because a number of suitable host cell lines capable of secreting intact immunoglobulins have been developed including, for example, CHO (chinese hamster ovary) cell lines, COS (African green monkey fibroblast cell line) cell lines, HeLa cells, myeloma cell lines, and hybridomas. Expression vectors for these cells can include expression control sequences, such as a promoter or enhancer, and necessary processing information sites, such as ribosome binding sites, RNA splice sites, polyadenylation sites, and transcriptional terminator sequences, all well known in the art.

The vectors containing the DNA segments of interest (e.g., the heavy and/or light chain encoding sequences and expression control sequences) can be transferred into the host cell by well-known methods, which vary depending on the type of cellular host. For example, calcium chloride transfection is commonly used for prokaryotic cells, whereas calcium phosphate treatment, lipofection, or electroporation may be used for other cellular hosts. (See, e.g., T. Maniatis et al., Molecular Cloning: A Laboratory Manual, Cold Spring Harbor Press (1982)).

Once expressed, the antibodies, their dimers, individual light and heavy chains, or other immunoglobulin forms, can be purified according to standard procedures in the art, such as ammonium sulfate precipitation, affinity columns, column chromatography, gel electrophoresis, and the like. Substantially pure immunoglobulins of at least 90 to 95% homogeneity are desirable, and 98 to 99% or more homogeneity are more desirable.

The antibodies of the invention are useful for modulating T cell and antibody-mediated immune responses. Typical disease states suitable for treatment include cancers, infectious diseases, inflammatory diseases, and autoimmune diseases such as multiple sclerosis, rheumatoid arthritis, systemic lupus erythematosus, and myaesthenia gravis.

The invention also provides pharmaceutical compositions comprising at least one antibody of the invention and a pharmaceutically acceptable carrier. The pharmaceutical compositions may be sterilized by conventional well known sterilization techniques. The pharmaceutical compositions can also contain pharmaceutically acceptable auxiliary substances as required to approximate physiological conditions such as pH adjusting and buffering agents, stability enhancing agents such as mannitol or tween 80, toxicity adjusting agents and the like, for example, sodium acetate, sodium chloride, potassium chloride, calcium chloride, sodium lactate, or human albumin.

The antibodies and pharmaceutical compositions of the invention are particularly useful for parenteral administration, including subcutaneous, intramuscular, and intravenous administration. The pharmaceutical compositions for parenteral administration can comprise a solution of the antibody dissolved in an acceptable carrier, preferably an aqueous carrier. A variety of aqueous carriers can be used, all well known in the art, e.g., water, buffered water, saline, glycine and the like. These solutions are sterile and generally free of particulate matter. It is especially advantageous to formulate parenteral compositions in dosage unit form for ease of administration and uniformity of dosage.

The pharmaceutical composition can further comprise an additional agent for treatment of a disease. In one aspect, the pharmaceutical composition includes an agent for treatment of a cancer, an infectious disease, inflammatory disease, or autoimmune disease. The antibody of the invention can also be co-administered or separately administered with an additional agent for treatment of a disease.

The antibodies of the invention can be used with other agents to enhance the immune response to cancerous cells in a patient. In one aspect, the antibody is used in combination with an immunogenic agent, such as cancerous cells, purified tumor antigens (including recombinant proteins, peptides, and carbohydrate molecules), or cells transfected with genes encoding immune stimulating cytokines and cell surface antigens. In another aspect, the antibody is used in combination with a vaccine such as, for example, a tumor cell vaccine, a DNA vaccine, a gene-modified tumor cell vaccine, such as GM-CSF-modified tumor cell vaccine, a peptide vaccine, or an antigen-loaded dendritic cell vaccine.

Many experimental strategies for vaccination against tumors have been devised. In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al., P.N.A.S., 90:3539-43 (1993); E. Jafee et al., J. Clin. Oncol., 19:145-56 (2001); R. Salgia et al., J. Clin. Oncol., 21:624-30 (2003)).

The study of gene expression and large scale gene expression patterns in various tumors has led to the definition of so called tumor specific antigens (S. Rosenberg, Immunity 10:281-7 (1999)). In many cases, these tumor specific antigens are differentiation antigens expressed in the tumors and in the cell from which the tumor arose, for example melanocyte antigens gp 100, MAGE antigens, Trp-2. Many of these antigens can be shown to be the targets of tumor specific T cells found in the host. The antibodies of the invention may be used in conjunction with a collection of recombinant proteins and/or peptides expressed in a tumor in order to amplify and direct the immune response to these antigens towards a Th1 response. These proteins are normally viewed by the immune system as self antigens and are therefore tolerant to them.

In one aspect of the invention, the antibody is combined with an immunodulatory agent comprising the SIV gag antigen (as a model for HIV DNA vaccine) or prostate specific antigen (PSA), or a DNA vaccine comprising a nucleotide sequence that encodes the SIV gag antigen or prostate specific antigen (PSA). PSA vaccines are described in, for example, M. Pavlenko et al., Br. J. Cancer, 91(4):688-94 (2004); J. Wolchok et al., Semin. Oncol., 30(5):659-66 (2003); J. Kim et al., Clin. Cancer Res., 7(3 Suppl.):882s-889s (2001). SIV gag vaccines are described in, for example, B. Makitalo et al., J. Gen. Virol., 85(Pt 8):2407-19 (2004); N. Letvin et al., J. Virol., 78(14):7490-7 (2004); S. Mossman et al., AIDS Res. Hum. Retroviruses., 20(4):425-34 (2004); F. Bertley et al., J.

Immunol., 172(6):3745-57 (2004); L. Patterson et al., J. Virol., 78(5):2212-21 (2004); E. O'Neill et al., AIDS Res. Hum. Retroviruses, 19(10):883-90 (2003); Z. Bu et al., Virology, 309(2):272-81 (2003).

The tumor antigen may also include, for example, the protein telomerase, which is required for the synthesis of telomeres of chromosomes and which is expressed in more than 85% of human cancers and in only a limited number of somatic tissues (N. Kim et al., Science, 266, 2011-2013 (1994)). Tumor antigen may also be "neo-antigens" expressed in cancer cells because of somatic mutations that alter protein sequence or create fusion proteins between two unrelated sequences, or idiotype from B cell tumors. Other tumor vaccines may include the proteins from viruses implicated in human cancers such a Human Papilloma Viruses (HPV), Hepatitis Viruses (HBV and HCV), and Kaposi's Herpes Sarcoma Virus (KHSV). Another form of tumor specific antigen which may be used with an antibody of the invention is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (R. Suot et al., Science 269: 1585-1588 (1995); Y. Tamura et al., Science 278: 117-120 (1997)).

The antibodies of the invention can also be used to enhance the immune response to vaccines to viral antigens, such as HIV or HCV. The antibodies of the invention can also be used to enhance the immune response to other immunomodulatory agents, and to elicit a memory immune response. Examples of these agents are cytokines such as GM-CSF, IL-2, IL-15, IL-12, F13 ligand, CD40 ligand, adjuvants such as CpG-oligodeoxynucleotide (bacterial DNA), or antibodies to OX-40 or CTLA-4.

The pharmaceutical compositions of the invention can be administered for prophylactic and/or therapeutic treatments. In therapeutic application, the pharmaceutical composition is administered to a patient already suffering from a disease, in an amount sufficient to cure or at least partially arrest or treat the disease. An amount adequate to accomplish this is defined as a "therapeutically effective dose." Amounts effective for this use will depend upon the severity of the disease state and the patient (including, for example, the general state of the patient's own immune system), and can be determined by one skilled in the art. In prophylactic applications, the pharmaceutical composition is administered to a patient not already in the disease state, to enhance the patient's resistance to the disease state. Such an amount is defined to be a "prophylactically effective dose." In this use, the precise amounts depend upon the patient's state of health (including, for example, the general state of the patient's own immune system), and can be determined by one skilled in the art. In one aspect, the prophylactic use is for the prevention of tumor recurrence.

EXAMPLES

Example 1

Generation of Antibodies

Materials and Methods

Fully human monoclonal antibodies to the human CD137 (4-1BB) receptor were generated in the HuMAb-Mouse® (Medarex, Inc., Princeton, N.J.). HuMAb mice were immunized five times intraperitoneally (i.p.) and subcutaneously (s.c.) with 25 μg of the extracellular domain of human CD137 in RIBI adjuvant (Ribi Immunochemical). Prior to fusion, mice were boosted intravenously (i.v.) with the same amount of antigen. Spleen cells from immunized mice with adequate titers of antibodies to huCD137 were fused to mouse myeloma cells following standard procedures.

Anti-human CD3 mab (clone:HIT3a), ELISA kits for human and monkey IFN-γ, cytometric bead array (CBA) kits, and all conjugated antibodies for flow cytometry were purchased from BD Pharmingen (San Diego, Calif.). Human $IgG_1\lambda$ and Human $IgG_1\kappa$ were purchased from Sigma-Aldrich (St. Louis, Mo.). CEM cells (ATCC-CRL 2265) were purchased from ATCC. Culture media (RPMI), and fetal bovine serum (FBS) were purchased from Mediatech Inc. (Herndon, Va.). Sheep Red Blood Alsevers was purchased from Colorado Serum Co. (Denver, Colo.).

Hybridoma screening: Detection of binding to huCD137 by ELISA: To identify hybridomas secreting anti-human CD137 antibodies, ELISA plates (Nunc MaxiSorp) were coated with human CD137-mouse $IgG_{2b}$ fusion protein at 1 μg/ml in PBS overnight at 4° C. Plates were then washed 3 times with PBS with 0.01% Tween-80 (PBS-T), and subsequently blocked with PBS-T plus 1% bovine serum albumin (BSA), for 20 min at room temperature. Fifty microliters of supernatants diluted 1:3 in PBS-T were added to the plates and incubated for 1-2 hr at ambient temperature. Afterwards, plates were washed as before, and binding of antibodies was detected by an incubation with alkaline phosphatase-conjugated goat $F(ab')_2$ anti-human IgG antibody (Jackson Laboratories, West Grove, Pa.). Plates were developed with pNPP and read at 405 nm.

Blocking assay: Twenty-six hybridomas secreting antibodies that recognized huCD137 by ELISA were evaluated for their ability to allow CD137-CD137L interactions. These analyses were conducted initially in an ELISA format. Plates were coated with human CD137-muIgG$_{2b}$ at 0.2 μg/ml, 100 μl/well. Serial dilutions of the mab 20H4.9-IgG1, or control antibodies, diluted in PBS-T and 1% bovine serum albumin, were added to the plate. CD137L-CD8 fusion protein was added to the wells at a concentration of 0.2 μg/ml. Binding of antibodies was detected with a biotinylated anti-CD8 antibody (0.2 μg/ml, Ancell Corporation, Bayport, Minn.). After several washes, streptavidin-alkaline phosphatase (1:2000) and pNPP for the detection of bound antibodies were added, and the plates were read at 405 nm.

To confirm that the selected antibodies did not alter CD137-CD137L binding, purified antibodies were further characterized by BIAcore analyses. All experiments were carried out on a BIAcore 3000 instrument (BIAcore Inc., Piscataway, N.J.). Human CD137 was immobilized covalently at a high density on a carboxy-methylated dextran surface of a BIAcore sensorchip (BIAcore Inc., Piscataway, N.J.). Injections were conducted at 2 μg/mL in 10 mM acetate buffer, pH 5.0. Unoccupied active esters were subsequently blocked by injection of an excess of ethanolamine Regeneration of the surface was done with 10 mM glycine, pH 2.0.

Purified samples of anti-CD137 antibodies were diluted to concentrations between 200 and 1000 nM using HEPES buffered saline, pH 7.4, supplemented with 0.15 M NaCl and 0.005% surfactant P20 (HBS-EP). Human CD137L-CD8 fusion proteins (huCD137L) were used as source of CD137 ligand. Experiments were conducted in which huCD137L was injected prior to anti-CD137 antibodies, or vice versa. Injections were performed at a flow rate of 5 μL/min. Bound ligand and antibodies were removed by regeneration with 10 mM glycine buffer, pH 2.0.

Human T-cell purification: T-cells or PBMCs were obtained from healthy human donors. Blood was collected in EDTA, suspended in elutriation buffer (RPMI containing 2.5 mM EDTA, 10 μg/ml polymyxin B), underlayed with Lymphocyte Separation Medium (LSM, Mediatech Inc., Herndon, Va.), and centrifuged at 1800 rpm for 25 minutes. Cellular interfaces were collected, and centrifuged at 1500 rpm for 10 minutes. Afterwards, cell pellets were resuspended in elutriation buffer and washed Sheep Red Blood Cells (SRBC, 1:10 dilution), and incubated on ice for 1 hour. Cells were then underlayed with LSM and centrifuged at 2500 rpm for 25 minutes. Interfaces were removed and SRBC were lysed with SRBC Lysis Buffer. Isolated T-cells were washed and resuspended in 10% FBS/RPMI.

Flow Cytometric analyses: Binding of anti-human CD137 antibodies to CD137 expressed on cells was determined by flow cytometry. A human T-cell leukemia cell line (CEM) or cynomolgus monkey peripheral blood monocytic cells (PBMC) were used for these studies. These cells do not express CD137 constitutively, but the receptor can be induced by stimulation with phorbol myristate (PMA, 10 ng/ml) and ionomycin (1 μM) for 18 hr. Cells were then washed and incubated with various concentrations of the antibodies in staining buffer (phosphate buffer saline, PBS, plus 1% FCS, and 0.01% sodium azide). Binding of the antibodies to stimulated or non-stimulated cells was detected by a fluorescein (FITC) or phycoerthrin (PE) conjugated goat anti-human IgG (Jackson Immunoresearch, West Grove, Pa.). To confirm expression of CD137, a fusion protein consisting of the extracellular domain of CD137 ligand and mouse CD8 was used (Ancell Corporation, Bayport, Minn.), followed by incubation with PE-conjugated anti-mouse CD8 (BD Pharmingen, San Diego, Calif.). Samples were fixed in 1% formalin, kept at 4° C., and read by flow cytometry.

Functional assays: Primary human T-cells or monkey PBMC obtained from healthy donors were stimulated with immobilized anti-CD3 antibody to provide the first signal for T-cell activation, and co-stimulated with human anti-human CD137 antibodies. As a non-specific control, a humanized anti-carcinoma antibody (BR96) was used at the same antibody concentration. Plates were coated with anti-CD3 antibody (0.5-1 μg/ml) at 4° C. overnight. The next day T-cells or PBMC were plated at 1–1.5×10$^5$/well concentrations. Synthesis of IFN-γ was measured after 72 hours of culture at 37° C. either by cytometric bead array (CBA) or by ELISA.

Cytokine Assays

ELISA: After stimulation of T-cells at various times, plates were centrifuged and media was removed. Cytokine levels were detected by an ELISA in accordance with the manufacturer's instructions (BD Pharmingen, San Diego, Calif.). In brief, test samples and standards were added to anti-cytokine-coated 96-well plates. After incubation for 2 hr at ambient temperature, plates were washed 3 times in PBS-T and then incubated first with a working detector antibody, followed by the addition of substrate. Absorbance was read at 405 nm, and concentrations were calculated based on the standard curve.

Cytometric Bead Array: Another method used to determine cytokine production in vitro was flow cytometry using the Cytometric Bead array (CBA) developed by BD Pharmingen. Levels of IFN-γ, IL-2, IL-5, IL-4, IL-10, and TNF-α were measured in culture supernatants following manufacturers' instructions. Results were analyzed by flow cytometry with the CBA analysis software.

Results

Figure 8A:
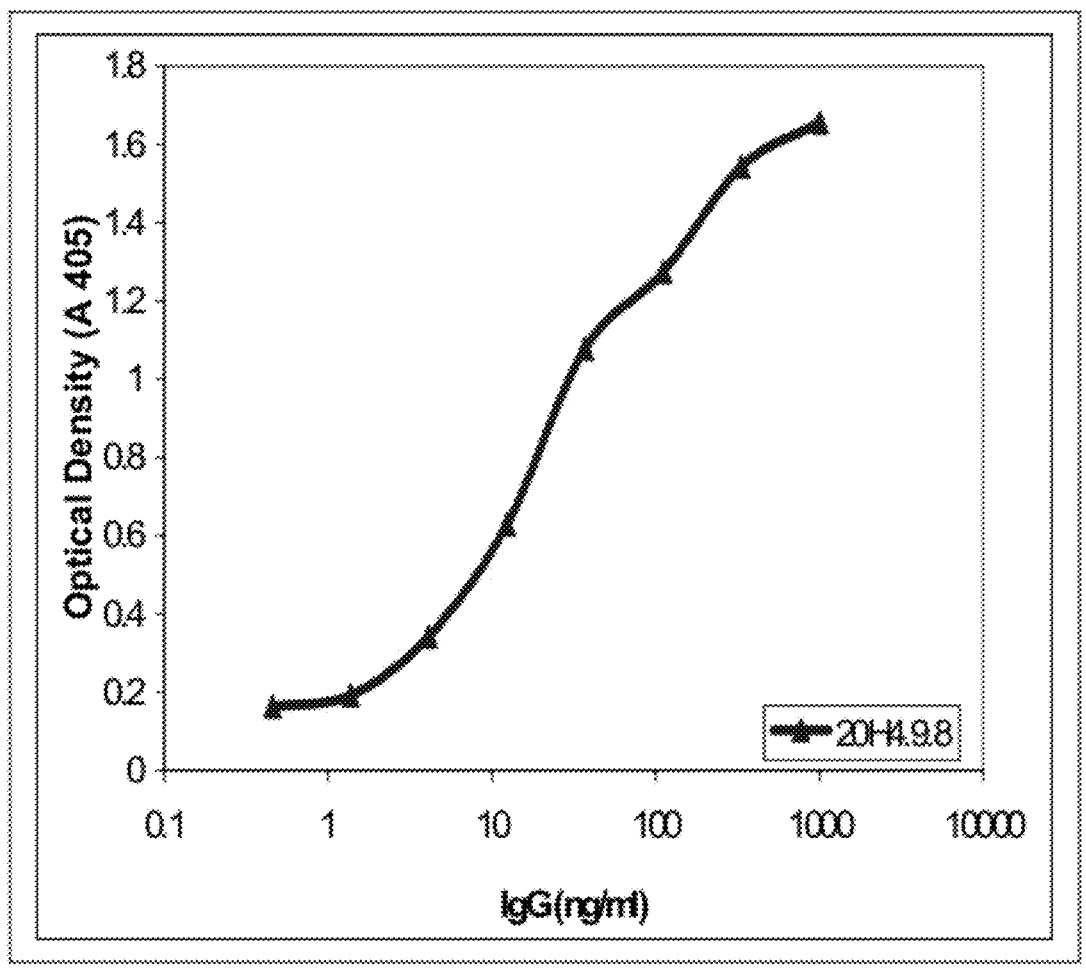
FIG. 8 (FIGS. 8A-8B) illustrates the results obtained from the binding of mab 20H4.9-IgG1 to human CD137 by ELISA (FIG. 8A) and the effect of mab 20H4.9-IgG1 on CD137-CD137L interaction (FIG. 8B).
Figure 8B:
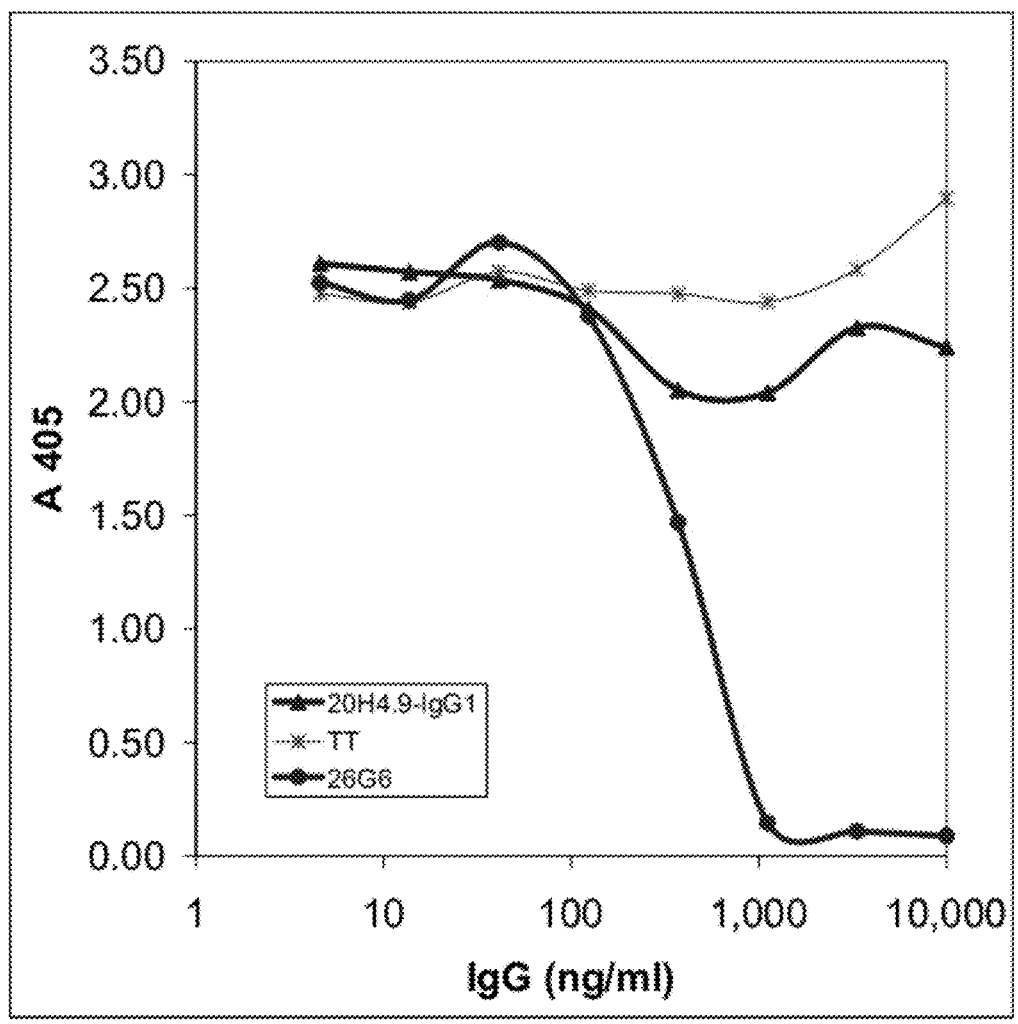

Hybridomas secreting antibodies that showed binding to human CD137 were further expanded, and subcloned. Secreted antibodies were purified and tested for their ability to bind to huCD137 and to allow the interaction of CD137-CD137L. Of the panel of anti-human CD137 antibodies evaluated, mab 20H4.9-IgG1 was selected for further evaluation based on its binding profile and non-blocking properties. The 20H4.9-IgG1 antibody is IgG1 kappa as determined by ELISA using alkaline phosphatase anti-human IgG1, 2, 3, 4, and anti-kappa and lambda reagents (Southern Biotech, Birmingham, Ala.). FIG. 8 (FIG. 8A-*binding* to human CD137 by ELISA; FIG. 8B-*effect* of mab 20H4.9-IgG1 on CD137-CD137L interaction) provides the initial characterization of mab 20H4.9-IgG1. Serial dilutions of mab 20H4.9-IgG1, 26G6 (a blocking anti-CD137 antibody), or tetanus toxoid (TT, negative control) were evaluated for their ability to alter binding of CD137 to CD137L. Mab 20H4.9-IgG1 at concentrations up to 10 μg/ml did not block CD137L binding, whereas mab 26G6 inhibited binding at concentrations >0.37 μg/ml.

Figure 9A:
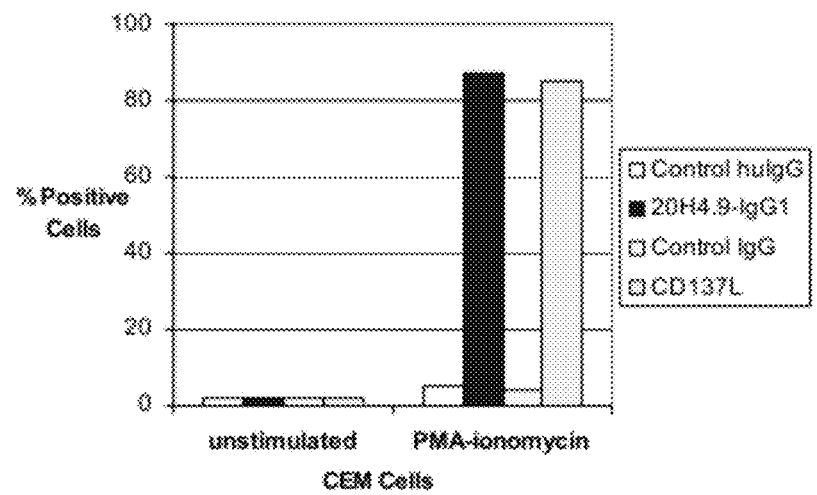
FIG. 9 (FIGS. 9A-9B) illustrates the results obtained from the binding of mab 20H4.9-IgG1 to PMA-ionomycin stimulated human or cynomolgus monkey cells. Human CEM (FIG. 9A) or monkey PBMC (FIG. 9B) were incubated with 20H4.9-IgG1 or human CD137L fusion protein.
Figure 9B:
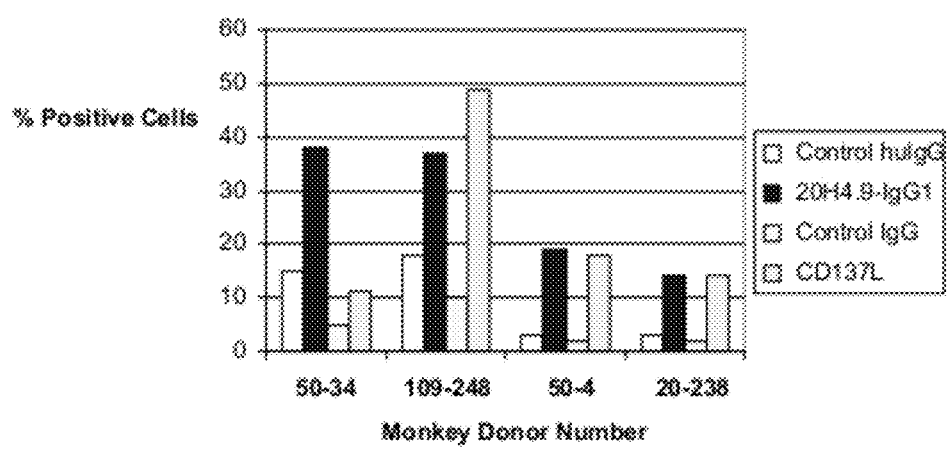

Mab 20H4.9-IgG1 was also tested for reactivity towards CD137 expressed on human T-cells (CEM) and in cynomolgus monkey peripheral blood monocytic cells (PBMC) stimulated with PMA and ionomycin. Previous studies determined that CD137 is upregulated on T-cells following activation with PMA and ionomycin. Control molecules consisted of an irrelevant human IgG antibody (negative control) or CD137L-CD8 fusion protein (positive control, BD Pharmingen, San Diego, Calif.). Results from these studies indicated that mab 20H4.9-IgG1 bound to activated human CEM and PBMCs from cynomolgus monkeys, with minimum binding to unstimulated cells. Similar percentages of positive cells were detected with either mab 20H4.9-IgG1 or CD137L. FIG. 9 provides the results obtained demonstrating the binding of mab 20H4.9-IgG1 to PMA-ionomycin stimulated human or cynomolgus monkey cells. Human CEM (FIG. 9A) or monkey PBMC (FIG. 9B) were incubated with 20H4.9-IgG1 or human CD137L fusion protein. Secondary antibodies were added and samples were read by flow cytometry.

Figures 10A, 10B:
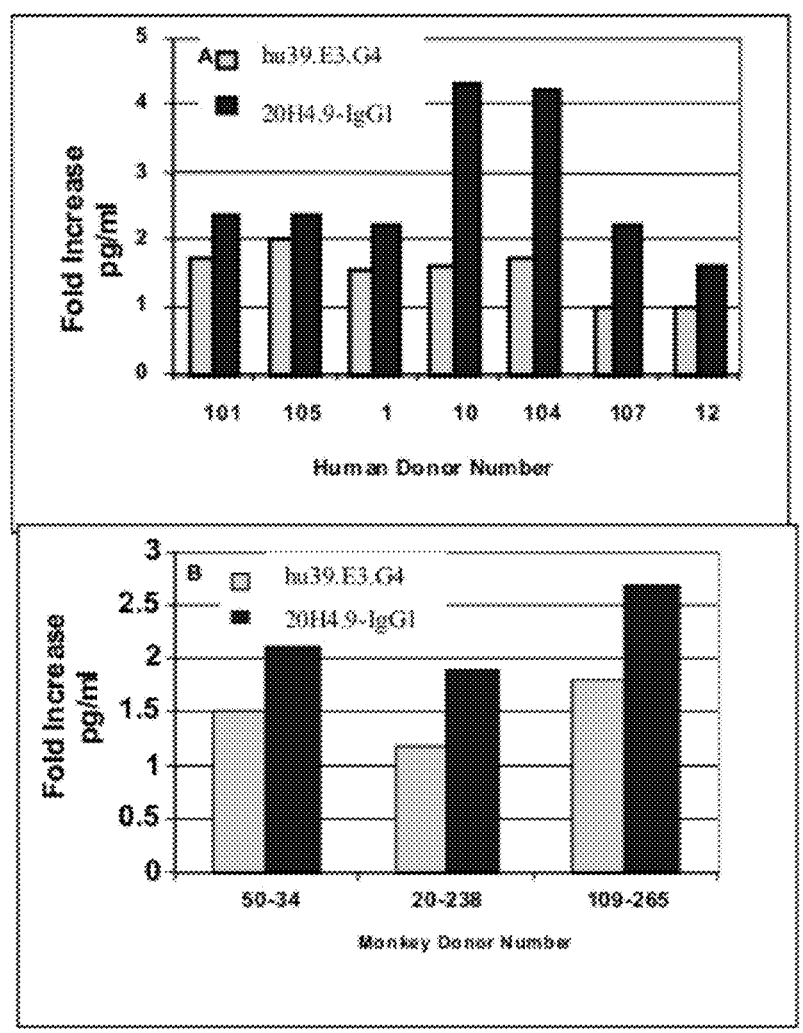
FIG. 10 (FIGS. 10A-10B) illustrates the results obtained by induction of IFN-γ in co-stimulatory studies with anti-CD137 antibodies, which are expressed as fold increase in pg/ml over controls. Due to the variable background response among donors, data was normalized relative to control treatments (=1). Median IFN-γ baseline level for human T-cells (FIG. 10A) or monkey PBMC (FIG. 10B) stimulated with anti-CD3 alone was 592 pg/ml and 505 pg/ml respectively.

Next, it was determined whether mab 20H4.9-IgG1 could induce enhancement of IFN-γ in costimulatory assays in the presence of anti-CD3 stimulation, the key functional effect desired for an agonistic CD137 antibody. Mab 20H4.9-IgG1 was evaluated for its co-stimulatory activity in functional studies in human and monkey lymphocytes. Based on initial data, a concentration of 20 ug/ml anti-CD137 antibody (excess antibody) was used in these studies. Levels of anti-CD3 antibody between 0.2-1 μg/ml were tested which resulted in 10-20% CD137-positive lymphocytes. Levels of IFN-γ in supernatants were measured after 72 h of culture. As shown in FIG. 10, mab 20H4.9-IgG1 enhanced IFN-γ synthesis in both human and monkey costimulatory assays to levels significantly higher than controls. Results of studies conducted with T-cells isolated from 8 healthy human donors showed that in six of them, mab 20H4.9-IgG1 enhanced IFN-γ synthesis between 2.2-4.3-fold compared to controls. One of the other two donors showed a 1.6-fold increase. The level of enhancement was superior to that observed with hu39E3.G4, a humanized anti-CD137 antibody provided in published PCT Application WO04/010947 (herein incorporated by reference) which showed augmentation of IFN-γ in 5 out of 8 donors and at levels lower than mab 20H4.9-IgG1 (1.5-2-fold increase) (FIG. 10A). In monkey costimulatory studies, mab 20H4.9-IgG1 also demonstrated enhanced functional activity resulting in significant augmentation of IFN-γ over controls (FIG. 10B). As in the human studies, enhancement of IFN-γ was consistently higher than with hu39E3.G4.

Induction of TNF-α synthesis above control levels was also observed in human cultures, albeit at much lower levels than IFN-γ. TNF-α levels induced by anti-CD3 antibody alone (baseline) were about 20-50 fold lower than baseline levels for IFN-γ. Mab 20H4.9-IgG1 induced an increase of ~2 to 4.7-fold in 3 out of 8 donors. Again, hu39E3.G4 (tested in parallel) induced ~2-fold increase in the same donors but at lower levels. Other cytokines tested, IL-2, IL-5, IL-10, and IL-4 did not change significantly with either treatment.

Together these studies demonstrated that mab 20H4.9-IgG1 presented the functional activity desired in both humans and monkeys by inducing a Th1-type of response. Significantly, since in vivo anti-tumor activity is associated with the ability of anti-CD137 antibodies to induce IFN-γ synthesis, these results supported the selection of mab 20H4.9-IgG1 for isotype switching.

Example 2

In Vitro Characterization of Mab 20H4.9-IgG4

Based on its binding kinetics, inability to block CD137-CD137L interaction, and functional effects on human T-cells, mab 20H4.9-IgG1 was selected for switching to an IgG4 form. The IgG4 form of mab 20H4.9-IgG1 is 20H4.9-IgG4 (depicted in FIGS. 3 and 4).

The second phase of these studies involved the comparison of the in vitro properties of mab 20H4.9-IgG4 and mab 20H4.9-IgG1. In this section, the binding kinetic properties, and functional effects of both antibodies in human and monkey lymphocytes are described.

Binding Kinetics

Figure 11:
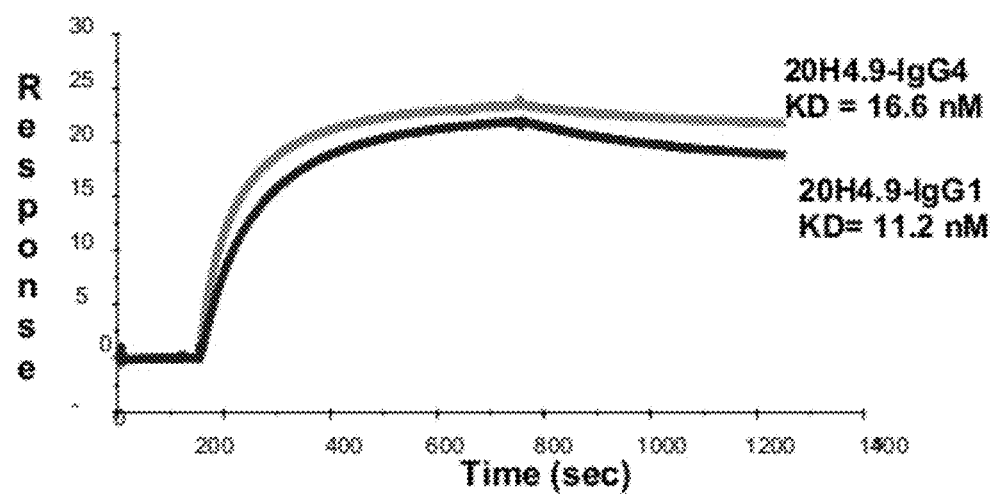
FIG. 11 provides plasmon resonance plots of binding of mab 20H4.9-IgG4 and mab 20H4.9-IgG1 to human CD137.

Kinetic properties of anti-human CD137 antibodies were evaluated by surface plasmon resonance using a BIAcore 3000 instrument. The antigen, human CD137-murine $IgG_{2a}$, was immobilized covalently at a low density on the surface of a CM5 sensorchip. Mab 20H4.9-IgG4 and mab 20H4.9-IgG1 were injected at concentrations between 25 and 200 nM. FIG. 11 depicts injections at 100 nM for both mab 20H4.9-IgG1 and mab 20H4.9-IgG4. Data calculated using BIAevaluation software (bivalent model, global curve fit analysis) resulted in kinetic parameters that were similar for both antibodies (see Table 1). Dissociation constants $K_D$ for mab 20H4.9-IgG1 and mab 20H4.9-IgG4 were determined as 11.2 and 16.6 nM, respectively. Under similar experimental conditions, mab 20H4.9-IgG4 did not bind to murine 4-1BB.

Figure 13A:
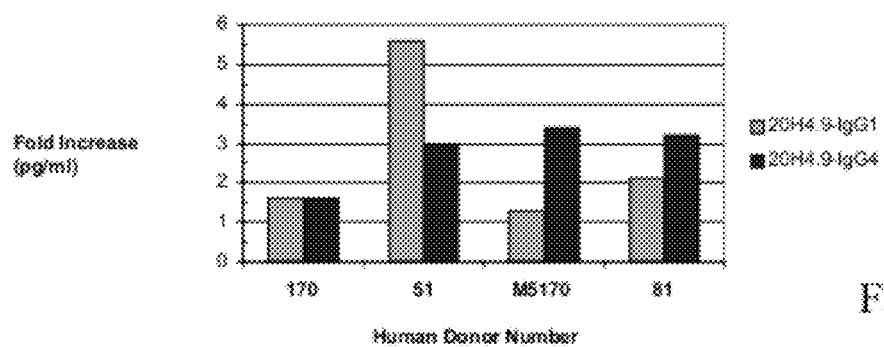
FIG. 13 (FIGS. 13A-B) illustrates the induction of IFN-γ in co-stimulatory studies with anti-CD137 antibodies. The results are expressed as fold increase in pg/ml over controls. Due to the variable background response among donors, data was normalized relative to control treatments (=1). Median IFN-γ baseline level for human T-cells (FIG. 13A) or monkey PBMC (FIG. 13B) stimulated with anti-CD3 alone was 592 pg/ml and 505 pg/ml respectively.
Figure 13B:
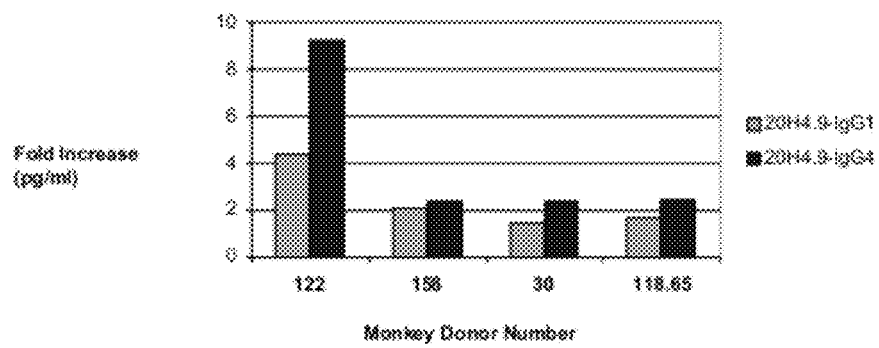

PBMC and human T-cells. The functional effects of mab 20H4.9-IgG4 on human and monkey T-cells or PBMC were determined and compared to its parental molecule, mab 20H4.9-IgG1. Primary human T-cells or monkey PBMC obtained from healthy donors were stimulated with anti-CD3 antibody (0.5 μg/ml-1 μg/ml)+/−anti-human CD137 antibodies. Synthesis of IFN-γ was measured after 72 h of culture at 37° C. by cytometric bead array (CBA) for human samples or by ELISA for monkey samples. Antibodies were tested in costimulatory assays in the presence of suboptimal concentrations of anti-CD3 antibody (1 μg/ml) or Concavalin A (1 μg/ml) (donors M5170 and 81 only). Results are expressed as fold increase in pg/ml over controls. Due to the variable background response among donors, data was normalized relative to control treatments (=1). FIG. 13A provides the human T-cell results and FIG. 13B provides the monkey PBMC results. As shown in FIGS. 13A-13B, mab 20H4.9-IgG4 demonstrated costimulatory properties yielding higher levels of IFN-γ in human and monkey cells compared to controls. The level of enhancement of IFN-γ synthesis was comparable to its parental molecule in human and monkey samples.

Figure 14A:
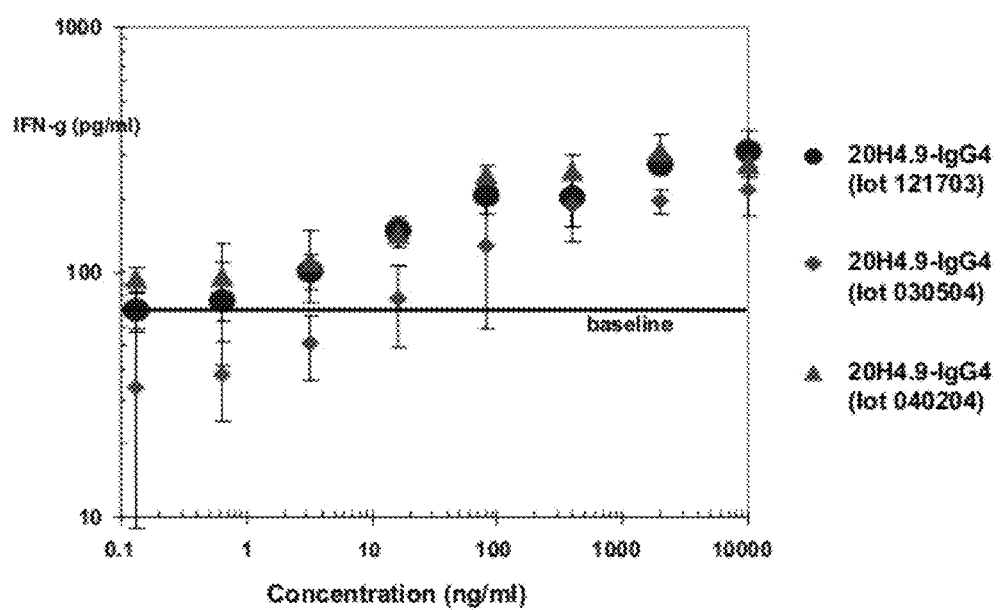
FIG. 14 (FIGS. 14A-14B) illustrates the results obtained of dose-dependent enhancement of IFN-γ synthesis by mab 20H4.9-IgG4 (FIG. 14A), and effect of antibody crosslinking by addition of crosslinking anti-human IgG antibody (7 μg/ml) (FIG. 14B).
Figure 14B:
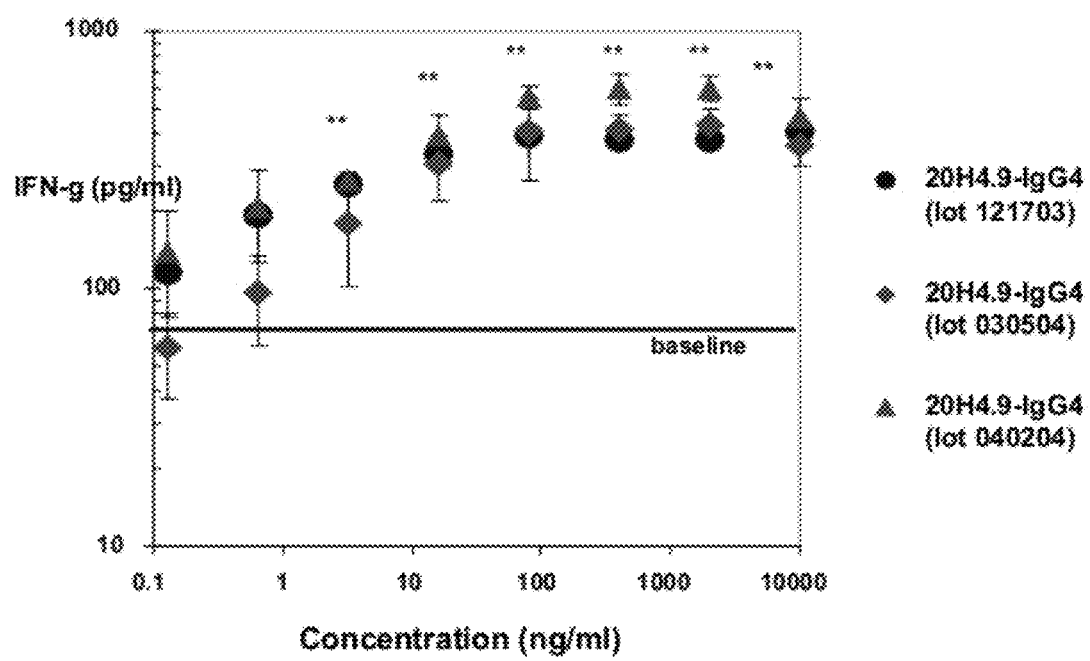

Subsequently, the effect of antibody cross-linking on the functional effect of mab 20H4.9-IgG4 was evaluated. It has been shown that cross-linking of antibodies may result in potentiation of their signaling ability. Thus, a study was conducted to determine the functional activity of several batches of mab 20H4.9-IgG4±an anti-human IgG antibody. As shown in FIG. 14A, significant enhancement of IFN-γ synthesis was observed for all lots tested in the absence of cross-linking antibodies, with a plateau at concentrations of 400 ng/ml. The augmentation of IFNγ synthesis by mab 20H4.9-IgG4 was further enhanced by the addition of anti-human IgG cross-linking antibody as shown in FIG. 14B. Different batches of mab 20H4.9-IgG4 had comparable cellular activities.

Thus, cross-linking of mab 20H4.9-IgG4 resulted in an enhancement of the ability of the antibody to induce IFN-γ synthesis. Antibody cross-linking in vivo may occur by cellular receptors for the Fc portion of immunoglobulins or by

TABLE 1

Comparison of the binding kinetics of mab 20H4.9-IgG4 and mab 20H4.9-IgG1

| antibody | $k_{a1}$ (1/Ms) | $k_{d1}$ (1/s) | ka2 (1/RUs) | kd2 (1/s) | Rmax (RU) | $K_A1$ | $K_D1$ (nM) |
|---|---|---|---|---|---|---|---|
| 20H4.9-IgG1 | 3.43E+04 | 3.85E−04 | 2.30E−05 | 1.51E−03 | 262 | 8.91E+07 | 11.22 |
| 20H4.9-IgG4 | 3.92E+04 | 6.51E−04 | 0.0755 | 0.105 | 409 | 6.02E+07 | 16.61 |

Flow Cytometric Analyses

Figure 12:
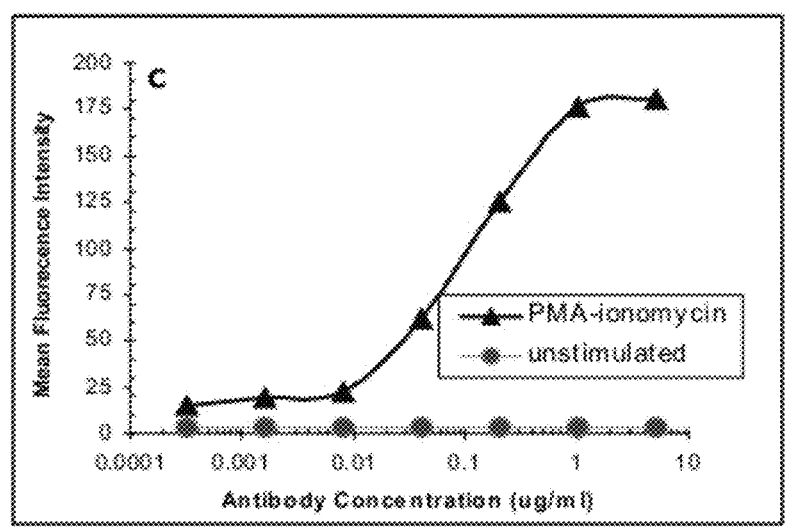
FIG. 12 illustrates the concentration-dependent binding of 20H4.9-IgG4 to PMA ionomycin stimulated human CEM cells, but no binding to unstimulated CEM cells.

Biotinylated mab 20H4.9-IgG4 at concentrations ranging from 0.32 ng/ml to 5 μg/ml was tested for binding to CEM cells±PMA-ionomycin. Mab 20H4.9-IgG4 bound to PMA-ionomycin stimulated CEM cells in a concentration-dependent manner. Saturation was achieved at 0.2 μg/ml. On the other hand, as shown for its parental molecule, mab 20H4.9-IgG1, mab 20H4.9-IgG4 did not bind to CEM cells that were not stimulated with PMA-ionomycin (FIG. 12). Concentration-dependent binding of mab 20H4-0.9-IgG4 was demonstrated in PMA-ionomycin stimulated CEM cells (FIG. 12). Samples were read by flow cytometry.

Cellular/Functional Assays

To confirm that the process of switching the isotype of mab 20H4.9-IgG1 did not alter the activity of the antibody, in vitro studies were conducted to compare the activity of mab 20H4.9-IgG4 to the parent mab 20H4.9-IgG1 in monkey antibody dimerization. Mab 20H4.9-IgG4 is of the IgG4 isotype, which, compared to other IgG isotypes, has low affinity for Fc receptors. However, IgG4 can bind to FcγRI (CD64) expressed on monocytes and neutrophils.

Figure 15:
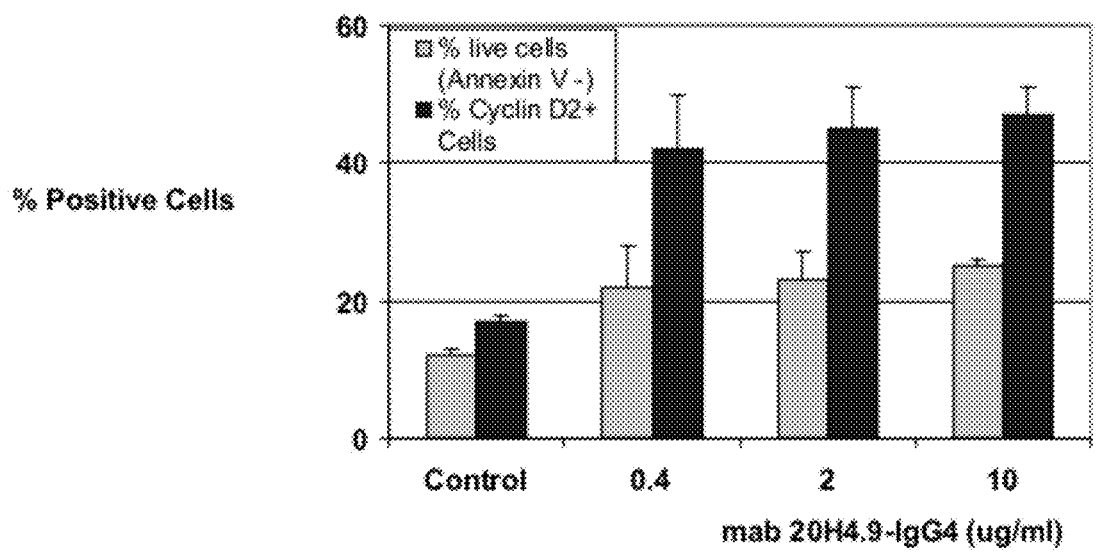
FIG. 15 illustrates the effect of mab 20H4.9-IgG4 on T-cell survival and cell cycle progression. Human T-cells were costimulated with anti-CD3 (1 ug/ml)±mab 20H4.9-IgG4 at the concentrations listed. Six days after initiation of the assays, cells were collected and stained with Annexin-V and propidium iodide to determine the number of live cells (Annexin V/PI negative), or PE-conjugated cyclin D2 to detect cycling cells. Results represent the mean (±SD) of 4 lots of mab 20H4.9-IgG4 tested in parallel.

Two other approaches were used to further characterize mab 20H4.9-IgG4: (i) effect on T-cell survival and (ii) effect on cyclin D2 expression. To determine whether mab 20H4.9-IgG4 could elicit signaling through CD137 on human T-cells and provide co-stimulatory signals to T-cells leading to cell survival and expansion, human T-cells stimulated with anti-CD3 antibodies +/−mab 20H4.9-IgG4 at concentrations known to induce IFN-γ synthesis were stained with annexin-V and propidium iodide to determine the number of live cells (Annexin V/Propidium iodide negative), and with Cyclin D2 to determine its effect on cell progression. FIG. 15 shows the average results of 4 different lots of mab 20H4.9-IgG4 on cyclin D2 expression and survival of T-cells. Concentrations of mab 20H4.9-IgG4 of 0.4-10 pg/ml resulted in an increase in the number of live cells by approximately 1.8-2 fold, and yielded a significant increase in the number of cyclin D2-expressing T-cells (2.5-3 fold).

Example 3

In Vivo Evaluation of 4-1BB Antibodies in a Pharmacodynamic Model in Cynomolgus Monkeys This example illustrates the ability of mab 20H4.9-IgG4 and mab hu39E3.G4 to enhance the antigen specific immune response elicited by DNA vaccines.

Materials and Methods

Experimental animal groups: Female and male cynomolgus monkeys (2.5 to 5.0 kg) were purchased from Charles River BRF (Houston, Tex.) for this study and were housed in pairs. Each experimental group consisted of 4 males and 2 females which were randomized into groups by body weight. Experimental groups were as follows:

Group 1—SW gag and PSA DNA vaccine (2 mg each), day 0, 28, 56, i.m., plus saline control, i.v., on days 12, 15 and 19;

Group 2—SW gag and PSA DNA vaccine (2 mg each), day 0, 28, 56, i.m., plus mab hu39E3.G4, i.v., on days 12, 15 and 19;

Group 3—SW gag and PSA DNA vaccine (2 mg each), day 0, 28, 56, i.m., plus mab 20H4.9-IgG4, i.v., on days 12, 15 and 19;

Group 4—untreated control group.

Immunizations and antibody treatments: PSA and SIV gag DNA vaccines were obtained from David B. Weiner, Department of Pathology and Laboratory of Medicine, University of Pennsylvania. (See, Kim et al., Oncogene 20, 4497-4506 (2001); Muthumani et al., Vaccine 21, 629-637 (2003).)

Monkeys were immunized by the intramuscular route with both PSA and SIV gag DNA constructs (2 mg/construct/immunization) simultaneously, followed by two boosts 4 weeks apart (days 0, 28, and 56). Twelve days after the initial immunization, treatment with mab 20H4.9-IgG4 or mab hu39E3.G4 was initiated. Antibodies were administered i.v, at 50 mg/kg, on days 12, 15, and 19 after the first immunization. This schedule was chosen because it was shown to suppress the antibody response to mab hu39E3.G4.

Clinical and Clinical Pathology

Throughout the course of the study, physical examinations were conducted on all monkeys by the attending veterinarians. Blood samples for hematology and serum chemistry analyses were collected prior to vaccinations and then 12, 42, 70, 97, 134, and 168 days after immunizations.

Immunological Assays

To determine the effect on the immune responses induced by these therapeutic regimens, an enzyme-linked immune spot assay (ELISPOT) was used for the detection of IFN-γ production by antigen-specific stimulated lymphocytes. Blood samples for ELISPOT analyses were collected prior to vaccinations and then 12, 42, 70, 97, 134, and 168 days after immunizations. Synthetic peptides corresponding to the complete sequences of SIV gag and the PSA antigen were used for ex-vivo stimulation of PBMC.

Results

Figure 16A:
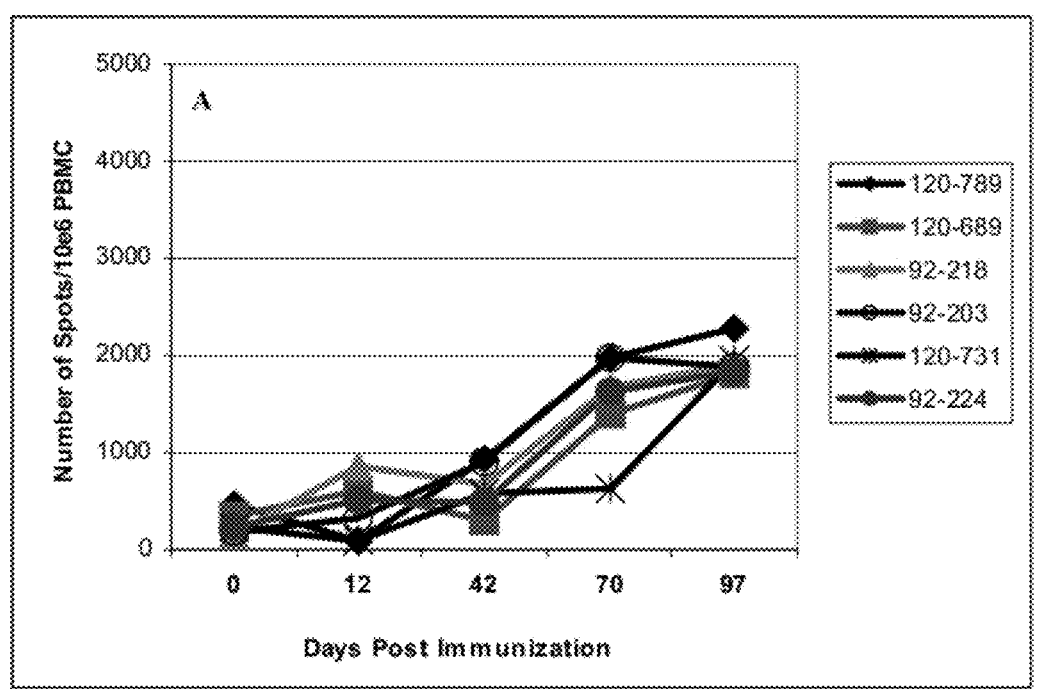
FIG. 16A), SIV gag vaccine (day 0, 28, 56) and mab 20H4.9-IgG4 (day 12, 15 and 19.
Figure 16B:
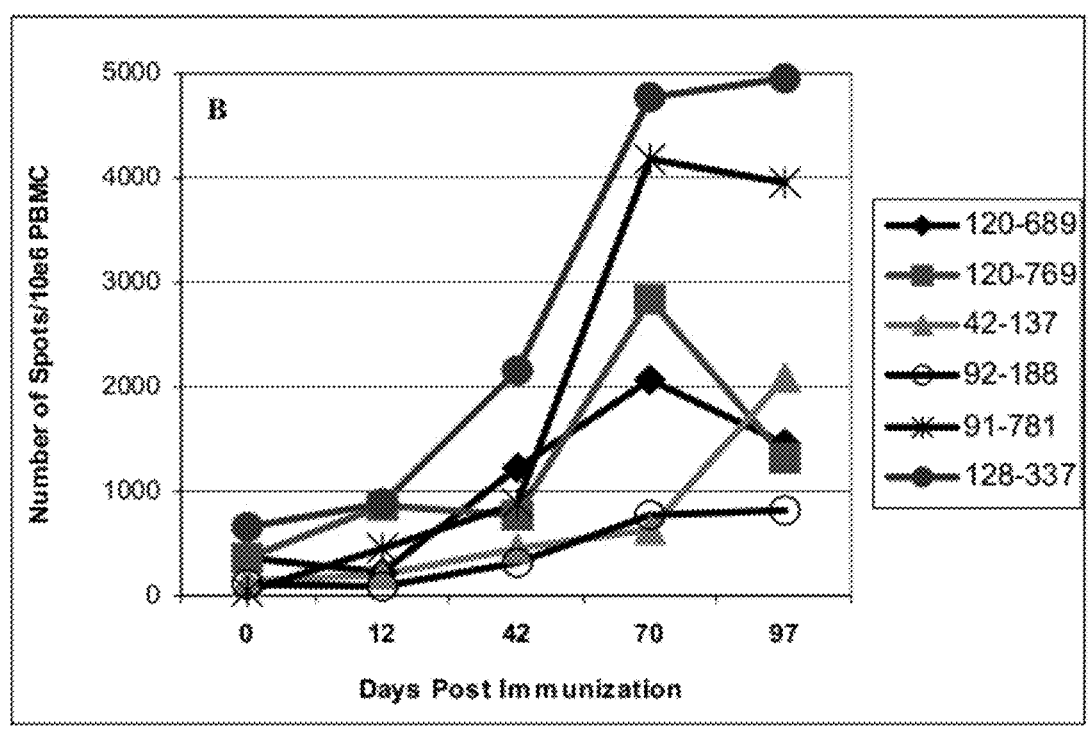
FIG. 16B), or SIV gag vaccine (day 0, 28, 56) and hu39E3.G4 (day 12, 15 and 19.
Figure 16C:
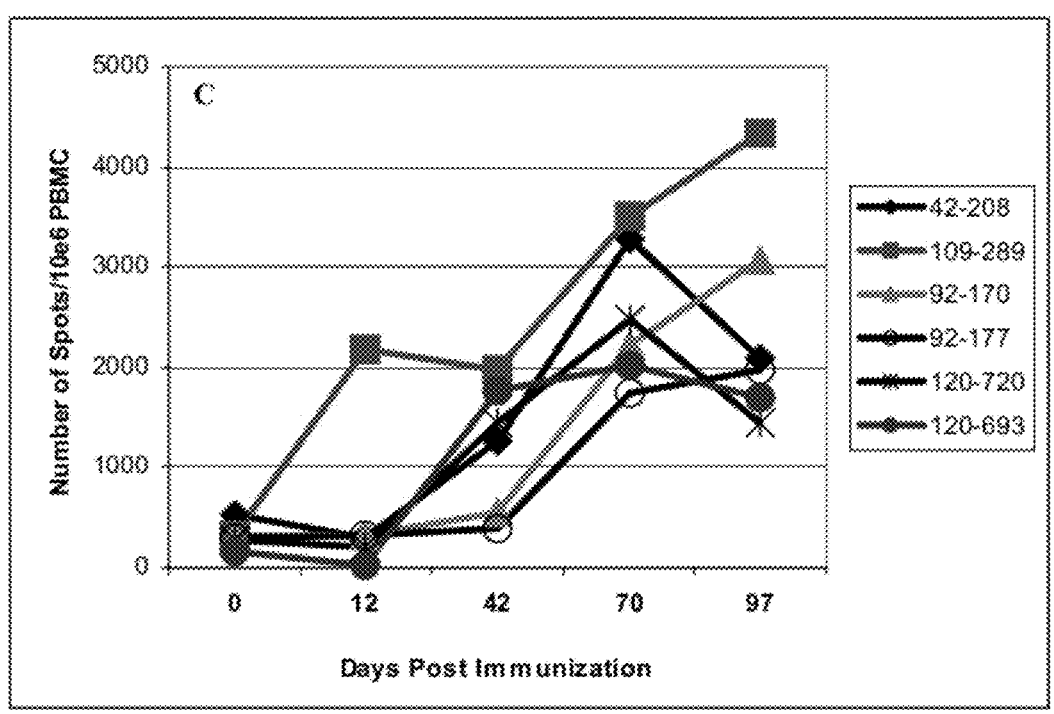
FIG. 16C). A group of animals was left untreated (FIG. 16D). At various times following treatment, blood was collected, and PBMC were separated and evaluated for their ability to secrete IFN-γ in the presence of antigen stimulation.
Figure 16D:
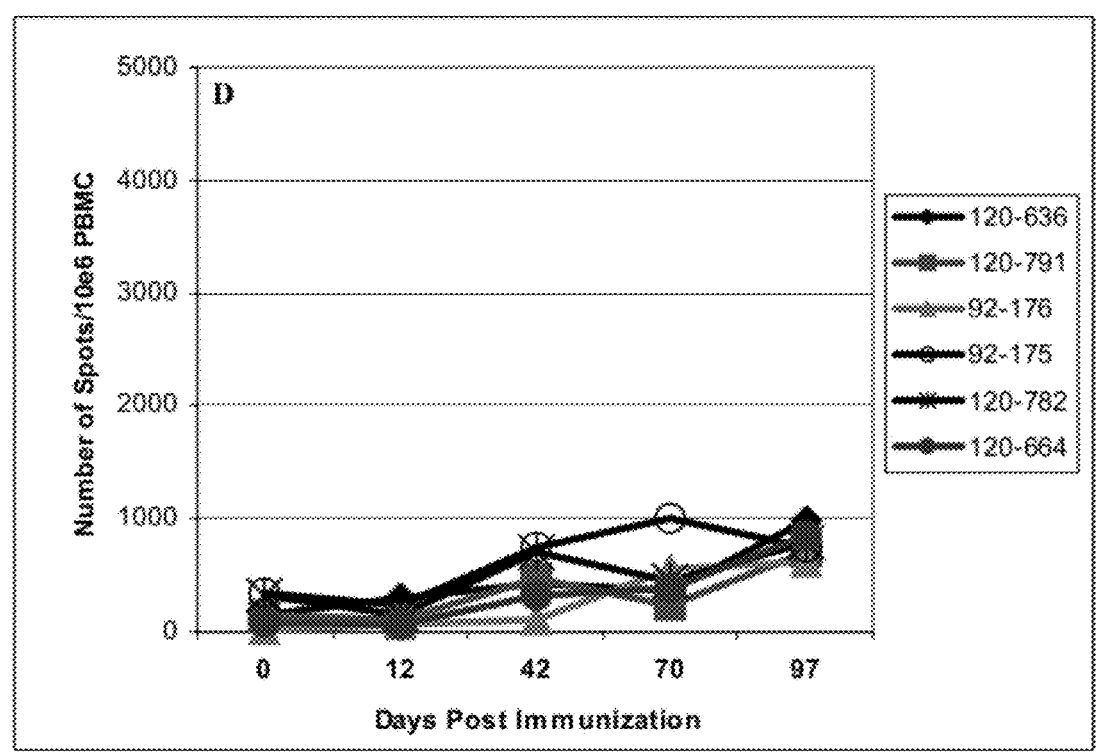
FIG. 16 (FIGS. 16A-16D) shows in cynomolgus monkeys the antigen-specific IFN-γ response as measured by ELISPOT after treatment with a DNA vaccine±anti-human 4-1BB antibodies. Animals were treated with a SIV gag vaccine (day 0, 28, 56.

Antigen-specific IFN-γ secreting cells in response to PSA or SIV gag peptides were quantitated by ELISPOT. FIG. 16 (FIGS. 16A-16D) illustrates the results obtained from Groups 1-4, respectively. The level of response to PSA was very low in all groups, indicating that the vaccine by itself did not induce a measurable and consistent immune response when compared to non-vaccinated animals. On the other hand, SIV gag vaccination alone resulted in significant number of antigen-specific IFN-γ secreting cells that augmented over time (FIG. 16A). Untreated animals (not vaccinated) showed 100-1,000 spots/$10^6$ PBMC throughout the course of the study (FIG. 16D). These results established the threshold response to the vaccine; animals that presented <1,000 spots/$10^6$ PBMC were considered non-responders. In the group of animals that received vaccine, 5 out of 6 monkeys showed an increased response overtime, with a mean number of spots after the third immunization (day 70) of 1,727 spots/$10^6$ PBMC(SD=242, range=1,403-1,968 spots/$10^6$ PBMC). One monkey was considered a non-responder (620 spots/million PBMC). Since in these studies MHC typing was not done, it is likely that the lack of T cell responses to the vaccine by some monkeys may be due to MHC-mismatch. Remarkably, on day 70, 4 out of 6 animals treated with SIV gag plus mab 20H4.9-IgG4 presented a significant higher number of IFN-γ spots (FIG. 16C) compared to control animals (FIG. 16D) and to macaques that were immunized with DNA vaccine alone (FIG. 16A). The mean number of spots after the third immunization for the mab 20H4.9-IgG4-treated group was of 3,465 spots/$10^6$ PBMC(SD=1,236, range=2,070-4,780 spots/$10^6$ PBMC). Two monkeys in that group did not respond to the vaccine (<800 spots/million PBMC). Following the third immunization (day 70), treatment with mab hu39E3.G4 plus DNA vaccine resulted in 6 out of 6 animals considered as responders with a mean number of spots/$10^6$ PBMC of 2,348 (SD=588, range=1,738-3,283) (FIG. 16B). For this group, the range of the number of spots was lower compared to those macaques treated with mab 20H4.9-IgG4.

Treatment with both mab 20H4.9-IgG4 and mab hu9E3.G4 was well tolerated and did not result in any significant changes in clinical signs, clinical chemistry, or hematological parameters relative to control monkeys.

These data show that mab 20H4.9-IgG4 treatment in combination with a DNA vaccine elicited an in vivo enhancement of the magnitude of the specific cellular response to the test antigen relative to controls or to treatment with mab hu39E3.G4, as measured by antigen specific IFN-γ-secreting cells. Since only one dose level of the antibodies and one dosing regimen were used in these preliminary studies, it is unlikely that maximal responses were induced, and further work to optimize conditions is required. Clearly, however, even with this non-optimized protocol, an enhancement of the cellular response to test antigens was achieved with mab 20H4.9-IgG4, suggesting that modulation of CD137 function may be an attractive approach for augmenting the effectiveness of DNA vaccines.

Although the invention has been described in some detail by way of illustration and example for purposes of clarity and understanding, it will be apparent that certain changes and modifications may be practiced within the scope of the appended claims.

The invention claimed is:

1. A monoclonal antibody that specifically binds to 4-1BB comprising a light chain and a heavy chain, wherein said light chain comprises amino acid residues 21-236 of SEQ ID NO:6 and said heavy chain comprises amino acid residues 20-470 of SEQ ID NO: 9.

2. A pharmaceutical composition comprising:
the monoclonal antibody of claim 1; and
a pharmaceutically acceptable carrier.

3. A method for treating a cancer in a subject comprising administering a therapeutically effective amount of the monoclonal antibody or antigen-binding portion thereof of claim 1 to said subject.

* * * * *

UNITED STATES PATENT AND TRADEMARK OFFICE
CERTIFICATE OF CORRECTION

PATENT NO. : 8,716,452 B2
APPLICATION NO. : 13/368710
DATED : May 6, 2014
INVENTOR(S) : Jure-Kunkel et al.

It is certified that error appears in the above-identified patent and that said Letters Patent is hereby corrected as shown below:

On The Title Page, (60) is changed to (63) and should therefore read:
"Related U.S. Application Data"
-- (63) Continuation of U.S. Application No. 12/653,137 filed on December 9, 2009, issued as U.S. Patent No. 8,137,667, which is a continuation of U.S. Divisional Application No. 11/903,106 filed on September 20, 2007, issued as U.S. Patent 7,659,384, which claims priority to Non-Provisional Application No. 10/961,567 filed October 8, 2004, issued as U.S. Patent 7,288,638, which claims priority to U.S. Provisional Application No. 60/510,193, filed October 10, 2003. --

On the Title Page, in the References Cited, Item (56) under Other Publications:
On Page 2, Column 1, delete "Hybridomincs," and insert -- Hybridomics, --

On Page 2, Column 2, delete "monocyle" and insert -- monocyte --

On Page 3, Column 1, delete "Funetion" and insert -- Function --

On Page 3, Column 2, delete "Antologous" and insert -- Autologous --

On Page 3, Column 2, delete ""Genstitutive" and insert -- "Constitutive --

On Page 3, Column 2, delete "1583" and insert -- 1588 --

On Page 3, Column 2, delete "peptidesrecognized" and insert -- peptides recognized --

On Page 3, Column 2, delete "Gastroenteol," and insert -- Gastroenterol, --

Signed and Sealed this
Twenty-fourth Day of February, 2015

Michelle K. Lee
*Deputy Director of the United States Patent and Trademark Office*

In the Specification, Column 1, Lines 1-10 should read:

-- This application is a continuation of U.S. Application Ser. No. 12/653,137 filed on December 9, 2009, issued as U.S. Patent No. 8,137,667, which is a continuation of U.S. Divisional Application No. 11/903,106 filed on September 20, 2007, issued as U.S. Patent 7,659,384, which claims priority to Non-Provisional Application Ser. No. 10/961,567 filed October 8, 2004, issued as U.S. Patent 7,288,638, which claims priority to U.S. Provisional Application No. 60/510,193, filed October 10, 2003 --

SEQUENCE LISTING

<160> NUMBER OF SEQ ID NOS: 9

<210> SEQ ID NO 1
<211> LENGTH: 7057
<212> TYPE: DNA
<213> ORGANISM: Artificial
<220> FEATURE:
<223> OTHER INFORMATION: pD17-20H4.9.h4a coding strand

<400> SEQUENCE: 1

| | | | | | |
|---|---|---|---|---|---|
| cgatgtacgg | gccagatata | cgcgttgaca | ttgattattg | actagttatt | aatagtaatc | 60 |
| aattacgggg | tcattagttc | atagcccata | tatggagttc | cgcgttacat | aacttacggt | 120 |
| aaatggcccg | cctggctgac | cgcccaacga | cccccgccca | ttgacgtcaa | taatgacgta | 180 |
| tgttcccata | gtaacgccaa | tagggacttt | ccattgacgt | caatgggtgg | actatttacg | 240 |
| gtaaactgcc | cacttggcag | tacatcaagt | gtatcatatg | ccaagtacgc | cccctattga | 300 |
| cgtcaatgac | ggtaaatggc | ccgcctggca | ttatgcccag | tacatgacct | tatgggactt | 360 |
| tcctacttgg | cagtacatct | acgtattagt | catcgctatt | accatggtga | tgcggttttg | 420 |
| gcagtacatc | aatgggcgtg | gatagcggtt | tgactcacgg | ggatttccaa | gtctccaccc | 480 |
| cattgacgtc | aatgggagtt | tgttttggca | ccaaaatcaa | cgggactttc | caaaatgtcg | 540 |
| taacaactcc | gccccattga | cgcaaatggg | cggtaggcgt | gtacggtggg | aggtctatat | 600 |
| aagcagagct | ctctggctaa | ctagagaacc | cactgcttac | tggcttatcg | aaattaatac | 660 |
| gactcactat | agggagaccc | aagcttggta | ccgccatgaa | cacctgtggt | tcttcctcc | 720 |
| tcctggtggc | agctcccaga | tgggtcctgt | cccaggtgca | actacagcag | tggggcgcag | 780 |
| gactgttgaa | gccttcggag | accctgtccc | tcacctgcgc | tgtctatggt | gggtccttca | 840 |
| gtggttacta | ctggagctgg | atacgccagt | ccccagagaa | ggggctggag | tggattgggg | 900 |
| aaatcaatca | tggtggatac | gtcacctaca | atccgtccct | cgagagtcga | gtcaccatat | 960 |
| cagtagacac | gtccaagaac | cagttctccc | tgaagctgag | ctctgtgacc | gccgcggaca | 1020 |
| cggctgtata | ttactgtgcg | agggactatg | gtccggggaa | ttatgactgg | tacttcgatc | 1080 |
| tctggggccg | tggcaccctg | gtcactgtct | cctcagctag | caccaagggc | ccatccgtct | 1140 |
| tccccctggc | gccctgctcc | aggagcacct | ccgagagcac | agccgccctg | ggctgcctgg | 1200 |
| tcaaggacta | cttccccgaa | ccggtgacgg | tgtcgtggaa | ctcaggcgcc | ctgaccagcg | 1260 |
| gcgtgcacac | cttcccggct | gtcctacagt | cctcaggact | ctactccctc | agcagcgtgg | 1320 |
| tgaccgtgcc | ctccagcagc | ttgggcacga | agacctacac | ctgcaacgta | gatcacaagc | 1380 |
| ccagcaacac | caaggtggac | aagagagttg | agtccaaata | tggtccacct | tgcccacctt | 1440 |
| gcccagcacc | tgagttcctg | gggggaccat | cagtcttcct | gttccccca | aaacccaagg | 1500 |
| acactctcat | gatctcccgg | acccctgagg | tcacgtgcgt | ggtggtggac | gtgagccagg | 1560 |
| aagaccccga | ggtccagttc | aactggtacg | tggatggcgt | ggaggtgcat | aatgccaaga | 1620 |
| caaagccgcg | ggaggagcag | ttcaacagca | cgtaccgtgt | ggtcagcgtc | ctcaccgtcc | 1680 |
| tgcaccagga | ctggctgaac | ggcaaggagt | acaagtgcaa | ggtctccaac | aaaggcctcc | 1740 |
| cgtcctccat | cgagaaaacc | atctccaaag | ccaaagggca | gccccgagag | ccacaggtgt | 1800 |
| acaccctgcc | cccatcccag | gaggagatga | ccaagaacca | ggtcagcctg | acctgcctgg | 1860 |
| tcaaaggctt | ctaccccagc | gacatcgccg | tggagtggga | gagcaatggg | cagccggaga | 1920 |
| acaactacaa | gaccacgcct | cccgtgctgg | actccgacgg | ctccttcttc | ctctacagca | 1980 |

```
ggctaaccgt ggacaagagc aggtggcagg aggggaatgt cttctcatgc tccgtgatgc  2040
atgaggctct gcacaaccac tacacacaga agagcctctc cctgtctctg ggtaaatgat  2100
ctagagggcc ctattctata gtgtcaccta aatgctagag ctcgctgatc agcctcgact  2160
gtgccttcta gttgccagcc atctgttgtt tgccctccc ccgtgccttc cttgaccctg  2220
gaaggtgcca ctcccactgt cctttcctaa taaaatgagg aaattgcatc gcattgtctg  2280
agtaggtgtc attctattct gggggtggg gtggggcagg acagcaaggg ggaggattgg  2340
gaagacaata gcaggcatgc tggggatgcg gtgggctcta tggcttctga ggcggaaaga  2400
accagctggg gctctagggg gtatccccac gcgccctgta gcggcgcatt aagcgcggcg  2460
ggtgtggtgg ttacgcgcag cgtgaccgct acacttgcca gcgccctagc gcccgctcct  2520
ttcgctttct tcccttcctt tctcgccacg ttcgccgggc ctctcaaaaa agggaaaaaa  2580
agcatgcatc tcaattagtc agcaaccata gtcccgcccc taactccgcc catcccgccc  2640
ctaactccgc ccagttccgc ccattctccg ccccatggct gactaatttt ttttatttat  2700
gcagaggccg aggccgcctc ggcctctgag ctattccaga agtagtgagg aggcttttt  2760 ggaggcctag gcttttgcaa aaagcttgga cagctcaggg ctgcgatttc gcgcaaact  2820 tgacggcaat cctagcgtga aggctggtag gattttatcc ccgctgccat catggttcga  2880
ccattgaact gcatcgtcgc cgtgtcccaa aatatgggga ttggcaagaa cggagaccta  2940
ccctggcctc cgctcaggaa cgagttcaag tacttccaaa gaatgaccac aacctcttca  3000
gtggaaggta aacagaatct ggtgattatg ggtaggaaaa cctggttctc cattcctgag  3060
aagaatcgac cttttaaagga cagaattaat atagttctca gtagagaact caaagaacca  3120
ccacgaggag ctcatttttct tgccaaaagt ttggatgatg ccttaagact tattgaacaa  3180
ccggaattgg caagtaaagt agacatggtt tggatagtcg gaggcagttc tgtttaccag  3240
gaagccatga atcaaccagg ccaccttaga ctctttgtga caaggatcat gcaggaattt  3300
gaaagtgaca cgttttccc agaaattgat ttggggaaat ataaacttct cccagaatac  3360
ccaggcgtcc tctctgaggt ccaggaggaa aaaggcatca agtataagtt tgaagtctac  3420
gagaagaaag actaacagga agatgctttc aagttctctg ctccctcct aaagctatgc  3480 attttttataa gaccatggga cttttgctgg ctttagatct cttgtgaag gaaccttact  3540 tctgtggtgt gacataattg gacaaactac ctacagagat ttaaagctct aaggtaaata  3600 taaaatttt aagtgtataa tgtgttaaac tactgattct aattgtttgt gtatttaga  3660 ttccaaccta tggaactgat gaatgggagc agtggtggaa tgcctttaat gaggaaaacc  3720
tgttttgctc agaagaaatg ccatctagtg atgatgaggc tactgctgac tctcaacatt  3780
ctactcctcc aaaaaagaag agaaaggtag aagacccaa ggactttcct tcagaattgc  3840
taagtttttt gagtcatgct gtgtttagta atagaactct tgcttgcttt gctatttaca  3900
ccacaaagga aaaagctgca ctgctataca agaaaattat ggaaaaatat tctgtaacct  3960
ttataagtag gcataacagt tataatcata acatactgtt ttttcttact ccacacaggc  4020
atagagtgtc tgctattaat aactatgctc aaaaattgtg tacctttagc ttttaatttt  4080 gtaaagggt taataaggaa tatttgatgt atagtgcctt gactagagat cataatcagc  4140
cataccacat ttgtagaggt tttacttgct ttaaaaaacc tcccacacct cccccctgaac  4200 ctgaaacata aaatgaatgc aattgttgtt gttaacttgt ttattgcagc ttataatggt  4260
tacaaataaa gcaatagcat cacaaatttc acaaataaag catttttttc actgcattct  4320
agttgtggtt tgtccaaact catcaatgta tcttatcatg tctggatcgg ctggatgatc  4380
```

```
ctccagcgcg gggatctcat gctggagttc ttcgcccacc ccaacttgtt tattgcagct    4440
tataatggtt acaaataaag caatagcatc acaaatttca caaataaagc attttttca     4500 ctgcattcta gttgtggttt gtccaaactc atcaatgtat cttatcatgt ctgtataccg    4560
tcgacctcta gctagagctt ggcgtaatca tggtcatagc tgtttcctgt gtgaaattgt    4620
tatccgctca caattccaca acatacga gccggaagca taaagtgtaa agcctggggt      4680
gcctaatgag tgagctaact cacattaatt gcgttgcgct cactgcccgc tttccagtcg    4740
ggaaacctgt cgtgccagct gcattaatga atcggccaac gcgcggggag aggcggtttg    4800
cgtattgggc gctcttccgc ttcctcgctc actgactcgc tgcgctcggt cgttcggctg    4860
cggcgagcgg tatcagctca ctcaaaggcg gtaatacggt tatccacaga atcaggggat    4920
aacgcaggaa agaacatgtg agcaaaaggc cagcaaaagg ccaggaaccg taaaaaggcc    4980
gcgttgctgg cgtttttcca taggctccgc cccctgacg agcatcacaa aaatcgacgc     5040
tcaagtcaga ggtggcgaaa cccgacagga ctataaagat accaggcgtt ccccctgga     5100 agctccctcg tgcgctctcc tgttccgacc ctgccgctta ccggataccct gtccgccttt   5160 ctcccttcgg gaagcgtggc gctttctcaa tgctcacgct gtaggtatct cagttcggtg    5220
taggtcgttc gctccaagct gggctgtgtg cacgaacccc ccgttcagcc cgaccgctgc    5280
gccttatccg gtaactatcg tcttgagtcc aacccggtaa gacacgactt atcgccactg    5340
gcagcagcca ctggtaacag gattagcaga gcgaggtatg taggcggtgc tacagagttc    5400
ttgaagtggt ggcctaacta cggctacact agaaggacag tatttggtat ctgcgctctg    5460
ctgaagccag ttaccttcgg aaaaagagtt ggtagctctt gatccggcaa acaaaccacc    5520
gctggtagcg gtggtttttt tgtttgcaag cagcagatta cgcgcagaaa aaaggatct    5580 caagaagatc ctttgatctt ttctacgggg tctgacgctc agtggaacga aaactcacgt    5640
taagggattt tggtcatgag attatcaaaa aggatcttca cctagatcct tttaaattaa    5700
aaatgaagtt ttaaatcaat ctaaagtata tatgagtaaa cttggtctga cagttaccaa    5760
tgcttaatca gtgaggcacc tatctcagcg atctgtctat ttcgttcatc catagttgcc    5820
tgactccccg tcgtgtagat aactacgata cgggagggct taccatctgg ccccagtgct    5880
gcaatgatac cgcgagaccc acgctcaccg gctccagatt tatcagcaat aaaccagcca    5940
gccgaaaggg ccgagcgcag aagtggtcct gcaactttat ccgcctccat ccagtctatt    6000
aattgttgcc gggaagctag agtaagtagt tcgccagtta atagtttgcg caacgttgtt    6060
gccattgcta caggcatcgt ggtgtcacgc tcgtcgtttg gtatggcttc attcagctcc    6120
ggttcccaac gatcaaggcg agttacatga tcccccatgt tgtgcaaaaa agcggttagc    6180
tccttcggtc ctccgatcgt tgtcagaagt aagttggccg cagtgttatc actcatggtt    6240
atggcagcac tgcataattc tcttactgtc atgccatccg taagatgctt ttctgtgact    6300
ggtgagtact caaccaagtc attctgagaa tagtgtatgc ggcgaccgag ttgctcttgc    6360
ccggcgtcaa tacgggataa taccgcgcca catagcagaa ctttaaaagt gctcatcatt    6420
ggaaaacgtt cttcggggcg aaaactctca aggatcttac cgctgttgag atccagttcg    6480
atgtaaccca ctcgtgcacc caactgatct tcagcatctt ttactttcac cagcgtttct    6540
gggtgagcaa aaacaggaag gcaaaatgcc gcaaaaaagg gaataagggc gacacggaaa    6600
tgttgaatac tcatactctt ccttttcaa tattattgaa gcatttatca gggttattgt      6660
ctcatgagcg gatacatatt tgaatgtatt tagaaaaata aacaaatagg ggttccgcgc    6720
acatttcccc gaaaagtgcc acctgacgtc gacggatcgg gagatctgct aggtgacctg    6780
```

```
aggcgcgccg gcttcgaata gccagagtaa ccttttttt  taattttatt ttattttatt    6840
tttgagatgg agtttggcgc cgatctcccg atccccatg  gtcgactctc agtacaatct    6900
gctctgatgc cgcatagtta agccagtatc tgctccctgc ttgtgtgttg gaggtcgctg    6960
agtagtgcgc gagcaaaatt taagctacaa caaggcaagg cttgaccgac aattgcatga    7020
agaatctgct tagggttagg cgttttgcgc tgcttcg                             7057
```

<210> SEQ ID NO 2
<211> LENGTH: 7057
<212> TYPE: DNA
<213> ORGANISM: Artificial
<220> FEATURE:
<223> OTHER INFORMATION: pD17-20H4.9.h4a complementary strand

<400> SEQUENCE: 2

```
gctacatgcc cggtctatat gcgcaactgt aactaataac tgatcaataa ttatcattag      60
ttaatgcccc agtaatcaag tatcgggtat atacctcaag gcgcaatgta ttgaatgcca     120
tttaccgggc ggaccgactg gcgggttgct gggggcgggt aactgcagtt attactgcat     180
acaagggtat cattgcggtt atccctgaaa ggtaactgca gttacccacc tgataaatgc     240
catttgacgg gtgaaccgtc atgtagttca catagtatac ggttcatgcg ggggataact     300
gcagttactg ccatttaccg ggcggaccgt aatcgggtc  atgtactgga ataccctgaa     360
aggatgaacc gtcatgtaga tgcataatca gtagcgataa tggtaccact acgccaaaac     420
cgtcatgtag ttacccgcac ctatcgccaa actgagtgcc cctaaaggtt cagaggtggg     480
gtaactgcag ttaccctcaa acaaaaccgt ggttttagtt gccctgaaag gttttacagc     540
attgttgagg cggggtaact gcgtttaccc gccatccgca catgccaccc tccagatata     600
ttcgtctcga gagaccgatt gatctcttgg gtgacgaatg accgaatagc tttaattatg     660
ctgagtgata tccctctggg ttcgaaccat ggcggtactt tgtggacacc aagaaggagg     720
aggaccaccg tcgagggtct acccaggaca gggtccacgt tgatgtcgtc accccgcgtc     780
ctgacaactt cggaagcctc tgggacaggg agtggacgcg acagatacca cccaggaagt     840
caccaatgat gacctcgacc tatgcggtca ggggtctctt ccccgacctc acctaacccc     900
tttagttagt accacctatg cagtggatgt taggcaggga gctctcagct cagtggtata     960
gtcatctgtg caggttcttg gtcaagaggg acttcgactc gagacactgg cggcgcctgt    1020
gccgacatat aatgacacgc tccctgatac caggccccct aatactgacc atgaagctag    1080
agaccccggc accgtgggac cagtgacaga ggagtcgatc gtggttcccg ggtaggcaga    1140 aggggaccg cgggacgagg tcctcgtgga ggctctcgtg tcggcgggac ccgacggacc     1200
agttcctgat gaaggggctt ggccactgcc acagcacctt gagtccgcgg gactggtcgc    1260
cgcacgtgtg gaagggccga caggatgtca ggagtcctga gatgagggag tcgtcgcacc    1320
actggcacgg gaggtcgtcg aaccgtgct  tctggatgtg gacgttgcat ctagtgttcg    1380
ggtcgttgtg gttccacctg ttctctcaac tcaggtttat accaggtgga acgggtggaa    1440
cgggtcgtgg actcaaggac ccccctggta gtcagaagga caaggggggt tttgggttcc    1500
tgtgagagta ctagagggcc tggggactcc agtgcacgca ccaccacctg cactcggtcc    1560
ttctggggct ccaggtcaag ttgaccatgc acctaccgca cctccacgta ttacggttct    1620
gtttcggcgc cctcctcgtc aagttgtcgt gcatggcaca ccagtcgcag gagtggcagg    1680
acgtggtcct gaccgacttg ccgttcctca tgttcacgtt ccagaggttg tttccggagg    1740
gcaggaggta gctctttttgg tagaggtttc ggtttcccgt cggggctctc ggtgtccaca    1800
```

```
tgtgggacgg gggtagggtc ctcctctact ggttcttggt ccagtcggac tggacggacc    1860
agtttccgaa gatggggtcg ctgtagcggc acctcaccct ctcgttaccc gtcggcctct    1920
tgttgatgtt ctggtgcgga gggcacgacc tgaggctgcc gaggaagaag agatgtcgt    1980 ccgattggca cctgttctcg tccaccgtcc tccccttaca gaagagtacg aggcactacg    2040
tactccgaga cgtgttggtg atgtgtgtct tctcggagag ggacagagac ccatttacta    2100
gatctcccgg gataagatat cacagtggat ttacgatctc gagcgactag tcggagctga    2160
cacggaagat caacggtcgg tagacaacaa acggggaggg ggcacggaag gaactgggac    2220
cttccacggt gagggtgaca ggaaaggatt attttactcc tttaacgtag cgtaacagac    2280
tcatccacag taagataaga ccccccaccc caccccgtcc tgtcgttccc cctcctaacc    2340
cttctgttat cgtccgtacg acccctacgc cacccgagat accgaagact ccgcctttct    2400
tggtcgaccc cgagatcccc catagggtg cgcgggacat cgccgcgtaa ttcgcgccgc    2460
ccacaccacc aatgcgcgtc gcactggcga tgtgaacggt cgcgggatcg cgggcgagga    2520
aagcgaaaga agggaaggaa agagcggtgc aagcggcccg gagagttttt tcccttttt    2580 tcgtacgtag agttaatcag tcgttggtat cagggcgggg attgaggcgg gtagggcggg    2640
gattgaggcg ggtcaaggcg ggtaagaggc ggggtaccga ctgattaaaa aaaataaata    2700
cgtctccggc tccggcggag ccggagactc gataaggtct tcatcactcc tccgaaaaaa    2760
cctccggatc cgaaaacgtt tttcgaacct gtcgagtccc gacgctaaag cgcggtttga    2820
actgccgtta ggatcgcact tccgaccatc ctaaaatagg ggcgacggta gtaccaagct    2880
ggtaacttga cgtagcagcg gcacagggtt ttataccccct aaccgttctt gcctctggat    2940
gggaccggag gcgagtcctt gctcaagttc atgaaggttt cttactggtg ttggagaagt    3000
caccttccat ttgtcttaga ccactaatac ccatccttt ggaccaagag gtaaggactc    3060
ttcttagctg gaaatttcct gtcttaatta tatcaagagt catctcttga gtttcttggt    3120
ggtgctcctc gagtaaaaga acggttttca aacctactac ggaattctga ataacttgtt    3180
ggccttaacc gttcatttca tctgtaccaa acctatcagc ctccgtcaag acaaatggtc    3240
cttcggtact tagttggtcc ggtggaatct gagaaacact gttcctagta cgtccttaaa    3300 cttttcactgt gcaaaaggg tctttaacta aacccctta tatttgaaga gggtcttatg    3360
ggtccgcagg agagactcca ggtcctcctt tttccgtagt tcatattcaa acttcagatg    3420
ctcttctttc tgattgtcct tctacgaaag ttcaagagac gagggagga tttcgatacg    3480 taaaatatt ctggtaccct gaaaacgacc gaaatctaga gaaacacttc cttggaatga    3540
agacaccaca ctgtattaac ctgtttgatg gatgtctcta aatttcgaga ttccatttat    3600
attttaaaaa ttcacatatt acacaatttg atgactaaga ttaacaaaca cataaaatct    3660
aaggttggat accttgacta cttaccctcg tcaccacctt acggaaatta ctcctttgg    3720 acaaaacgag tcttctttac ggtagatcac tactactccg atgacgactg agagttgtaa    3780
gatgaggagg ttttttcttc tctttccatc ttctggggtt cctgaaagga agtcttaacg    3840
attcaaaaaa ctcagtacga cacaaatcat tatcttgaga acgaacgaaa cgataaatgt    3900
ggtgtttcct ttttcgacgt gacgatatgt tcttttaata ccttttata agacattgga    3960 aatattcatc cgtattgtca atattagtat tgtatgacaa aaagaatga ggtgtgtccg    4020 tatctcacag acgataatta ttgatacgag ttttaacac atggaaatcg aaaaattaaa    4080
catttcccca attattcctt ataaactaca tatcacggaa ctgatctcta gtattagtcg    4140
gtatggtgta aacatctcca aaatgaacga aattttttgg agggtgtgga gggggacttg    4200
```

-continued

```
gactttgtat tttacttacg ttaacaacaa caattgaaca aataacgtcg aatattacca   4260
atgtttattt cgttatcgta gtgtttaaag tgtttatttc gtaaaaaagt gacgtaaga    4320
tcaacaccaa acaggtttga gtagttacat agaatagtac agacctagcc gacctactag   4380
gaggtcgcgc ccctagagta cgacctcaag aagcgggtgg ggttgaacaa ataacgtcga   4440
atattaccaa tgtttatttc gttatcgtag tgtttaaagt gtttatttcg taaaaaagt    4500
gacgtaagat caacaccaaa caggtttgag tagttacata gaatagtaca gacatatggc   4560
agctggagat cgatctcgaa ccgcattagt accagtatcg acaaggaca cactttaaca    4620
ataggcgagt gttaaggtgt gttgtatgct cggccttcgt atttcacatt tcggacccca   4680
cggattactc actcgattga gtgtaattaa cgcaacgcga gtgacgggcg aaaggtcagc   4740
cctttggaca gcacggtcga cgtaattact tagccggttg cgcgccctc tccgccaaac    4800
gcataacccg cgagaaggcg aaggagcgag tgactgagcg acgcgagcca gcaagccgac   4860
gccgctcgcc atagtcgagt gagtttccgc cattatgcca ataggtgtct tagtcccta    4920
ttgcgtcctt tcttgtacac tcgttttccg gtcgttttcc ggtccttggc atttttccgg   4980
cgcaacgacc gcaaaaaggt atccgaggcg ggggactgc tcgtagtgtt tttagctgcg    5040
agttcagtct ccaccgcttt gggctgtcct gatatttcta tggtccgcaa aggggacct    5100
tcgagggagc acgcgagagg acaaggctgg gacggcgaat ggcctatgga caggcggaaa   5160
gagggaagcc cttcgcaccg cgaaagagtt acgagtgcga catccataga gtcaagccac   5220
atccagcaag cgaggttcga cccgacacac gtgcttgggg ggcaagtcgg gctggcgacg   5280
cggaataggc cattgatagc agaactcagg ttgggccatt ctgtgctgaa tagcggtgac   5340
cgtcgtcggt gaccattgtc ctaatcgtct cgctccatac atccgccacg atgtctcaag   5400
aacttcacca ccggattgat gccgatgtga tcttcctgtc ataaaccata gacgcgagac   5460
gacttcggtc aatggaagcc ttttctcaa ccatcgagaa ctaggccgtt tgtttggtgg    5520
cgaccatcgc caccaaaaaa acaaacgttc gtcgtctaat gcgcgtcttt ttttcctaga   5580
gttcttctag gaaactagaa aagatgcccc agactgcgag tcaccttgct tttgagtgca   5640
attccctaaa accagtactc taatagtttt tcctagaagt ggatctagga aaatttaatt   5700
tttacttcaa aatttagtta gatttcatat atactcattt gaaccagact gtcaatggtt   5760
acgaattagt cactccgtgg atagagtcgc tagacagata aagcaagtag gtatcaacgg   5820
actgaggggc agcacatcta ttgatgctat gccctcccga atggtagacc ggggtcacga   5880
cgttactatg cgcgctctgg gtgcgagtggc cgaggtctaa atagtcgtta tttggtcggt   5940
cggccttccc ggctcgcgtc ttcaccagga cgttgaaata ggcggaggta ggtcagataa   6000
ttaacaacgg cccttcgatc tcattcatca agccggtcaat tatcaaacgc gttgcaacaa   6060
cggtaacgat gtccgtagca ccacagtgcg agcagcaaac cataccgaag taagtcgagg   6120
ccaagggttg ctagttccgc tcaatgtact aggggggtaca acacgttttt tcgccaatcg   6180
aggaagccag gaggctagca acagtcttca ttcaaccggc gtcacaatag tgagtaccaa   6240
taccgtcgtg acgtattaag agaatgacag tacggtaggc attctacgaa aagacactga   6300
ccactcatga gttggttcag taagactctt atcacatacg ccgctggctc aacgagaacg   6360
ggccgcagtt atgccctatt atggcgcggt gtatcgtctt gaaattttca cgagtagtaa   6420
ccttttgcaa gaagcccgc ttttgagagt tcctagaatg gcgacaactc taggtcaagc    6480
tacattgggt gagcacgtgg gttgactaga agtcgtagaa aatgaaagtg gtcgcaaaga   6540
cccactcgtt tttgtccttc cgttttacgg cgttttttcc cttattcccg ctgtgccttt   6600
```

-continued

```
acaacttatg agtatgagaa ggaaaaagtt ataataactt cgtaaatagt cccaataaca      6660
gagtactcgc ctatgtataa acttacataa atcttttat ttgtttatcc ccaaggcgcg       6720
tgtaaagggg cttttcacgg tggactgcag ctgcctagcc ctctagacga tccactggac      6780
tccgcgcggc cgaagcttat cggtctcatt ggaaaaaaaa attaaaataa aataaaataa      6840
aaactctacc tcaaaccgcg gctagagggc tagggatac cagctgagag tcatgttaga       6900
cgagactacg gcgtatcaat tcggtcatag acgagggacg aacacacaac ctccagcgac      6960
tcatcacgcg ctcgttttaa attcgatgtt gttccgttcc gaactggctg ttaacgtact      7020
tcttagacga atcccaatcc gcaaaacgcg acgaagc                               7057
```

<210> SEQ ID NO 3
<211> LENGTH: 467
<212> TYPE: PRT
<213> ORGANISM: Artificial
<220> FEATURE:
<223> OTHER INFORMATION: pD17-20H4.9.h4a amino acid sequence

<400> SEQUENCE: 3

```
Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Ser Trp Ile Arg Gln Ser Pro Glu Lys Gly Leu
    50                  55                  60

Glu Trp Ile Gly Glu Ile Asn His Gly Gly Tyr Val Thr Tyr Asn Pro
65                  70                  75                  80

Ser Leu Glu Ser Arg Val Thr Ile Ser Val Asp Thr Ser Lys Asn Gln
                85                  90                  95

Phe Ser Leu Lys Leu Ser Ser Val Thr Ala Ala Asp Thr Ala Val Tyr
            100                 105                 110

Tyr Cys Ala Arg Asp Tyr Gly Pro Gly Asn Tyr Asp Trp Tyr Phe Asp
        115                 120                 125

Leu Trp Gly Arg Gly Thr Leu Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Lys Thr Tyr Thr Cys Asn
    210                 215                 220

Val Asp His Lys Pro Ser Asn Thr Lys Val Asp Lys Arg Val Glu Ser
225                 230                 235                 240

Lys Tyr Gly Pro Pro Cys Pro Pro Cys Pro Ala Pro Glu Phe Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser Gln
        275                 280                 285
```

```
Glu Asp Pro Glu Val Gln Phe Asn Trp Tyr Val Asp Gly Val Glu Val
            290                 295                 300

His Asn Ala Lys Thr Lys Pro Arg Glu Glu Gln Phe Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Gly Leu Pro Ser Ser Ile
            340                 345                 350

Glu Lys Thr Ile Ser Lys Ala Lys Gly Gln Pro Arg Glu Pro Gln Val
                355                 360                 365

Tyr Thr Leu Pro Pro Ser Gln Glu Glu Met Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Arg Leu Thr Val
                420                 425                 430

Asp Lys Ser Arg Trp Gln Glu Gly Asn Val Phe Ser Cys Ser Val Met
            435                 440                 445

His Glu Ala Leu His Asn His Tyr Thr Gln Lys Ser Leu Ser Leu Ser
450                 455                 460

Leu Gly Lys
465

<210> SEQ ID NO 4
<211> LENGTH: 6435
<212> TYPE: DNA
<213> ORGANISM: Artificial
<220> FEATURE:
<223> OTHER INFORMATION: pD16gate-20H4.9.LC coding strand

<400> SEQUENCE: 4
gacggatcgg gagatctgct agcccgggtg acctgaggcg cgccggcttc gaatagccag     60
agtaaccttt ttttttaatt ttattttatt ttattttga gatggagttt ggcgccgatc    120
tcccgatccc ctatggtcga ctctcagtac aatctgctct gatgccgcat agttaagcca    180
gtatctgctc cctgcttgtg tgttggaggt cgctgagtag tgcgcgagca aaatttaagc    240
tacaacaagg caaggcttga ccgacaattg catgaagaat ctgcttaggg ttaggcgttt    300
tgcgctgctt cgcgatgtac gggccagata tacgcgttga cattgattat tgactagtta    360
ttaatagtaa tcaattacgg ggtcattagt tcatagccca tatatggagt tccgcgttac    420
ataacttacg gtaaatggcc cgcctggctg accgcccaac gacccccgcc cattgacgtc    480
aataatgacg tatgttccca tagtaacgcc aatagggact ttccattgac gtcaatgggt    540
ggagtattta cggtaaactg cccacttggc agtacatcaa gtgtatcata tgccaagtac    600
gccccctatt gacgtcaatg acggtaaatg gcccgcctgg cattatgccc agtacatgac    660
cttatgggac tttcctactt ggcagtacat ctacgtatta gtcatcgcta ttaccatggt    720
gatgcggttt tggcagtaca tcaatgggcg tggatagcgg tttgactcac ggggatttcc    780
aagtctccac cccattgacg tcaatgggag tttgttttgg caccaaaatc aacgggactt    840
tccaaaatgt cgtaacaact ccgccccatt gacgcaaatg ggcggtaggc gtgtacggtg    900
ggaggtctat ataagcagag ctctctggct aactagagaa cccactgctt actggcttat    960
cgaaattaat acgactcact ataggggagac ccaagcttat caacaagttt gtacaaaaaa   1020
```

```
gcaggctggt accatggaag ccccagctca gcttctcttc ctcctgctac tctggctccc      1080
agataccacc ggagaaattg tgttgacaca gtctccagcc accctgtctt tgtctccagg      1140
ggaaagagcc accctctcct gcagggccag tcagagtgtt agcagctact tagcctggta      1200
ccaacagaaa cctggccagg ctcccaggct cctcatctat gatgcatcca acagggccac      1260
tggcatccca gccaggttca gtggcagtgg gtctgggaca gacttcactc tcaccatcag      1320
cagcctagag cctgaagatt ttgcagttta ttactgtcag cagcgtagca actggcctcc      1380
ggcgctcact ttcggcggag ggaccaaggt ggagatcaaa cgtacggtgg ctgcaccatc      1440
tgtcttcatc ttcccgccat ctgatgagca gttgaaatct ggaactgcct ctgttgtgtg      1500
cctgctgaat aacttctatc ccagagaggc caaagtacag tggaaggtgg ataacgccct      1560
ccaatcgggt aactcccagg agagtgtcac agagcaggac agcaaggaca gcacctacag      1620
cctcagcagc accctgacgc tgagcaaagc agactacgag aaacacaaag tctacgcctg      1680
cgaagtcacc catcagggcc tgagctcgcc cgtcacaaag agcttcaaca ggggagagtg      1740
ttagacccag ctttcttgta caaagtggtt gatctagagg ccctattct atagtgtcac      1800
ctaaatgcta gagctcgctg atcagcctcg actgtgcctt ctagttgcca gccatctgtt      1860
gtttgcccct cccccgtgcc ttccttgacc ctggaaggtg ccactcccac tgtcctttcc      1920
taataaaatg aggaaattgc atcgcattgt ctgagtaggt gtcattctat tctgggggt       1980
ggggtggggc aggacagcaa gggggaggat tgggaagaca atagcaggca tgctgggat       2040
gcggtgggct ctatggcttc tgaggcggaa agaaccagct ggggctctag ggggtatccc      2100
cacgcgccct gtagcggcgc attaagcgcg gcgggtgtgg tggttacgcg cagcgtgacc      2160
gctacacttg ccagcgccct agcgcccgct cctttcgctt tcttcccttc ctttctcgcc      2220
acgttcgccg ggctctcaa aaagggaaa aaagcatgc atctcaatta gtcagcaacc        2280
atagtcccgc ccctaactcc gcccatcccg ccctaactc cgcccagttc cgcccattct       2340
ccgccccatg gctgactaat tttttttatt tatgcagagg ccgaggccgc ctcggcctct      2400
gagctattcc agaagtagtg aggaggcttt tttggaggcc taggcttttg caaaaagctt      2460
gggggacag ctcagggctg cgatttcgcg ccaaacttga cggcaatcct agcgtgaagg       2520
ctggtaggat tttatccccg ctgccatcat ggttcgacca ttgaactgca tcgtcgccgt      2580
gtcccaaaat atggggattg caagaacgg agacctaccc tggcctccgc tcaggaacga      2640
gttcaagtac ttccaaagaa tgaccacaac ctcttcagtg aaggtaaac agaatctggt       2700
gattatgggt aggaaaacct ggttctccat tcctgagaag aatcgacctt taaaggacag      2760
aattaatata gttctcagta gagaactcaa agaaccacca cgaggagctc atttcttgc       2820
caaaagtttg gatgatgcct taagacttat tgaacaaccg gaattggcaa gtaaagtaga      2880
catggtttgg atagtcggag gcagttctgt ttaccaggaa gccatgaatc aaccaggcca      2940
cctcagactc tttgtgacaa ggatcatgca ggaatttgaa agtgacacgt tttcccaga      3000
aattgatttg gggaaatata aacttctccc agaataccca ggcgtcctct ctgaggtcca      3060
ggaggaaaaa ggcatcaagt ataagtttga agtctacgag aagaaagact aacaggaaga      3120
tgctttcaag ttctctgctc ccctcctaaa gctatgcatt tttataagac catgggactt      3180
ttgctggctt tagatctgat cttttgtgaag gaaccttact tctgtggtgt gacataattg      3240
gacaaactac ctacagagat ttaaagctct aaggtaaata taaattttt aagtgtataa       3300
tgtgttaaac tactgattct aattgtttgt gtattttaga ttccaaccta tggaactgat      3360
gaatgggagc agtggtggaa tgcctttaat gaggaaaacc tgttttgctc agaagaaatg      3420
```

```
ccatctagtg atgatgaggc tactgctgac tctcaacatt ctactcctcc aaaaaagaag   3480
agaaaggtag aagaccccaa ggactttcct tcagaattgc taagttttt  gagtcatgct   3540 gtgtttagta atagaactct tgcttgcttt gctatttaca ccacaaagga aaaagctgca   3600
ctgctataca agaaaattat ggaaaaatat tctgtaacct ttataagtag cataacagt    3660 tataatcata acatactgtt ttttcttact ccacacaggc atagagtgtc tgctattaat   3720
aactatgctc aaaaattgtg tacctttagc tttttaattt gtaaggggt  taataaggaa   3780 tatttgatgt atagtgcctt gactagagat cgatcataat cagccatacc acatttgtag   3840
aggttttact tgcttaaaa  aacctcccac acctcccct  gaacctgaaa cataaaatga   3900
atgcaattgt tgttgttaac ttgtttattg cagcttataa tggttacaaa taaagcaata   3960
gcatcacaaa tttcacaaat aaagcatttt tttcactgca ttctagttgt ggtttgtcca   4020
aactcatcaa tgtatcttat catgtctgga tcggctggat gatcctccag cgcgggatc    4080 tcatgctgga gttcttcgcc cacccccaact tgtttattgc agcttataat ggttacaaat  4140
aaagcaatag catcacaaat ttcacaaata aagcatttt  ttcactgcat tctagttgtg   4200
gtttgtccaa actcatcaat gtatcttatc atgtctgtat accgtcgacc tctagctaga   4260
gcttggcgta atcatggtca tagctgtttc ctgtgtgaaa ttgttatccg ctcacaattc   4320
cacacaacat acgagccgga agcataaagt gtaaagcctg gggtgcctaa tgagtgagct   4380
aactcacatt aattgcgttg cgctcactgc ccgctttcca gtcgggaaac ctgtcgtgcc   4440
agctgcatta atgaatcggc caacgcgcgg ggagaggcgg tttgcgtatt gggcgctctt   4500
ccgcttcctc gctcactgac tcgctgcgct cggtcgttcg gctgcggcga gcggtatcag   4560
ctcactcaaa ggcggtaata cggttatcca cagaatcagg ggataacgca ggaaagaaca   4620
tgtgagcaaa aggccagcaa aaggccagga accgtaaaaa ggccgcgttg ctggcgtttt   4680
tccataggct ccgcccccct gacgagcatc acaaaaatcg acgctcaagt cagaggtggc   4740
gaaacccgac aggactataa agataccagg cgtttccccc tggaagctcc ctcgtgcgct   4800
ctcctgttcc gaccctgccg cttaccggat acctgtccgc ctttctccct tcggaagcg   4860 tggcgctttc tcatagctca cgctgtaggt atctcagttc ggtgtaggtc gttcgctcca   4920
agctgggctg tgtgcacgaa ccccccgttc agcccgaccg ctgcgcctta tccggtaact   4980
atcgtcttga gtccaacccg gtaagacacg acttatcgcc actggcagca gccactggta   5040
acaggattag cagagcgagg tatgtaggcg gtgctacaga gttcttgaag tggtggccta   5100
actacggcta cactagaagg aacagtattt ggtatctgcg ctctgctgaa gccagttacc   5160
ttcggaaaaa gagttggtag ctcttgatcc ggcaaacaaa ccaccgctgg tagcggtggt   5220
ttttttgttt gcaagcagca gattacgcgc agaaaaaaag gatctcaaga agatcctttg   5280
atcttttcta cggggtctga cgctcagtgg aacgaaaact cacgttaagg gattttggtc   5340
atgagattat caaaaaggat cttcacctag atcctttta  attaaaaatg aagttttaaa   5400
tcaatctaaa gtatatatga gtaaacttgg tctgacagtt accaatgctt aatcagtgag   5460
gcacctatct cagcgatctg tctatttcgt tcatccatag ttgcctgact ccccgtcgtg   5520
tagataacta cgatacggga gggcttacca tctggcccca gtgctgcaat gataccgcga   5580
gacccacgct caccggctcc agatttatca gcaataaacc agccagcgg  aagggccgag   5640 cgcagaagtg gtcctgcaac tttatccgcc tccatccagt ctattaattg ttgccgggaa   5700
gctagagtaa gtagttcgcc agttaatagt ttgcgcaacg ttgttgccat tgctacaggc   5760
atcgtggtgt cacgctcgtc gtttggtatg gcttcattca gctccggttc ccaacgatca   5820
```

-continued

| | |
|---|---|
| aggcgagtta catgatcccc catgttgtgc aaaaaagcgg ttagctcctt cggtcctccg | 5880 |
| atcgttgtca gaagtaagtt ggccgcagtg ttatcactca tggttatggc agcactgcat | 5940 |
| aattctctta ctgtcatgcc atccgtaaga tgcttttctg tgactggtga gtactcaacc | 6000 |
| aagtcattct gagaatagtg tatgcggcga ccgagttgct cttgcccggc gtcaatacgg | 6060 |
| gataataccg cgccacatag cagaacttta aaagtgctca tcattggaaa acgttcttcg | 6120 |
| gggcgaaaac tctcaaggat cttaccgctg ttgagatcca gttcgatgta acccactcgt | 6180 |
| gcacccaact gatcttcagc atcttttact ttcaccagcg tttctgggtg agcaaaaaca | 6240 |
| ggaaggcaaa atgccgcaaa aaagggaata agggcgacac ggaaatgttg aatactcata | 6300 |
| ctcttccttt ttcaatatta ttgaagcatt tatcagggtt attgtctcat gagcggatac | 6360 |
| atatttgaat gtatttagaa aaataaacaa atagggggttc cgcgcacatt tccccgaaaa | 6420 |
| gtgccacctg acgtc | 6435 |

<210> SEQ ID NO 5
<211> LENGTH: 6435
<212> TYPE: DNA
<213> ORGANISM: Artificial
<220> FEATURE:
<223> OTHER INFORMATION: pD16gate-20H4.9.LC complementary strand

<400> SEQUENCE: 5

| | |
|---|---|
| ctgcctagcc ctctagacga tcgggcccac tggactccgc gcggccgaag cttatcggtc | 60 |
| tcattggaaa aaaaaattaa aataaaataa aataaaaact ctacctcaaa ccgcggctag | 120 |
| agggctaggg gataccagct gagagtcatg ttagacgaga ctacggcgta tcaattcggt | 180 |
| catagacgag ggacgaacac acaacctcca gcgactcatc acgcgctcgt tttaaattcg | 240 |
| atgttgttcc gttccgaact ggctgttaac gtacttctta gacgaatccc aatccgcaaa | 300 |
| acgcgacgaa gcgctacatg cccggtctat atgcgcaact gtaactaata actgatcaat | 360 |
| aattatcatt agttaatgcc ccagtaatca agtatcgggt atatacctca aggcgcaatg | 420 |
| tattgaatgc catttaccgg gcggaccgac tggcgggttg ctgggggcgg gtaactgcag | 480 |
| ttattactgc atacaagggt atcattgcgg ttatccctga aggtaactg cagttaccca | 540 |
| cctcataaat gccatttgac gggtgaaccg tcatgtagtt cacatagtat acggttcatg | 600 |
| cgggggataa ctgcagttac tgccatttac cgggcggacc gtaatacggg tcatgtactg | 660 |
| gaatacccctg aaaggatgaa ccgtcatgta gatgcataat cagtagcgat aatggtacca | 720 |
| ctacgccaaa accgtcatgt agttacccgc acctatcgcc aaactgagtg cccctaaagg | 780 |
| ttcagaggtg gggtaactgc agttaccctc aaacaaaacc gtggttttag ttgccctgaa | 840 |
| aggttttaca gcattgttga ggcggggtaa ctgcgtttac ccgccatccg cacatgccac | 900 |
| cctccagata tattcgtctc gagagaccga ttgatctctt gggtgacgaa tgaccgaata | 960 |
| gctttaatta tgctgagtga tatccctctg gttcgaata gttgttcaaa catgttttt | 1020 |
| cgtccgacca tggtaccttc ggggtcgagt cgaagagaag gaggacgatg agaccgaggg | 1080 |
| tctatggtgg cctctttaac acaactgtgt cagaggtcgg tggacagaa acagaggtcc | 1140 |
| cctttctcgg tgggagagga cgtcccggtc agtctcacaa tcgtcgatga atcggaccat | 1200 |
| ggttgtcttt ggaccggtcc gagggtccga ggagtagata ctacgtaggt tgtcccggtg | 1260 |
| accgtagggt cggtccaagt caccgtcacc cagaccctgt ctgaagtgag agtggtagtc | 1320 |
| gtcggatctc ggacttctaa aacgtcaaat aatgacagtc gtcgcatcgt tgaccggagg | 1380 |
| ccgcgagtga aagccgcctc cctggttcca cctctagttt gcatgccacc gacgtggtag | 1440 |

```
acagaagtag aagggcggta gactactcgt caactttaga ccttgacgga gacaacacac    1500
ggacgactta ttgaagatag ggtctctccg gtttcatgtc accttccacc tattgcggga    1560
ggttagccca ttgagggtcc tctcacagtg tctcgtcctg tcgttcctgt cgtggatgtc    1620
ggagtcgtcg tgggactgcg actcgtttcg tctgatgctc tttgtgtttc agatgcggac    1680
gcttcagtgg gtagtcccgg actcgagcgg gcagtgtttc tcgaagttgt cccctctcac    1740
aatctgggtc gaaagaacat gtttcaccaa ctagatctcc cgggataaga tatcacagtg    1800
gatttacgat ctcgagcgac tagtcggagc tgacacggaa gatcaacggt cggtagacaa    1860
caaacgggga gggggcacgg aaggaactgg gaccttccac ggtgagggtg acaggaaagg    1920
attattttac tcctttaacg tagcgtaaca gactcatcca cagtaagata agaccccca    1980 ccccaccccg tcctgtcgtt cccctccta acccttctgt tatcgtccgt acgaccccta    2040
cgccacccga gataccgaag actccgcctt tcttggtcga ccccgagatc ccccataggg    2100
gtgcgcggga catcgccgcg taattcgcgc cgcccacacc accaatgcgc gtcgcactgg    2160
cgatgtgaac ggtcgcggga tcgcgggcga ggaaagcgaa agaagggaag gaaagagcgg    2220
tgcaagcggc ccggagagtt ttttcccttt ttttcgtacg tagagttaat cagtcgttgg    2280
tatcagggcg gggattgagg cgggtagggc ggggattgag gcgggtcaag gcgggtaaga    2340
ggcggggtac cgactgatta aaaaaaataa atacgtctcc ggctccggcg gagccggaga    2400
ctcgataagg tcttcatcac tcctccgaaa aaacctccgg atccgaaaac gttttcgaa    2460 cccccctgtc gagtcccgac gctaaagcgc ggtttgaact gccgttagga tcgcacttcc    2520
gaccatccta aaatagggc gacggtagta ccaagctggt aacttgacgt agcagcggca    2580
cagggtttta tacccctaac cgttcttgcc tctggatggg accggaggcg agtccttgct    2640
caagttcatg aaggtttctt actggtgttg gagaagtcac cttccatttg tcttagacca    2700 ctaatacccca tccttttgga ccaagaggta aggactcttc ttagctggaa attcctgtc    2760 ttaattatat caagagtcat ctcttgagtt tcttggtggt gctcctcgag taaaagaacg    2820
gttttcaaac ctactacgga attctgaata acttgttggc cttaaccgtt catttcatct    2880
gtaccaaacc tatcagcctc cgtcaagaca aatggtcctt cggtacttag ttggtccggt    2940
ggagtctgag aaacactgtt cctagtacgt ccttaaactt tcactgtgca aaaagggtct    3000
ttaactaaac ccctttatat ttgaagaggg tcttatgggt ccgcaggaga gactccaggt    3060
cctccttttt ccgtagttca tattcaaact tcagatgctc ttctttctga ttgtccttct    3120
acgaaagttc aagagacgag gggaggattt cgatacgtaa aaatattctg gtaccctgaa    3180
aacgaccgaa atctagacta gaaacacttc cttggaatga agacaccaca ctgtattaac    3240
ctgtttgatg gatgtctcta aatttcgaga ttccatttat attttaaaaa ttcacatatt    3300
acacaatttg atgactaaga ttaacaaaca cataaaatct aaggttggat accttgacta    3360
cttaccctcg tcaccacctt acggaaatta ctccttttgg acaaaacgag tcttctttac    3420
ggtagatcac tactactccg atgacgactg agagttgtaa gatgaggagg ttttttcttc    3480
tctttccatc ttctgggggtt cctgaaagga agtcttaacg attcaaaaaa ctcagtacga    3540
cacaaatcat tatcttgaga acgaacgaaa cgataaatgt ggtgtttcct ttttcgacgt    3600
gacgatatgt tctttaata cctttttata agacattgga atattcatc cgtattgtca    3660 atattagtat tgtatgacaa aaaagaatga ggtgtgtccg tatctcacag acgataatta    3720
ttgatacgag tttttaacac atggaaatcg aaaaattaaa catttcccca attattcctt    3780
ataaactaca tatcacggaa ctgatctcta gctagtatta gtcggtatgg tgtaaacatc    3840
```

```
tccaaaatga acgaaatttt ttggagggtg tggagggggga cttggacttt gtatttttact    3900
tacgttaaca caacaattg aacaaataac gtcgaatatt accaatgttt atttcgttat       3960
cgtagtgttt aaagtgttta tttcgtaaaa aaagtgacgt aagatcaaca ccaaacaggt     4020
ttgagtagtt acatagaata gtacagacct agccgaccta ctaggaggtc gcgcccctag    4080
agtacgacct caagaagcgg gtggggttga acaaataacg tcgaatatta ccaatgttta    4140
tttcgttatc gtagtgttta aagtgtttat ttcgtaaaaa aagtgacgta agatcaacac    4200
caaacaggtt tgagtagtta catagaatag tacagacata tggcagctgg agatcgatct    4260
cgaaccgcat tagtaccagt atcgacaaag gacacacttt aacaataggc gagtgttaag    4320
gtgtgttgta tgctcggcct tcgtatttca catttcggac cccacggatt actcactcga    4380
ttgagtgtaa ttaacgcaac gcgagtgacg ggcgaaaggt cagcccttg acagcacgg     4440
tcgacgtaat tacttagccg gttgcgcgcc cctctccgcc aaacgcataa cccgcgagaa    4500
ggcgaaggag cgagtgactg agcgacgcga gccagcaagc cgacgccgct cgccatagtc    4560
gagtgagttt ccgccattat gccaataggt gtcttagtcc cctattgcgt cctttcttgt    4620
acactcgttt tccggtcgtt ttccggtcct tggcattttt ccggcgcaac gaccgcaaaa    4680
aggtatccga ggcgggggga ctgctcgtag tgttttttagc tgcgagttca gtctccaccg    4740
ctttgggctg tcctgatatt tctatggtcc gcaaaggggg accttcgagg gagcacgcga    4800
gaggacaagg ctgggacggc gaatggccta tggacaggcg gaaagaggga gcccttcgc    4860
accgcgaaag agtatcgagt gcgacatcca tagagtcaag ccacatccag caagcgaggt    4920
tcgacccgac acacgtgctt gggggcaag tcgggctggc gacgcggaat aggccattga    4980
tagcagaact caggttgggc cattctgtgc tgaatagcgg tgaccgtcgt cggtgaccat    5040
tgtcctaatc gtctcgctcc atacatccgc cacgatgtct caagaacttc accaccggat    5100
tgatgccgat gtgatcttcc ttgtcataaa ccatagacgc gagacgactt cggtcaatgg    5160
aagccttttt ctcaaccatc gagaactagg ccgtttgttt ggtggcgacc atcgccacca    5220
aaaaacaaa cgttcgtcgt ctaatgcgcg tctttttttc ctagagttct tctaggaaac    5280
tagaaaagat gccccagact gcgagtcacc ttgcttttga gtgcaattcc ctaaaaccag    5340
tactctaata gtttttccta gaagtggatc taggaaaatt taattttac ttcaaaattt     5400
agttagattt catatatact catttgaacc agactgtcaa tggttacgaa ttagtcactc    5460
cgtggataga gtcgctagac agataaagca agtaggtatc aacggactga ggggcagcac    5520
atctattgat gctatgccct cccgaatggt agaccgggt cacgacgtta ctatggcgct     5580
ctgggtgcga gtggccgagg tctaaatagt cgttatttgg tcggtcggcc ttcccggctc    5640
gcgtcttcac caggacgttg aaataggcgg aggtaggtca gataattaac aacgcccctt    5700
cgatctcatt catcaagcgg tcaattatca aacgcgttgc aacaacggta acgatgtccg    5760
tagcaccaca gtgcgagcag caaaccatac cgaagtaagt cgaggccaag ggttgctagt    5820
tccgctcaat gtactagggg gtacaacacg ttttttcgcc aatcgaggaa gccaggaggc    5880
tagcaacagt cttcattcaa ccggcgtcac aatagtgagt accaataccg tcgtgacgta    5940
ttaagagaat gacagtacgg taggcattct acgaaaagac actgaccact catgagttgg    6000
ttcagtaaga ctcttatcac atacgccgct ggctcaacga gaacgggccg cagttatgcc    6060
ctattatggc gcggtgtatc gtcttgaaat tttcacgagt agtaacctttt tgcaagaagc    6120
cccgcttttg agagttccta gaatggcgac aactctaggt caagctacat tgggtgagca    6180
cgtgggttga ctagaagtcg tagaaaatga aagtggtcgc aaagacccac tcgttttttgt    6240
```

```
ccttccgttt  tacggcgttt  tttcccttat  tcccgctgtg  cctttacaac  ttatgagtat    6300
gagaaggaaa  aagttataat  aacttcgtaa  atagtcccaa  taacagagta  ctcgcctatg    6360
tataaactta  cataaatctt  tttatttgtt  tatccccaag  gcgcgtgtaa  agggctttt     6420 cacggtggac  tgcag                                                         6435
```

<210> SEQ ID NO 6
<211> LENGTH: 236
<212> TYPE: PRT
<213> ORGANISM: Artificial
<220> FEATURE:
<223> OTHER INFORMATION: pD16gate-20H4.9.LC amino acid sequence

<400> SEQUENCE: 6

```
Met Glu Ala Pro Ala Gln Leu Leu Phe Leu Leu Leu Trp Leu Pro
1               5                   10                  15

Asp Thr Thr Gly Glu Ile Val Leu Thr Gln Ser Pro Ala Thr Leu Ser
                20                  25                  30

Leu Ser Pro Gly Glu Arg Ala Thr Leu Ser Cys Arg Ala Ser Gln Ser
            35                  40                  45

Val Ser Ser Tyr Leu Ala Trp Tyr Gln Gln Lys Pro Gly Gln Ala Pro
        50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110

Asn Trp Pro Pro Ala Leu Thr Phe Gly Gly Gly Thr Lys Val Glu Ile
        115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 7
<211> LENGTH: 1413
<212> TYPE: DNA
<213> ORGANISM: Artificial
<220> FEATURE:
<223> OTHER INFORMATION: 20H4.9-IgG1 coding strand

<400> SEQUENCE: 7

```
atgaaacacc  tgtggttctt  cctcctcctg  gtggcagctc  ccagatgggt  cctgtcccag     60
gtgcaactac  agcagtgggg  cgcaggactg  ttgaagcctt  cggagaccct  gtccctcacc    120
tgcgctgtct  atggtgggtc  cttcagtggt  tactactgga  gctggatacg  ccagtcccca    180 gagaagggc   tggagtggat  tgggaaatc   aatcatggtg  gatacgtcac  ctacaatccg    240
```

```
tccctcgaga gtcgagtcac catatcagta gacacgtcca agaaccagtt ctccctgaag      300
ctgagctctg tgaccgccgc ggacacggct gtatattact gtgcgaggga ctatggtccg      360
gggaattatg actggtactt cgatctctgg ggccgtggca ccctggtcac tgtctcctca      420
gcctccacca agggcccatc ggtcttcccc ctggcaccct cctccaagag cacctctggg      480
ggcacagcgg ccctgggctg cctggtcaag gactacttcc ccgaaccggt gacggtgtcg      540
tggaactcag gcgccctgac cagcggcgtg cacaccttcc cggctgtcct acagtcctca      600
ggactctact ccctcagcag cgtggtgacc gtgccctcca gcagcttggg cacccagacc      660
tacatctgca acgtgaatca caagcccagc aacaccaagg tggacaagag agttgagccc      720
aaatcttgtg acaaaactca cacatgccca ccgtgcccag cacctgaact cctggggggga      780 ccgtcagtct tcctcttccc cccaaaaccc aaggacaccc tcatgatctc ccggacccct      840
gaggtcacat gcgtggtggt ggacgtgagc cacgaagacc ctgaggtcaa gttcaactgg      900
tacgtggacg gcgtggaggt gcataatgcc aagacaaagc cgcgggagga gcagtacaac      960
agcacgtacc gtgtggtcag cgtcctcacc gtcctgcacc aggactggct gaatggcaag      1020
gagtacaagt gcaaggtctc caacaaagcc ctcccagccc ccatcgagaa aaccatctcc      1080
aaagccaaag ggcagccccg agaaccacag gtgtacaccc tgcccccatc ccgggatgag      1140
ctgaccaaga accaggtcag cctgacctgc ctggtcaaag gcttctatcc cagcgacatc      1200
gccgtggagt gggagagcaa tgggcagccg gagaacaact acaagaccac gcctcccgtg      1260
ctggactccg acggctcctt cttcctctac agcaagctca ccgtggacaa gagcaggtgg      1320
cagcagggga acgtcttctc atgctccgtg atgcatgagg ctctgcacaa ccactacacg      1380
cagaagagcc tctccctgtc cccgggtaaa tga                                 1413
```

<210> SEQ ID NO 8
<211> LENGTH: 1413
<212> TYPE: DNA
<213> ORGANISM: Artificial
<220> FEATURE:
<223> OTHER INFORMATION: 20H4.9-IgG1 complementary strand

<400> SEQUENCE: 8

```
tactttgtgg acaccaagaa ggaggaggac caccgtcgag ggtctaccca ggacagggtc       60
cacgttgatg tcgtcacccc gcgtcctgac aacttcggaa gcctctggga cagggagtgg      120
acgcgacaga taccacccag gaagtcacca atgatgacct cgacctatgc ggtcaggggt      180
ctcttccccg acctcaccta accccttag ttagtaccac ctatgcagtg gatgttaggc       240
agggagctct cagctcagtg gtatagtcat ctgtgcaggt tcttggtcaa gagggacttc      300
gactcgagac actggcggcg cctgtgccga catataatga cacgctccct gataccaggc      360
cccttaatac tgaccatgaa gctagagacc ccggcaccgt gggaccagtg acagaggagt      420
cggaggtggt tcccgggtag ccagaagggg gaccgtggga ggaggttctc gtggagaccc      480
ccgtgtcgcc gggaccccgac ggaccagttc ctgatgaagg gcttggcca ctgccacagc       540 accttgagtc cgcgggactg gtcgccgcac gtgtggaagg gccgacagga tgtcaggagt      600
cctgagatga gggagtcgtc gcaccactgg cacgggaggt cgtcgaaccc gtgggtctgg      660
atgtagacgt tgcacttagt gttcgggtcg ttgtggttcc acctgttctc tcaactcggg      720
tttagaacac tgttttgagt gtgtacgggt ggcacgggtc gtggacttga gaccccccct      780
ggcagtcaga aggagaaggg ggggttttggg ttcctgtggg agtactagag ggcctgggga     840
ctccagtgta cgcaccacca cctgcactcg gtgcttctgg gactccagtt caagttgacc      900
```

-continued

```
atgcacctgc cgcacctcca cgtattacgg ttctgtttcg gcgccctcct cgtcatgttg    960
tcgtgcatgg cacaccagtc gcaggagtgg caggacgtgg tcctgaccga cttaccgttc   1020
ctcatgttca cgttccagag gttgtttcgg gagggtcggg ggtagctctt ttggtagagg   1080
tttcggtttc ccgtcggggc tcttggtgtc cacatgtggg acgggggtag ggccctactc   1140
gactggttct tggtccagtc ggactggacg gaccagtttc cgaagatagg gtcgctgtag   1200
cggcacctca ccctctcgtt acccgtcggc ctcttgttga tgttctggtg cggagggcac   1260
gacctgaggc tgccgaggaa gaaggagatg tcgttcgagt ggcacctgtt ctcgtccacc   1320
gtcgtcccct tgcagaagag tacgaggcac tactactcc gagacgtgtt ggtgatgtgc    1380
gtcttctcgg agagggacag gggcccattt act                                1413
```

<210> SEQ ID NO 9
<211> LENGTH: 470
<212> TYPE: PRT
<213> ORGANISM: Artificial
<220> FEATURE:
<223> OTHER INFORMATION: 20H4.9-IgG1 amino acid sequence

<400> SEQUENCE: 9

```
Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Ser Trp Ile Arg Gln Ser Pro Glu Lys Gly Leu
    50                  55                  60

Glu Trp Ile Gly Glu Ile Asn His Gly Gly Tyr Val Thr Tyr Asn Pro
65                  70                  75                  80

Ser Leu Glu Ser Arg Val Thr Ile Ser Val Asp Thr Ser Lys Asn Gln
                85                  90                  95

Phe Ser Leu Lys Leu Ser Ser Val Thr Ala Ala Asp Thr Ala Val Tyr
            100                 105                 110

Tyr Cys Ala Arg Asp Tyr Gly Pro Gly Asn Tyr Asp Trp Tyr Phe Asp
        115                 120                 125

Leu Trp Gly Arg Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270
```

```
Thr Leu Met Ile Ser Arg Thr Pro Glu Val Thr Cys Val Val Val Asp
        275                 280                 285
Val Ser His Glu Asp Pro Glu Val Lys Phe Asn Trp Tyr Val Asp Gly
    290                 295                 300
Val Glu Val His Asn Ala Lys Thr Lys Pro Arg Glu Glu Gln Tyr Asn
305                 310                 315                 320
Ser Thr Tyr Arg Val Val Ser Val Leu Thr Val Leu His Gln Asp Trp
            325                 330                 335
Leu Asn Gly Lys Glu Tyr Lys Cys Lys Val Ser Asn Lys Ala Leu Pro
        340                 345                 350
Ala Pro Ile Glu Lys Thr Ile Ser Lys Ala Lys Gly Gln Pro Arg Glu
        355                 360                 365
Pro Gln Val Tyr Thr Leu Pro Pro Ser Arg Asp Glu Leu Thr Lys Asn
    370                 375                 380
Gln Val Ser Leu Thr Cys Leu Val Lys Gly Phe Tyr Pro Ser Asp Ile
385                 390                 395                 400
Ala Val Glu Trp Glu Ser Asn Gly Gln Pro Glu Asn Asn Tyr Lys Thr
            405                 410                 415
Thr Pro Pro Val Leu Asp Ser Asp Gly Ser Phe Phe Leu Tyr Ser Lys
            420                 425                 430
Leu Thr Val Asp Lys Ser Arg Trp Gln Gln Gly Asn Val Phe Ser Cys
        435                 440                 445
Ser Val Met His Glu Ala Leu His Asn His Tyr Thr Gln Lys Ser Leu
    450                 455                 460
Ser Leu Ser Pro Gly Lys
465             470
```